United States Patent [19]

Crapo et al.

[11] Patent Number: 5,994,339
[45] Date of Patent: *Nov. 30, 1999

[54] OXIDANT SCAVENGERS

[75] Inventors: James D. Crapo; Irwin Fridovich; Tim Oury; Brian J. Day; Rodney J. Folz, all of Durham, N.C.; Bruce A. Freeman, Birmingham, Ala.

[73] Assignees: University of Alabama at Birmingham Research Foundation, Birmingham, Ala.; Duke University, Durham, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/476,866

[22] Filed: Jun. 7, 1995

Related U.S. Application Data

[63] Continuation-in-part of application No. 08/322,766, Oct. 13, 1994, abandoned, which is a continuation-in-part of application No. 08/136,207, Oct. 15, 1993, abandoned.

[51] Int. Cl.⁶ .......................... A01N 55/02; C07B 47/00; C09K 15/04; C09K 15/32
[52] U.S. Cl. .......................... 514/185; 540/145; 252/399; 252/400.23; 435/189; 435/252.3; 435/320.1
[58] Field of Search ................................. 435/85.1, 94.4, 435/189, 240.2, 320.1, 252.3, 254; 536/23.2, 27; 424/94.4; 514/185; 540/145; 252/399, 400.23

[56] References Cited

U.S. PATENT DOCUMENTS

| | | | |
|---|---|---|---|
| 4,614,723 | 9/1986 | Schmidt | 436/536 |
| 4,746,735 | 5/1988 | Kruper, Jr. et al. | 540/145 |
| 4,758,422 | 7/1988 | Quay | 424/9 |
| 4,837,221 | 6/1989 | Bonnett | 514/410 |
| 4,851,403 | 7/1989 | Picker et al. | 424/485 |
| 4,895,719 | 1/1990 | Radhakrishnam | 424/45 |
| 4,963,367 | 10/1990 | Ecanow | 424/485 |
| 5,051,337 | 9/1991 | Sakoda et al. | 430/270 |
| 5,130,245 | 7/1992 | Marklund et al. | 435/189 |
| 5,162,519 | 11/1992 | Bonnett | 514/185 |
| 5,169,630 | 12/1992 | Okaya et al. | 424/401 |
| 5,171,680 | 12/1992 | Mullenbach et al. | 435/189 |
| 5,202,317 | 4/1993 | Bruice | 514/185 |
| 5,217,966 | 6/1993 | Bruice | 514/185 |
| 5,223,538 | 6/1993 | Fridovich | 514/616 |
| 5,227,405 | 7/1993 | Fridovich | 514/612 |
| 5,236,914 | 8/1993 | Meunier | 514/185 |
| 5,236,915 | 8/1993 | Fiel | 540/145 |
| 5,248,603 | 9/1993 | Marklund et al. | 435/189 |
| 5,262,532 | 11/1993 | Tweedle et al. | 540/145 |
| 5,284,647 | 2/1994 | Niedballa | 424/81 |
| 5,366,729 | 11/1994 | Marklund et al. | 424/96.4 |
| 5,472,691 | 12/1995 | Marklund et al. | 424/94.4 |
| 5,493,017 | 2/1996 | Therien et al. | 424/94.4 |

FOREIGN PATENT DOCUMENTS

| | | |
|---|---|---|
| 0 127 797 | 12/1984 | European Pat. Off. . |
| 0 186 962 | 7/1986 | European Pat. Off. . |
| 0 282 899 | 9/1988 | European Pat. Off. . |
| 0 336 879 | 10/1989 | European Pat. Off. . |
| 0 377 601 | 10/1989 | European Pat. Off. . |
| 0 345 171 | 12/1989 | European Pat. Off. . |
| 0 414 915 A1 | 3/1991 | European Pat. Off. . |
| 0 462 836 | 12/1991 | European Pat. Off. . |
| 0 524 161 A1 | 1/1993 | European Pat. Off. . |
| 0 532 327 | 3/1993 | European Pat. Off. . |
| 2 676 738 | 11/1992 | France . |
| 91/04315 | 4/1991 | WIPO . |
| WO 91/04315 | 4/1991 | WIPO . |
| 92/07935 | 5/1992 | WIPO . |
| WO 93/02090 | 2/1993 | WIPO . |
| WO 94/04614 | 3/1994 | WIPO . |
| 95/10185 | 4/1995 | WIPO . |
| WO 95/31197 | 11/1995 | WIPO . |
| WO 96/09053 | 3/1996 | WIPO . |

OTHER PUBLICATIONS

Inoue et al, "Expression of a Hybrid Cu/Zn–type Superoxide . . . ," J. Bio. Chem., vol. 26,6 No. 25, pp. 16409–16414 (1991).

Day et al, "Manganic Porphyrins Posses Catalase Activity . . . ," Arch. Biochem. Biophys., vol. 347, No. 2, pp. 256–262 (1997).

Tsan, M–F., "Superoxide Dismutase and Pulmonary Oxygen Toxicity," XP–002074505, pp. 286–290.

Boissinot et al, "Rational Design and Expressionof A Heparin–Targeted Human Superoxide Dismutase", Biochemical and Biophysical Research Communication 190(1):250–256 (1993–.

Oury et al, "Cold–induced Brain Edema in Mice", The Journal of Biological Chemistry 268(21):15394–15398 (1993).

Oury et al, "Extracellular superoxide dismutase, nitric oxide, and central nervous system $O_2$ toxicity", Proc. Natl. Acad. Sci. USA 89:9715–9719 (1992).

Oury et al, "Establishment of Transgenic Mice Expressing Human Extracellular Superoxide Dismutase", American Review of Respiratory Disease 143(4):A515 (1991), International Conference Supplement Abstracts –No. 236.

Oury et al, "Transgenic Mice Superexpressing Human Extracellular Superoxide Dismutase Show Increased Resistance to Cold–induced Brain Edema, But are Mor Susceptible to Hyperbaric Oxgyen", American Review of Respiratory Disease 145(4):A713 (1992), International Conference Supplement Abstracts –No. 211.

(List continued on next page.)

*Primary Examiner*—Robert A. Wax
*Assistant Examiner*—Tekchand Saidha
*Attorney, Agent, or Firm*—Nixon & Vanderhye

[57] ABSTRACT

The present invention relates, in general, to a method of modulating physiological and pathological processes and, in particular, to a method of modulating intra- and extracellular levels of oxidants and thereby processes in which such oxidants are a participant. The invention also relates to compounds and compositions suitable for use in such methods.

14 Claims, 38 Drawing Sheets

OTHER PUBLICATIONS

Oury et al, "Immunocytochemical Localization of Extracellular Superoxide Dismutase in Human Lung", American Review of Respiratory Disease 147(4):A713 (1993) International Conference Supplement Abstracts –No. 246.

Oury, Tim D., "Extracellular Superoxide Dismutase and Nitric Oxide: Transgenic and Immunocytochemical Studies", Dissertation submiited in partial fulfillment of the requirements for the degree of Doctor of Philosophy in the Department of Pathology in the Graduate School of Duke University (Jun. 17, 1993).

Naruta et al. (1991). J. Am. Chem. Soc. 113:3595–3596, 1991.

Leondiadis et al. (1989). J. Org. Chem. 54: 6135–6138, 1989.

Stralin et al, "Effects of Oxidative Stress on Expression of Extracellular Superoxide Dismutase, CuZn–Superoxide Fibroblast", Biochem. J. 298:347–352 (1994).

Folz et al, "Extracellular Superoxide Dismutase (SOD3): Tissue–Specific Expression, Genomic Characterization, and Computer–Assisted Sequecne Analysis of the Human EC SOD Gene", Genomics 22:162–171 (1994).

Clyde et al, "Distributin of Manganese Superoxide Dismutase mRNA in Normal and Hyperoxic Rat Lung", American Journal of Respiratory Cell and Molecular Biology 8:530–537 (1993).

Wolberg et al, Electrcical and Electron Paramagnetic Resonance Studies of Metalloporphyrins and Thier Electrochemical Oxidation Products:, Journal of the American Chemcial Society 92(10):2982–2990 (1970).

Pasternack et al, "Superoxide Dismutase Activities of an Iron Porphyrin and Other Iron Complexes", Journal of the American Chemical Society 101(4):1026–1031 (1979).

Winkelman, James, "The Distribution of Tetraphenylporphinesulfonate in the Tumor–bearing Rat", Cancer Research 22:589–596 (162).

Moisy et al, "Catalytic Oxidation of 2,6–Terbutylphenol by Molecular Oxygen Elecroassisted by Poly(Pyrrole–Manganese–Porphyrin)", New J. Chem. 13:511–514 (1989).

Malinski et al, "Characterization of Conductive Polymeric Nickel(II) Tetrakis(3–methoxy–4–hydroxy–phenyl)Porphrin as an Anodic Material for Electrocatalysis", J. Electroche. Soc. 138(7):2008–2015 (1991).

Weinraub et al, "Chemical properties of water–soluble porphyrins. 5. Reactions of some manganese (III) porphyrins with the superoxide and other reducing radicals", Int. J. Radiat. Biol. 50(4):649–658 (1986) (Abs).

Fajer et al, "π–Cation Radicals and Dications of Metalloporphyrins", Journal of the American Chemical Society 92(11):3451–3459 (1970).

Pasternack et al, "Aggregation of Nickel(II), Coopwer (II), and Zinc(II) Derivatives of Water–Soluble Porphyrins", Inorganic Chemistry 12(11):2606–2610 (1973).

Datta–Gupta et al, "Synthetic Porphyrins. I. Synthesis and Spectra of Some para–Substituted meso–Tetraphenylporphines (1)", J. Heterocycl. Chem. 3:495–502 (1966).

Harriman et al, "Photochemistry of Manganese Porphyrins Part 2 –Photoreduction", pp. 1543–1552.

Longo et al, "The Synthesis and Som e Physical Properties of ms–Tetra(pentafluorophyenyl)–porphin and ms–Tetraphenylporphines(1)", Notes 6:927–931 (1969).

Barnitz et al, Reactions of $Fe^{III}$(meso–α, α, α–tetrakis[O–[N–methylisonicotinamido)phenyl]porphyrin)$^{5+}$and $Fe^{III}$(meso–tetrakis[N–methylpyridinium–4–yl]porphyrin)$^{5+}$ with NC; $Co_2$; and $O_2$", Inorg. Chem. 32:941–947 (1993).

Pasternack et al, "On the Aggregation of Meso–Substituted Water–Soluble Porphyrins", Journal of American Chemical Society 94(13):4511–4517 (1972).

Data–Gupta et al, "Synthetic Porphyrins II Preparation and Spectra of Some Metal Chelates of para", Journal of Substituted–mesa–Tetrapheynylporphines, Journal of Pharmaceutical Science 57(2):300–304 (1968).

Gosh, "Substituent Effects on Valence Ionization Potentials of Free Base Porphyrins: Local Density Functional Calculations and Their Relevance to Electrochemical and Photoelectron Spectroscopic Studies", J. Am. Chem. Soc. 117:4691–4699 (1995).

De Peretti et al, "Imidazol[2,1–b]benzoxazole–3–acetamide derivatives, their preparation, and their therapeutic use", Chemical Abstracts 121;1016, Abstract No. 121:200896u.

Oberley et al, "Anticancer activity of metal compounds with superoxide dismutase activity", Agents and Actions 15(5/6):535–538 (1984).

Collman et al, "Synthesis of Face to Face Porphyrin Dimers Linked by 5,15–Substituents: Potential Binuclear Multielectron Redox Catalysts", J. Am. Chem. Soc. 103:516–533 (1981).

Gassman et al, "Electronic Effects of Peripheral Sustitiuents in Porphyrins: X–ray Photoelctron Spectroscopy and ab Initio Self–Consistent Field Calculations", J. Am. Chem. Soc. 114:9990–10000 (1992).

Bishop et al, "The Reactin of Thiomides with Phosphorus Ylides", J. Org. Chem. 56:5079–5091 (1991).

Picker et al, "Cobalt(III) complexes of water soluble synthetic meso–substituted porphyrins as radiation sensitizers for oxic and hypoxic tumor cells", 8–Radiation 112:405 (1990) Abstract No. 112:73026d.

McCord et al, "Superoxide Dismutase–An Enzymic Function for Erythrocuprein", Biochemistry 492, p. 346.

McCord et al, "Superoxide Dismutase An Enzymic Function for Erythrocuprein (Hemocuprein)", The Journal of Biological Chemistry 244(22):6049–6055 (1969).

Crapo et al, "The Failure of Aeorsolized Superoxide Dismutase to Modify Pulmonary Oxygen Toxicity", American Review of Respiratory Disease 115:1027–1033 (1977).

Joester et al, "Superoxide Dismutase Activity of $Cu^{2+}$–Amino Acid Chelates", FEBS Letters 25(1):25–28 (197.

Brigelius et al, "Superoxide Dismutase Activity of Low Molecular Weight Cu2+–Chelates Studied by Pulse Radiolysis", FEBS Letters 47(1):72–75 (1974).

Sorenson, John R.J., "Copper Chelates as Possible Active Forms of the Antiarthritic Agents", Journal of Medicinal Chemistry 19(1):135–148 (1976).

deAlvare et al, Mechanism of Superoxide Anion Scavenging Reaction by Bis–(Salicylato)–Copper(II) COmpl Biochemical and Biophysical Research Communications 69(3):687–694 (1976).

Halliwell, Barry, "The Superoxide Dismutase Activity of Iron Complexes", FEBS Letters 56(1):34–38 (1975).

McClune et al, "Catalysis of Superoxide Dismutation by Iron–Ethylenediaminetetraacetic Acid Complexes Mechanism of the Reaction and Evidence for the Direct Formation of an Iron(III)–Ethylenediaminetetraaceti Acid Peroxo Complex from the Reaction of Superoxide with Iron (II)–Ethylenediaminetetraacetic Acid", Communications to the Editor, pp. 5220–5222 (1977).

Diguiseppi et al, "Putative Superoxide Dismutase Activity of Iron–EDTA: A Reexamination", Archives of Biochemistry and Biophysics 203(1):145–150 (1980).

Robertson, Jr. Et al, Does Copper–D–Penicillamine Catalyze the Dismutation of $O_2$?, Archives of Biochem and Biophysics 203(2):830–831 (1980).

Weerringloer et al, "The Integration of Divalent Copper and the Microsomal Electron Transport System", The Journal of Biological Chemistry 253(23):11839–11846 (1979).

Pasternack et al, "Catalyst of the Disproportionationof Superoxide by Metalloporphyrins", Journal of Inorg Biochemsitry 11:261–267 (1979).

Archibald et al, Manganese and Defenses against Oxygen Toxicity in *Lactobacillus plantarum,* Journal of Bacteriology 145(1):442–451 (1981).

Archibald et al, Manganese, Superoxide Dismutase, Oxygen Tolerance in Some Lactic Acid Bacteria, J of Bacteriology 146(3):928–936 (1981).

Archibald et al, The Scavenging of Superoxide Radical by Manganous Complex: In Vitro, Archives of Biochemistry and Biophysics 214(2):452–463 (1982).

Archibald et al, Investigations of the State of Manganese in *Lactobacillus plantarum,* Archives of Biochemsitry and Biophysics 215(2):589–596 (1982).

Darr et al, "A Mimic of Superoxide Dismutase Activity Based Upon Desferroioxamine B and Manganese(IV)", Archives of Biochemistry and Biophysics 258(2):351–355 (187).

Beyer et al, "Charcterization of a Superoxide Dismutase Mimic Prepared from Desferrioxamine and $MnO_2$, Superoixde Dismutase Activity", Archives of Biochemistry and Biophysics 310(2):341–346 (1994).

Faulkner et al, Characterization of Mn(III) Porphyrins Mimic Superoxide Dismutase in Vitro and Substitute for It in Vivo, The Journal of Biological Chemistry 269(38):23471–23476 (1995).

Liochev et al, "A Cationic Manganic Porphyrin Inhibits Uptake of Paraquat by *Escherichia coli*", Archives of Biochemistry and Biophysics 321(1):271–275 (1995).

Peretz et al, "Chemical properties of water–soluble porphyrins 3. The reactin of superoxide radicals with some metalloporphyrins", Int. J. Radiat. Biol. 42(4):449–456 (1982).

Baudry et al, "Salen–Manganese Complexes are Superoxide Dismutase–Mimics", Biochemical and Biophysical Research Communication 192(2):964–968 (1993).

Gonzalez et al, "EUK–8, a Synthetic Superoxide Dismutase and Catalase Mimic, Ameliorates Acute Lung Injury in Endotexemic Swine", Journal of Pharmacology and Experimental Therapeutics 275(2):798–806 (1995).

Deune et al, "Prevention of Ischemia–Reperfusion Injury with a Synthetic Metalloprotein Superoxide Dismutase Mimic, SC52608", Plastic and Reconstructive Surgery 98(4):711–718 (19996).

Lowe et al, "Comparison of the cardiovascular effects of two novel superoxide ismutase Mimetics, SC–55858 and SC–54417, in conscious dogs", European Journal of Pharmacoloty 304:81–86 (1996).

Weiss et al, "Manganese–based Superoxide Dismutase Mimetics Inhjibit Neutral Infiltration in Vivo", The Journal of Biological Chemistry 271(42):1939–1940 (1996).

Jin et al, "A new route to water soluble porphyrins: phosphonium anbd ammonium type cationic porphyrins an self–assembly", Chem. Commun., pp. 1939–1940 (1996).

Pitié et al, "Oxidation at Carbon–1' of DNA Deoxyriboses by the Mn–TMPyP/KHSO5 System Results from a Cytochrome P–450–Type Hydroxylation Reaction", J. Am. Chem. Soc. 117:2935–2936 (1995).

Libby et al, "Cationic Porphyrin Derivatives As Inhibitors of Polyamine Catabolism", Biochemical Pharmacol 50(9):1527–1530 (1995).

Llan et al, "Superoxide Dismuting Acitivity of an Iron Porphyrin", Inorg. Nucl. Chem. Letters 17(3/4):93–96 (1981).

Solomon et al, "Chemical properties of Water–Soluble Porphyrins. 2. The Reaction of Iron(III) Tetrakis (4–N methylpyridyl)porphyrin with the Superoxide Radical Dioxygen Couple", J. Phys. Chem. 86:1842–1849 (1982).

Weintraub et al, "Chemical Propeties of Water–Soluble Porphyrins. 1. Equilibria between Some Ligands a Iron(III) Tetrakis (4–N–methylpyridyl)porphyrin", J. Phys. Chem. 86:1839–1842 (1982).

Day et al, "A Metalloporphyrin Superoxide Dismutase Mimetic Protects Against Paraquat–Induced Endot Cell Injury, in Vitro", The Journal of Pharmacology and Experimental Therapeutics 275(3):1227–1232.

Kariya et al, "Superoxide Dismutase (SOD) Activity with Fe–chlorin e6–Na and Suppression of Malignant Growth in Rats", Cancer Biotherapy 10(2):139–145 (1995).

Liochev et al, A Cationic Manganic Porphyrin Inhibits Uptake of Paraquat by *Escherichia coli,* Archive Biochemistry and Biophysics 321(1):271–275 (1995).

Ohkawa et al, "Assay for Lipid Peroxides in Animal Tissues by Thiobarbituric Acid Reaction", Analytical Biochemistry 95:351 (1979).

Yue et al, "Carvedilol, a New Vasodilator and Beta Adrenoceptor Antagonist, is an Antioxidant and Free Radical Scavenger", The Journal of Pharmacology and Experimental Therapeutics 263:(1992).

Song et al, "Anti–HIV activities of anionic metalloporphyrins and related compounds", Antiviral Chemistry and Chemotherapy 8(2):85 (1996).

Harriman and Porter, "Photochemistry of Manganese Porphyrins", J. Chem. Soc. 275:1532–1542 (1979).

Bedioui et al, "Metalloporphyrin–Polypyrrole Film Electrode: Characterization and Catalytic Application", J. Electroanal. Chem. 207:87–99 (1986).

Foran et al, "Effect of Electrolyte Concentration on Axial Anion Ligation in Manganese(III) meso–Tetraphenylporphyrin Chlorides", Inorg. Chem. 31:1463–1470 (1992).

Milgrom, Facile Aerioal Oxidation of a Porphyrin. Part 3. Some Metal Complexes of meso–Tetrakis–(3, 5–di–t–butyl–4–hydroxyphenyl)porphyrin, J. Chem. Soc. Perkin Trans. 11:71–79 (1988).

Bockhorst and Hoehn–Berlage, "An Optimized Synthesis of Manganese meso–Tetra(4–sulfonato–phenyl)porphine: A Tumor–Selective MRI Contrast Agent", Tetrahedron 50(29):8657–8660 (1994).

Keinan et al, "Catalytic Antibodies. Circular Dichroism and UV–Vis Studies of Antibody–Metalloporphyrin Interactions", Inorg. Chem. 31:5433–5438 (1992).

Marx, "Role of Gene Defect in Heredity ALS Clarified", Science 261:986 (1993).

Epp et al, "Superoxide Dismutase Activity of Manganese Chelates", 76–78 (1986).

Bors et al, "An expanded function for superoxide dismutase", Chemical Abstracts 115:388 (1991), Abstract N 109185h.

Milogram et al, "Redox Behavoiur of Phenolic Porphyrins in Basic Solutions: A Reappraisal", Free Rad. Res. 24(1):19–29 (1996).

Szabo et al, "Evaluation of the relative contribution of nitric oxide and peroxynitrite to the suppression of mitochondrial respiration in immunostimulated macrophages using a manganese mesoporphyrinsuperoxide dismutase mimetic and peroxynitrite scavenger", FEBS Letters 381:82–86 (1996).

Patel et al, "Requirement for Superoxide in Excitotoxic Cell Death", Neuron 16:345–355 (1996).

Bamford et al, "The Squalestatins: Synthesis and Biological Activity of Some C3–Modified Analogues; Replacement of a Carboxylic Acid or Methyl Ester with an Isoelectric Heterocyclic Functionality", J. Med. Chem. 38:3502–3513 (1995).

Szabo et al, "Peroxynitrite Is Involved in the Pathogenesis of the Vascular Contractile and Energetic Failu Endotoxic Shock", Shock Society Meeting (1996).

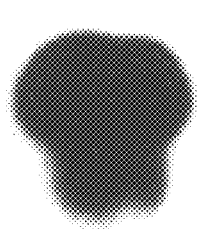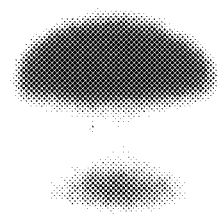
FIG. 13

FIG. 20A
RESTRICTION MAP
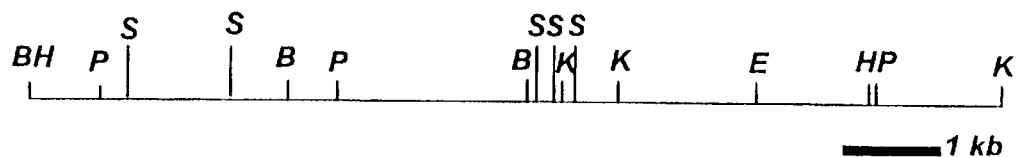
FIG. 20B
SEQUENCING STRATEGY
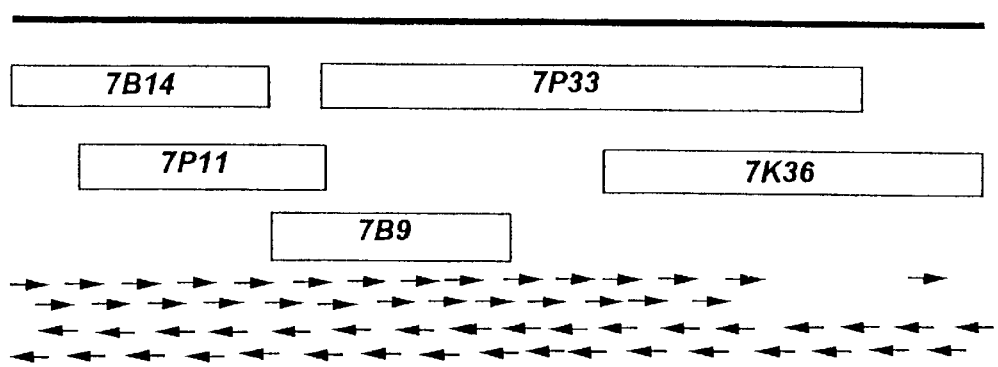
FIG. 20C GENE STRUCTURE
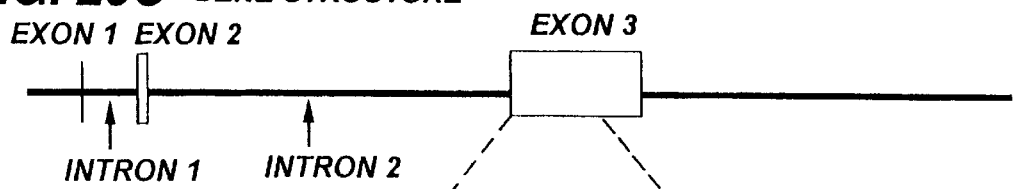
FIG. 20D
PROTEIN STRUCTURE
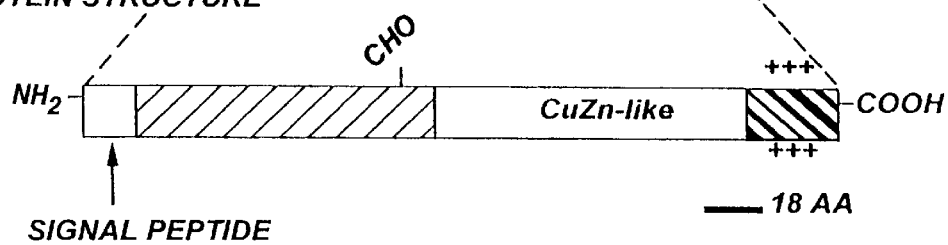

FIG. 24

```
GGATCCAGAG ATTTAGATTT TTTATAAGCT TTCCTGCCAC CGAAACGGGT GTTTGGGACC      60
TCACGAGGCC CTGTTCATTC TTCGTCGCTG CGCTCCCCAC TCTGTACTGG ATGCATTTAC     120
TGACGTTGTT GTCTCCGTCC CCAGAGTATG AACCCCAAG GTGACTCATG CAGCTGTGGG     180
TGCCCGGCAT ACAGCATGGT GACTGGAATG GATGAGCACC CAATAAACAT TTGTTGCAGG     240
AATGCAGGAG GACGGGCAGG CCAGCAAGCA GGCTGCCTGG TTTTTCCCAC ATGGGCTTTT     300
CTGGGAAAGA AGAGCTTCTA TTTTTGGAAA GGGCTGCTAT GATTGAGAAA AGTTCATGGC     360
AGCAAAAAAA GGACAGACGT CGGGAGGGAA ACACTCCTAG TTCTCCCAGA CAACACATTT     420
TTTAAAAAGA CTCCTTCATC TCTTTAATAA TAACGGTAAC GACAATGACA ATGATGATTA     480
CTTATGAGTG CGGCTAGTGC CAGCCACTGT GTTGTCACTG GGCGAGTAAT GATCTCATTG     540
GATCTTCACG GTGGGCGTGC GGGGTGGACA GCCTCACACC CCCATTTTAC AGATGATGAA     600
AAGGAGGTGC AGGGAGTGGT GCAGCTGCTT CAGGCGTACA CAGATAGGAA GTGACAAGGC     660
TGGGACTCTG CAGCCTGAGT GTGTCATCAC GACCCACCCG CTGCTCTGCT CTCATAGGTA     720
TGACAGCACA GCTCTGGAGC AAATGCCATG CACATTTGCA AGGTGCCCAT TTCCATGCAG     780
CAAAAATAAG TCAATAAGTT ATTGACTTAG AGAAAGCAA AGGGCCTCTC AATAAAGAGG     840
TCATTGTACA CCTCTCCAAA CAGGCGATTT TCTTTCTCAT TTTTATTCCC CTGCTGTGTG     900
CTGAAGGTCA CTGGCTACAA GCCGGTGAAG TCGCGGAATG GAATCCTTGG CCCGAAAACC     960
CAAAAATGGG AGGGGCAGAG GAGGTGGGGA CAGAGCGGGA GGAGGTGGAG GCGAAGCAAT    1020
TCTACAACCC GGGGAGGTCT GGCCTGCTTT TCCTCCCTGA ACTGGCCCAA TGACTGGCTC    1080
CCTCACGCTG ACCACTCCTC TGGGCTGGCC TCCTGCACTC GCGCTAACAG CCCAGCTCC     1140
AGGGACAGCC TGCGTTCCTG GGCTGGCTGG GTGCAGCTCT CTTTTCAGGA GAGAAAGCTC    1200
TCTTGGAGGA GCTGGAAAGG TGGGTGCTAA GTTGAGGTTC ATTTGTTCT TCTCGGAGTG    1260
TGCTTATTGA GTCTGAAGCT GGGTTGGGGC AACGGGCCTC TTCTTGGGAA CAAATTGGAT    1320
CATCTTCTTG GAAGGAAAT GTACTTTCCC TGGCTGCTCT GAGGGGTTAG TGGGGAGGTG    1380
GAGTGAGCGG GGAGGAAGGC AAGGAGGGGA GGAAGAAACC GTTCCTCCTG TGGATCTGCA    1440
AAGACCAGTC CAAGAGGATT TTAGTGTTAG GAAAAGGAAT CTGGAGTGAC GAGAAAGGGG    1500
GCCTTTCTAG ATGTTGCATG GCTTTGGTGT CGGGAGCCAC TTATGGGACA GCAGGTACTC    1560
TAAAAAGCCA CCTCCTTAGG AAAGCAGAGA GGCCCTGGCC AGCTCAGGCT CCCAGCAAGA    1620
GCTCCTTCTA GGAGACAGCT GAGGGATGAA ACACACCCAA GGCTCAAGAG GGGCAGGTTC    1680
TTCCCAGATA CAGACCCAGG AAGGAGATAA AGGCTTGGTG CCTCTATTTG GTTCAGGATA    1740
AGGGCCCCTG TCCTCTTTCT CTGATAACAC TGTCCTCTTT CTCTGATAAC ACCGTCCTCC    1800
CTTCCAGATC CACGTACAAA GGAGGCCCTT AAAAAGGCAC TTGGTCATTC ACAGCTCAAA    1860
CTGAGCAAGA GGCTGTGGGA GAAGAATCAA GTTGGTCCCG AGGGGAAGAG GTGTCAAAGG    1920
CTTAAGAAAC AAGAAGTCAG AGTTTACCTG GGTTTGAGGG AGAATTTTCT TTCCCCCTTT    1980
```

FIG. 24-1

```
TCCTCCTCCT CCTCCTTCTT CTCTTTTTTT TTTTTTTTTT TTTTTTTTTT TTGAGACATG   2040
GTCTCATTCT GTCACCCAGC ACCCAGGCTG AATGTAGTG GCACGATCAC TATCACGGCT    2100
CACTACAGCC TCTACCTCCC GGGCTCAAGT GATCCTCCTA CCTCAGCCTC CTGAGTAACT   2160
GGGACTACAG GCACATGCCA CCACACCCAG CTATTTTTTT TTTTGCTAGA GATGGGGGTC   2220
TCTACCAGGT TGGTCTCATA CTCTTGTACT CAAATGATTC TCCTGTCTCA TCCTCCCAAA   2280
GGGTGGGATT ACAGGCATAA GCCACCATGC CTGGCTCTTC TTTTGGTTTC AGAGAAAAAC   2340
ATCTCCTTAA AATGTTTATT TCCCAAGGAT TCTTGAAAAA GAAAGCTCAC TGACACACCC   2400
AAAACAATCT GGTTTTGCTC TGTGCTTTTA GGAGAACTT TCTAAGCAGC AGAGCCCTTC    2460
TGAGTGGCAG GGCTGTCTTA GGAGGAAGGT GTCTTTTGAT GATGGGGAAC TTCATGTCCA   2520
GGTCTGGCAG GAGAGTTACC CCACTTTCCT GCCTACTCCC TGGGGCTTTG GGTAGTAGT   2580
ACCACATTGG GCCATGTCAT TTAGGTGAGT CCTTCAACAT CACTTTCTCT GCTTCTCCCT   2640
CTTTCTGGAT CCTCCTTCTT GGAGCCTTTC AAGGGGACCT CCTCTCACAG TGTCCATAGC   2700
ATCTCTTAGC TAATGGTCCT TAAAATCTCT ACCAGCAGCT TCTCTCTGAT AGCTAAGAGC   2760
TGCCATTTAC TGGGAACTTT CTATGTACTG GGCTCTGTGC TAAGTGCCCT AGATGAGAGA   2820
TGTGCAGTGT GGTGCCTAAA CCTTGGGCTT GGAGCAGACA CACACTTTCA AATCCTGCCT   2880
TCAGCTCCTT AGTGAACATG TCACCTTGGG CGGGACACAC GCCTCTCTGT GCCTCAGTTT   2940
CCTACACTTT AGAATGGGGA TAACACTGAA TAATGTTCTT GTGAGGATGC AGGGAATTAA   3000
CCCACGCACA GTACTTATAA TAGTGTCTGG CGCCTGTGTT CGATAAGTTT TAGCAATTCT   3060
AATCATCTCT TTTAAGCCTC GCAGCAAGCC TCTAAGGTAA GTCTGTATTA GTATCCCTAT   3120
TTACAGATGA GAAAACTGAG GTTCACAGGG GATGAGACAG TGTACAGTCT GCAGTCCAGC   3180
AATTACTCTG CTACTCAGCA ATAAAAATAG TAACAGCTAA CCCTTAGACT AAGTGGCAGA   3240
GTCAGGCTTT AGATTCATGA GGTGAGTTCT GGAATCCATC CCTTTAATAA CCACACTAAA   3300
TTGCCTTTCT GAAATGGTTA TATAAAGCAT ATCTACCCAA TCTTGGAGTT TTTTAAATGG   3360
CACCTAGTTT GGTGCTGGAA ATGCAGTTGA CCTTCAAAGC AATTCTTTGG AGGCAGCATC   3420
AATCCCTCTG GAAATACCTC GGTGGCATGG CTGGCCTTAT TCTACAGGTA AGGAACTTGA   3480
AGCTAAGCAT CAGTAACCCC GTGAAGTCAC AGTTAGTATA GGTTGGAATT GGGATTCAAA   3540
TCTGTACCTG ACTTTATAAT TCCTAGCTGG GCCCCAGAAT CTTTGATAGA GGTGTCTTCT   3600
TTCTTTTCTT TTCTTTCTTT CCTCTTTCTT TCCCTTCCTT CCTCTCTCTC TGTCTTTCTT   3660
CTCTCCTTTC TTTCTCACAG AATCAAAATC TCTTGGGGTG GGGCCTGGGC ATCTGATTTT   3720
TAAAAACCAG ACATCTGATG TGCAGTCAAC ACTGAGAACC CCTGCCAGCT TCATCTCCTC   3780
TTCTAAGTGC CAGACCCAAG TTTCCAACTG TCTGCCCACC TGTCTCCCCA CCTGGGCACC   3840
CGCCAGCGTC TCACCCTCAG GAGACTCCAG CTGAACTAAT CCTCTCTCCC TGCTTTTCCA   3900
GAACAGGTCC CACCCTCCCT CCACTCAGTC TCTCCTGCTG GGAACCCTGG TCATCTGCAC   3960
```

FIG. 24-2

```
TGTGCCTTCA TCTTCCATCC TGCCAGTGCT GCCCGGTGTG TCTCTTAAAC CCATGCCTCC    4020
TCTGTGTGCA CCACCTGCAC TTTGGTAAAA GCCTTCATTT CCTGCTTGGG TTACTACAAC    4080
GCCCCCTAAC TCATCTCACT GTCTCTATTT CTGCTTCTCT GTCTCTCCCT AGGCTACTCC    4140
CATTCTTCCT CCCCTTTCCT CTTCATCCCA AGTCCAACC CATATCCTTT TACCAGTAGG     4200
ACTTAAGGAA CTAAAGACTA TCTCATCACC CACTTTTCTT CTTAAAAACT TCCACTGCAC    4260
TGCCTGCTGA GATGGCCTTC CTACCCAACT TGGCTGGAAA ACTCCTACCC ATCTTGTGGA    4320
ACCCAGTTCA AAAGTCACCA CCTCTGAGAA GCCTTCCCTG AGGCTCCTAG GGAGATGGGT    4380
ACTGCCTCCT CTGTCCTTCT CCAGCACAGG CCCCATCTTC AATCACAGGA TTGTGCTGGA    4440
ATGATTGGAT GCCAAGTCTG TCCCTCACTG AACTCCTTAT GCAAAATCCA TATTATATGT    4500
TTCCTTTTGC CAGGTGTGGG CCCAGGTGCT GGGGATACCG ATGAATAAAA CTGAGTTTCT    4560
GTCTTCAAGA AGCTCCAAGT CTACTGAGTG TAGCAGAGAA CAGGGAGAAG GCACTTCAGG    4620
GAGAAGGGGT AGCACATGCA AAGCCCCAGA AGGCAGGGAC AGAAGCCTTA GGGATGTCTG    4680
TGGGGGAGGA TGGAGGAAGA GGGTAACAGG AGACCAGGTG GGGAGATGAG GGAGGTGGTC    4740
TGGAAGGGCC ATGAGACACC CCTCACGCTC CCTGAGACCC CCTCCACGCT ATAGAGATGG    4800
GACTGGAGAG GACGATGATC ATTTGTGACT CAGATCCCTG TGGGTTTCTT CAGATTGGGT    4860
CTCACCCATC TTTACAGCCA CAGCACCTAA CACAGTGCCC GGCACACAGC AGGCCCTAGA    4920
CAAACGTTTG CCACATGAAG TCATGCCACT GGCCAGGAAG CCCACTGGGG ACTGGGGGT     4980
TGGTTCTGCG ATAATGGGGT CCCTGAGATT CTATGTTTCA CGTGACTAAG CCTCACTCTG    5040
CCCCCACCTC CGCGGGGGCG TCCCGCAGGT GCCCGACTCC AGCC ATG CTG GCG CTA    5096
                                               Met Leu Ala Leu
                                                1
CTG TGT TCC TGC CTG CTC CTG GCA GCC GGT GCC TCG GAC GCC TGG ACG     5144
Leu Cys Ser Cys Leu Leu Leu Ala Ala Gly Ala Ser Asp Ala Trp Thr
 5              10                  15                  20
GGC GAG GAC TCG GCG GAG CCC AAC TCT GAC TCG GCG GAG TGG ATC CGA     5192
Gly Glu Asp Ser Ala Glu Pro Asn Ser Asp Ser Ala Glu Trp Ile Arg
             25                  30                  35
GAC ATG TAC GCC AAG GTC ACG GAG ATC TGG CAG GAG GTC ATG CAG CGG     5240
Asp Met Tyr Ala Lys Val Thr Glu Ile Trp Gln Glu Val Met Gln Arg
         40                  45                  50
CGG GAC GAC GAC GGC ACG CTC CAC GCC GCC TGC CAG GTG CAG CCG TCG     5288
Arg Asp Asp Asp Gly Thr Leu His Ala Ala Cys Gln Val Gln Pro Ser
     55                  60                  65
GCC ACG CTG GAC GCC GCG CAG CCC CGG GTG ACC GGC GTC GTC CTC TTC     5336
Ala Thr Leu Asp Ala Ala Gln Pro Arg Val Thr Gly Val Val Leu Phe
 70                  75                  80
CGG CAG CTT GCG CCC CGC GCC AAG CTC GAC GCC TTC TTC GCC CTG GAG     5384
Arg Gln Leu Ala Pro Arg Ala Lys Leu Asp Ala Phe Phe Ala Leu Glu
 85              90                  95                  100
GGC TTC CCG ACC GAG CCG AAC AGC TCC AGC CGC GCC ATC CAC GTG CAC     5432
Gly Phe Pro Thr Glu Pro Asn Ser Ser Ser Arg Ala Ile His Val His
```

FIG. 24-3

| | |
|---|---|
| Gly Phe Pro Thr Glu Pro Asn Ser Ser Arg Ala Ile His Val His<br>105 110 115 | |
| CAG TTC GGG GAC CTG AGC CAG GGC TGC GAG TCC ACC GGG CCC CAC TAC<br>Gln Phe Gly Asp Leu Ser Gln Gly Cys Glu Ser Thr Gly Pro His Tyr<br>120 125 130 | 5480 |
| AAC CCG CTG GCC GTG CCG CAC CCG CAG CAC CCG GGC GAC TTC GGC AAC<br>Asn Pro Leu Ala Val Pro His Pro Gln His Pro Gly Asp Phe Gly Asn<br>135 140 145 | 5528 |
| TTC GCG GTC CGC GAC GGC AGC CTC TGG AGG TAC CGC GCC GGC CTG GCC<br>Phe Ala Val Arg Asp Gly Ser Leu Trp Arg Tyr Arg Ala Gly Leu Ala<br>150 155 160 | 5576 |
| GCC TCG CTC GCG GGC CCG CAC TCC ATC GTG GGC CGG GCC GTG GTC GTC<br>Ala Ser Leu Ala Gly Pro His Ser Ile Val Gly Arg Ala Val Val Val<br>165 170 175 180 | 5624 |
| CAC GCT GGC GAG GAC GAC CTG GGC CGC GGC GGC AAC CAG GCC AGC GTG<br>His Ala Gly Glu Asp Asp Leu Gly Arg Gly Gly Asn Gln Ala Ser Val<br>185 190 195 | 5672 |
| GAG AAC GGG AAC GCG GGC CGG CGG CTG GCC TGC TGC GTG GTG GGC GTG<br>Glu Asn Gly Asn Ala Gly Arg Arg Leu Ala Cys Cys Val Val Gly Val<br>200 205 210 | 5720 |
| TGC GGG CCC GGG CTC TGG GAG CGC CAG GCG CGG GAG CAC TCA GAG CGC<br>Cys Gly Pro Gly Leu Trp Glu Arg Gln Ala Arg Glu His Ser Glu Arg<br>215 220 225 | 5768 |
| AAG AAG CGG CGG CGC GAG AGC GAG TGC AAG GCC GCC T GAGCGCGGCC<br>Lys Lys Arg Arg Arg Glu Ser Glu Cys Lys Ala Ala<br>230 235 240 | 5815 |
| CCCACCCGGC GGCGGCCAGG GACCCCCGAG GCCCCCTCT GCCTTTGAGC TTCTCCTCTG | 5875 |
| CTCCAACAGA CACCTTCCAC TCTGAGGTCT CACCTTCGCC TCTGCTGAAG TCTCCCCGCA | 5935 |
| GCCCTCTCCA CCCAGAGGTC TCCCTATACC GAGACCCACC ATCCTTCCAT CCTGAGGACC | 5995 |
| GCCCCAACCC TCGGAGCCCC CCACTCAGTA GGTCTGAAGG CCTCCATTTG TACCGAAACA | 6055 |
| CCCCGCTCAC GCTGACAGCC TCCTAGGCTC CCTGAGGTAC CTTTCCACCC AGACCCTCCT | 6115 |
| TCCCCACCCC ATAAGCCCTG AGACTCCCGC CTTTGACCTG ACGATCTTCC CCCTTCCCGC | 6175 |
| CTTCAGGTTC CTCCTAGGCG CTCAGAGGCC GCTCTGGGGG GTTGCCTCGA GTCCCCCCAC | 6235 |
| CCCTCCCCAC CCACCACCGC TCCCGCGGCA AGCCAGCCCG TGCAACGGAA GCCAGGCCAA | 6295 |
| CTGCCCCGCG TCTTCAGCTG TTTCGCATCC ACCGCCACCC CACTGAGAGC TGCTCCTTTG | 6355 |
| GGGGAATGTT TGGCAACCTT TGTGTTACAG ATTAAAAATT CAGCAATTCA GTACTGCGTC | 6415 |
| GAGGTCTTGG TTACTTTTTT GTTTGTTTGT TTTAGGCTTC TCTCCCAAGC TGAGCTTTTT | 6475 |
| TTTGTTTTGT TTTCGTTTTC CTTTTTTTTC TTTTTTTTGG GAGTGGCAAA CATGCTTCCC | 6535 |
| AAATCCCTAC AGGACTTCTC CTTATCCTCT GCCCCACCT CCCTAACCCT GCTGGCAACA | 6595 |
| ACGTTCAGCC ACTGCTTGTC TTGCCCTTCA GTGTGGCTCC AAGAGGAAGA TCACCAGAAT | 6655 |
| CACTCAGGGA AGTTAAAAAA AAAAATACAG CTTCCTGGGC TACATCCCAG AGCTGTGGAA | 6715 |

FIG. 24-4

```
TCCAAAGGGA GAAGAGAAAG TGAATTTGCG ACAAGCGTCG GGATGATTCT GGCACTGGAC    6775
CCTCTGGCCT GAGAGGGGAA GAGGCCTTCC ATCTCACCTG GCTGGTAGC  TTGTCACATC    6835
TGCCTCCGAG TACAGCCTTA GGTCCATTTC CCAGATATCA GAGACAGTGC CAGGGAAGCC    6895
AGGTGACTGC ATCTTGCCTA GGCACAGAAG AGTAGGGTTG GAATGTGACG TTGTTAGCAT    6955
TTGGCAGGAC CAAAACCAGA GGCAAACGGA GGCAGTGGGA TGGAAAGGCA GTTGATTTTG    7015
ATGAAGGCTT GTTGGGAGTT CAGCTTTCTT TTGAAACTTA TAATCTATAC CCAGGCTAGA    7075
ACAGTCTTGT GTATACACCT TCATTCATGG AATAAACGTA CTTGCAATAA CTTTTTAGCC    7135
TCCCAGGGTA GCCTCACTTC CTAGCTGTGA CTTTTCCACC CTGGTTACTG GGAGGCAGCT    7195
TCCATTTCTC CCAGACTAGC TAGGCAGTGC GTCCAACTGA ACCGCAGCCA GAAACCTGTC    7255
TCCAGGGGTT ATTTTTACCT CTAACTAGGA CTAACTTATT TTAAAATCTT CCTTGAGCC     7315
CAAGTGACAA CTGAAGAGAA AGGCTATTGC CTGGTGATTT TGCTCCACCA GTTGGTTCTC    7375
ACTGGTTTGA ATACTAACTT GAACTGTACT CATCGACACT GAAAGGGGAT GAGCAAACAG    7435
TGTCTCTAAA TCTCCTGATC CTGATCTCAA ATATCCCCCT AATTACAAGT GCAACAAGG     7495
CAGCTATTAC ACGGGACAC  AGGATGGAGA GGATGGGTGC CAAACACCCA TCGTCTACTC    7555
TGCTGCCTCG GTTATGGTGA ATTCAGGACC ATCAAGGGAG GTGTGGACCT TTTTTTTCAG    7615
AAGGAGGCTG ACACTTCTTG TCAATTGCAT TGTGTTCTTA GTTTGCTCT  TCACAACCCT    7675
TGACCCCGTA GATGGGGGCT GAAGAGGCAC CCTGGCCGAC TCACTCTATT TCTGTTTTGG    7735
GAATGGGATG GATAAACTAT CCCATGGCCT CCAGAGCCAA AAACCAAAA  CGAAACAAAA    7795
CAAAAAACCC CAAAACAAAA AAGCAAAAAG CAAACAAGAA AAAAAAAAA  AGAGGAAATA    7855
ATAGGCAGAC AATTTACAGT TCATTGTAAG GGCAAAGATA TGCATATAGC ATGATGGTTA    7915
ACAGGTCAGG CTCAGGTAGA AAGGCCCATT TGAACCCCAG CTCTGCCACA CTCAGAAACT    7975
GTGTGACCCG AACAAGTCAC TTAACCTCTC TGAGCATAGG TAAAATAAGA TCATCATACC    8035
AGATTGTTTT GAAGATTAAA TCAAGTGTTA TTCACGAGAG GTGCACAGCA TAGCATGCAC    8095
AACAAATAAG GACCTGGTAA GTATCTAATT AATAACAATG GCTAAGATCC AAAAAACAGC    8155
TACCTACTAA TAAATAGATG GGGCTGCCTT GTAAGGCAGT GAGCATCATG CAACCAGGAT    8215
TCAAATGAAG GACAGTTGCT ACCTCTGAGG TTCCCGAGAA GGATTTCTCG ATCCATTGAG    8275
AGACTGAATG ACATGAACTC TGCGATCCCA TCTCTTGTGG GGAGGGAACC TAGAATGAAG    8335
GGAAGATTGT GGGCCATAAA GGCAGACATC TGGTTCCTGG GCACAGAACC ATATGTGTGC    8395
CACCAAAGCC ACCCACCGGA CCCCACTTGG CCCCTGGAGT CTATTTTTAC TCCTCTCATC    8455
TTACAAGATC TATTTTGTTA ATCTCCTTAT ATTTGCTGTT TTGACTTCCC AGCCAGCTTG    8515
CTAATCAGTT TGCCTATTTG ACTCACAGGG TTTGCATTTG TCACGGGGAC TGAAACACAC    8575
GCTTGTTTTG ATTTCTTTTT GTAAATTAGA AGCGTTGATG TAATGACTCT ACCTAGACAC    8635
AGCTGGTAAA GTGAGAATAA TGCTCAAGTT TGCACAGTTT AAACACAATG TAGACAATAA    8695
```

FIG. 24-5

| | | | | | | |
|---|---|---|---|---|---|---|
| TTAGAAATGC | TATCTTTAGA | TGTTTAGGAT | AAGCTTTTCT | CAGAATTGCA | CTGATTTTTT | 8755 |
| TTTTCTGAGT | GGGGCTTTTT | AGTGCATATA | TACAGAAATA | CTAAAAACGT | AAGAAAATAG | 8815 |
| AGCAAATCAG | TGAGTGCTTT | GGTCAACTTG | AAAGACTGCA | GGAAATAAAC | CAACTGATTT | 8875 |
| TAGATCTGCC | TTTTTTTGAC | TGAATGCATA | AAATCTTTAC | ATTCTCCATA | TTTTTCATGA | 8935 |
| CTACCATATG | ATCAAATAGT | TTTAGGTGAC | AGATTGCAAC | TGATAAGTTG | CTGCAATATG | 8995 |
| GCAGAAGTCA | TGCTCAGCCT | CCGCTTGCCC | GGTGGTGAGG | GTGGAATATG | AAGCAAACAA | 9055 |
| TAAAGATAAT | TCATCATCTC | TATCAGGAAA | ATTGCCACAT | GTTTATTTCA | GGTAACAAAA | 9115 |
| AAGATATAGT | TATGATATAC | AATGACCATA | GAATCCAATA | AGCAACTTC | TGCAAATGAA | 9175 |
| TAGAAGGTAC | TTTTTCTTTA | AATGAAACTA | CAAAATAGCA | GCTGGTTTTA | AAAACAAAGC | 9235 |
| CAATTGTTTT | AGATTTAATA | GGCTACCACT | GGCCTCTGCT | AAGATCCCCA | AATATATTCC | 9295 |
| TGAGCTCACA | TAGATTCCAG | AAAGTCAAAC | TTTTCAATAT | TATGCAAACT | TTCCCTATGC | 9355 |
| ATCCAAAAAA | TTCTCATTTA | GTAAGAGGT | GATATGAAAT | GTAAGGCAGC | ATGTCCATAT | 9415 |
| CTATCATTTT | AAATTGCCTT | CATGCTGTAT | CAACTGGTTT | TGTTTTGGGA | AGCAACCATA | 9475 |
| ATATTGAGAG | ACGGGTCTTT | CCTATTTTTT | CTGCTACTCA | TTTCTAACTA | GATTCACTAC | 9535 |
| GGAGCTCCCA | ATTGCATCTC | TCTGATCTAC | AAATTTTTCT | CTCTTCAGGA | AGACACCTGG | 9595 |
| AAAGAAGGGA | CTACATTAAA | GGAGTGTGTT | GGGGGCAATG | CTTTGGCCTT | TTGACATCCT | 9655 |
| ATCTAGTCTG | AAGGGACCCT | CACTATTGCT | AAGGAGGAGG | AGTGTTTTAA | ATGGAGGCTT | 9715 |
| CAGAATGAAA | GCAGAGGAAG | AAGGTACTCT | CTTTTTCAAA | AGAAGGAGG | GTACAGGCCG | 9775 |
| GGCGCAGCTG | TCACGCCTGC | AATCCCAGCA | CTTTGGGAGG | CCGAGGAAGG | CAGATCACGA | 9835 |
| GGTTGGGAGT | TTGAGCCAGC | CTGGTCAACA | TAGTGAAACC | CCGTCTCTAC | TAAAAATACA | 9895 |
| AAAATTAGCC | AGCATGGTGG | TGCATGCCTG | TAGTCCCAGT | TACTCGGGAG | GCTGAGGCAG | 9955 |
| GAGAATCGCT | TGAACTCGGG | AAGTGGAGGT | TGCAGTGAGC | CGAGATCATG | CCACTGCACT | 10015 |
| CCACCCTGGG | TGACAGAGTG | AGACTCTCAA | AAAAAAAAA | AAAAAAAAA | AGAAGTAGGG | 10075 |
| TACC | | | | | | 10079 |

OXIDANT SCAVENGERS

This is a continuation-in-part of application Ser. No. 08/322,766, filed Oct. 13, 1994, now abandoned which is a CIP Ser. No. 08/136,207, filed Oct. 15, 1993, now abandoned.

This invention was made with Government support under Grant Nos. RO1 HL42609 and PO1 H31992 awarded by the National Institutes of Health. The Government has certain rights in the invention.

TECHNICAL FIELD

The present invention relates, in general, to a method of modulating physiological and pathological processes and, in particular, to a method of modulating intra- and extracellular levels of oxidants such as superoxide radicals and hydrogen peroxide and thereby processes in which such radicals are a participant. The invention also relates to compounds and compositions suitable for use in such methods.

BACKGROUND

Oxidants are produced as part of the normal metabolism of all cells but also are an important component of the pathogenesis of many disease processes. Reactive oxygen species, for example, are critical elements of the pathogenesis of diseases of the lung, the central nervous system and skeletal muscle. Oxygen free radicals also play a role in modulating the effects of nitric oxide (NO.). In this context, they (contribute to the pathogenesis of vascular disorders, inflammatory diseases and the aging process.

A critical balance of defensive enzymes against oxidants is required to maintain normal cell and organ function. Superoxide dismutases (SODs), a family of metalloenzymes which catalyze the intra- and extracellular conversion of $O_2^-$ into $H_2O_2$ plus $O_2$, and represent the first line of defense against the detrimental effects of superoxide radicals. Mammals produce three distinct SODs. One is a dimeric copper- and zinc-containing enzyme (CuZn SOD) found in the cytosol of all cells. A second is a tetrameric manganese-containing SOD (Mn SOD) found within mitochondria, and the third is a tetrameric, glycosylated, copper- and zinc-containing enzyme (EC-SOD) found in the extracellular fluids and bound to the extracellular matrix. Several other important antioxidant enzymes are known to exist within cells, including catalase and glutathione peroxidase. While extracellular fluids and the extracellular matrix contain only small amounts of these enzymes, other extracellular antioxidants are known to exist, including radical scavengers and inhibitors of lipid peroxidation, such as ascorbic acid, uric acid, and α-tocopherol (Halliwell et al, Arch. Biochem. Biophys. 280:1 (1990)). The relative lack of extracellular antioxidant enzymes may reflect the possible function of extracellular reactive oxygen species as bioeffector molecules (Halliwell et al, Arch. Biochem. Biophys. 280:1 (1990)). The relative deficiency of such enzymes may also result in greater susceptibility to extracellular oxidant stresses.

The enzyme EC-SOD, in many extracellular locations, exists only at low concentrations. While its physiologic role in vivo is yet to be defined, in many extracellular locations, EC-SOD is not thought: to function as a bulk scavenger of $O_2^-$. As indicated above, EC-SOD is a tetrameric Cu/Zn-containing glycoprotein with a subunit molecular weight of 30,000 (Marklund, Proc. Natl. Acad. Sci. U.S.A. 79:7634 (1982); Tibell et al, Proc. Natl. Acad. Sci. U.S.A. 84:6634 (1987); see also U.S. Pat. No. 5,130,245 and WO 91/04315). Biochemical data suggest that EC-SOD binds to heparan sulfate proteoglycans on endothelial cells, where it has been speculated to serve as a "protective coat" (Marklund, J. Clin. Invest. 74:1398 (1984); Karlsson et al, Biochem. J. 255:223 (1988)). Endothelial cells secrete both $O_2^-$ (Halliwell, Free Radical Res. Commun. 5:315 (1989)) and endothelium-derived relaxing factor, putatively identified as nitric oxide (NO.) (Noak and Murphy, in Oxidative Stress Oxidants and Antioxidants, eds Sies, H. (Academic, San Diego), pp. 445–489 (1991)). NO. functions as a vasoregulator and as a regulator of neurotransmission (Schuman and Madison, Science 254:1503 (1991)). NO. can, however, be toxic to neurons in some situations (Dawson et al, Proc. Natl. Acad. Sci. U.S.A. 88:6368 (1991)). $O_2^-$ is known to inactivate NO.-induced vasorelaxation (Gryglewski et al, Nature 320:454 (1986); Rubanyi and Vanhoutte, Am. J. Physiol. 250:H822 (1986); Rubanyi and Vanhoutte, Am. J. Physiol. 250:H815 (1986); Bult et al, Br. J. Pharmacol. 95:1308 (1988); Nucci et al, Proc. Natl. Acad. Sci. U.S.A. 85:2334 (1988)). Thus, a possible function for EC-SOD is to protect NO. released from cells from $O_2^-$ mediated inactivation.

The reaction of $O_2^-$ with NO. is also known to produce a potentially toxic intermediate in the form of the peroxynitrite anion ($ONOO^-$) (Beckman et al, Proc. Natl. Acad. Sci. U.S.A. 87:1620 (1990); Mulligan et al, Proc. Natl. Acad. Sci. U.S.A. 88:6338 (1991); Hogg et al, Biochem. J. 281:419 (1992); Matheis et al, Am. J. Physiol. 262:H616 (1992)). Thus EC-SOD may also function to prevent the formation of $ONOO^-$.

Surprisingly, it has been found that EC-SOD increases, rather than decreases, central nervous system $O_2$ toxicity and that this effect of EC-SOD occurs through modulation of NO.. This result implicates NO. as an important mediator in $O_2$ toxicity. The invention thus relates to methods of manipulating nitric oxide function that involve the use of extracellular antioxidants.

In addition to superoxide radicals, hydrogen peroxide is an oxidant species that is produced under a wide variety of conditions of oxidant stress. The invention thus also provides a method of manipulating hydrogen peroxide levels.

The methods of the invention find application in various disease and non-disease states in which oxidative stress plays a role, including inflammation. In a broader sense, the invention relates generally to methods of modulating intra- and extracellular processes in which an oxidant such as $O_2^{31}$, or hydrogen peroxide is a participant.

SUMMARY OF THE INVENTION

The present invention relates to a method of modulating intra- or extracellular levels of oxidants such as superoxide radicals and hydrogen peroxide. More particularly, the invention relates to a method of modulating normal or pathological processes involving superoxide radicals or hydrogen peroxide using low molecular weight antioxidants, for example, mimetics of SOD, catalase or peroxidase.

In one embodiment, the present invention relates to an oxidant scavenger, for example, a mimetic of superoxide dismutase, catalase or peroxidase, comprising a nitrogen-containing macrocyclic moiety and a cell surface or extracellular matrix targeting moiety, or a pharmaceutically acceptable salt thereof.

In another embodiment, the present invention relates to oxidant scavenger of the formula:

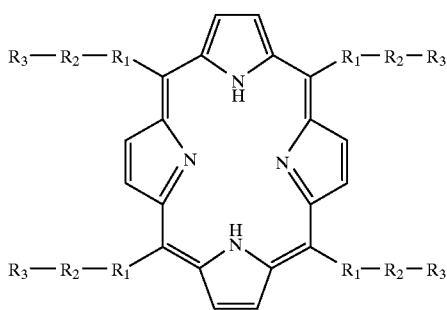

or a pharmaceutically acceptable salt thereof, wherein:

R₁ is a bond,

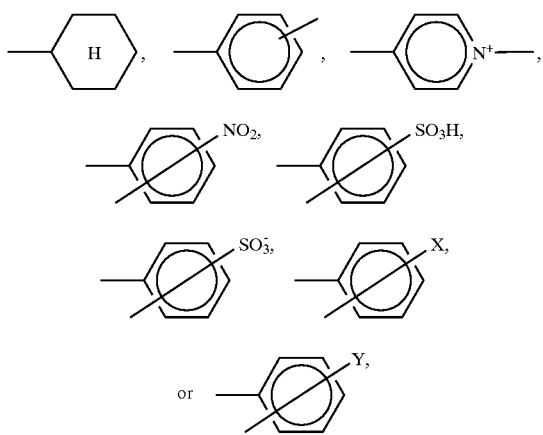

or wherein X is a halogen and Y is an alkyl group and wherein

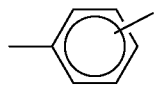

indicates bonding to R₂ at any position and

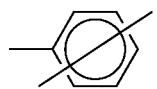

indicates bonding to R₂ and the substituent at any position; and

R₂ is a bond, $-(CY'_2)_n^-$, $-(CY'_2-CY'=CY')_n^-$, $-(CY'_2-CY'_2-CH=CH)_n^-$, $-(CY'=CY')_n^-$, or

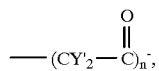

wherein Y' is hydrogen or an alkyl group and wherein n is 1 to 8; and

R₃ is $-Y''$, $-OH$, $-NH_2$, $-N^+(Y'')_3$, $-COOH$, $-COO^-$, $-SO_3H$, $-SO_3^-$, $-C-PO_3H_2$ or $-C-PO_3H^-$, wherein Y'' is an alkyl group, wherein, when R₁ is

and R₂ is a bond, R₃ is not Y'', and wherein, when R₁ is

and R₂ is a bond, R₃ is not $-Y''$, $-N^+(Y'')_3$, or COOH.

In a further embodiment, the present invention relates to a method of protecting cells from superoxide radical- or hydrogen peroxide-induced toxicity comprising contacting the cells with an oxidant scavenger, eg a SOD, catalase or peroxidase mimetic, sufficient to effect the protection.

In another embodiment, the present invention relates to a method of inhibiting damage due to oxidation of a substance with the subsequent formation of $O_2^-$ or hydrogen peroxide comprising contacting to the substance with an amount of a SOD mimetic sufficient to effect the inhibition.

In a further embodiment, the present invention relates to a method of inhibiting xanthine oxidase activity of a cell or tissue comprising contacting the cell or tissue with an amount of a SOD sufficient to effect the inhibition.

In another embodiment, the present invention relates to a method of treating a pathological condition of a patient (eg, of the lungs of a patient) resulting from superoxide radical-induced degradation of NO.. The method comprises administering to the patient (eg, to the airways of the patient) an effective amount of a compound having the activity and tissue specificity of SOD (eg EC-SOD) under conditions such that the treatment is effected.

In a further embodiment, the present invention relates to a method of treating an inflammatory condition in a patient in need of such treatment comprising administering to the patient an effective amount of an oxidant scavenger, eg a mimetic of SOD, (eg EC-SOD), catalase or peroxidase, under conditions such that the treatment is effected.

In another embodiment, the present invention relates to a method of treating a disorder resulting from aberrant smooth muscle function in a patient in need of such treatment comprising administering to the patient an effective amount of a mimetic of SOD (eg EC-SOD) under conditions such that the treatment is effected.

In yet a further embodiment, the present invention relates to soluble oxidant scavengers, for example, mimetics of SOD, catalase or peroxidase, and to targeted forms thereof, in particular, mimetics of EC-SOD having a GAG binding moiety attached thereto.

In another embodiment, the present invention relates to an isolated EC-SOD gene sequence, or portion thereof.

Objects and advantages of the present invention will be clear from the description that follows.

BRIEF DESCRIPTION OF THE DRAWINGS

FIG. 13 shows a Western blot analysis of rh-EC-SOD and a human lung homogenate to demonstrate antibody specificity. Proteins were separated on a 10% 0.75 mm SDS-polyacrylamide gel and transferred to nitrocellulose. Proteins were hybridized with the antibody to recombinant human EC-SOD (4.3 µg/ml) and the antibody was detected by hybridization with $^{125}$I-Protein-A followed by autoradiography. The EC-SOD lane contained 0.05 µg of pure recombinant human type C EC-SOD lane protein. The lung lane contained 10 µg of a 20,000×g supernatant of a human lung homocenate.

FIGS. 20A–20D show a partial restriction map, sequencing strategy, genomic structure, and protein structure of human EC-SOD Clone #7. FIG. 20A, a partial restriction map of human EC-SOD genomic clone #7 is shown in the 5' to 3' orientation. A 1 kb size marker is indicated. B, BamH I; H, Hind III; P, Pst I; S, Sal I; K, Kpn I; E, EcoR I. In FIG. 20B, the subcloning and sequencing strategy is shown. Various size overlapping restriction fragments were subcloned into the plasmid vector pGEM3Zf(+) for subsequent DNA sequence analysis. All DNA was sequenced on both strands using Sequenase (USB) and double-stranded DNA template, except for ~2 kb of the 3' 7K36 fragment in which only one orientation was sequenced. In FIG. 20C, the exon/intron structure of the human EC-SOD gene is shown. The position of the coding region for preEC-SOD in exon 3 is shown by the dashed lines. In FIG. 20D, the four structural domains of human EC-SOD protein are diagrammed. The signal peptide is indicated by an arrow. This is followed by the mature glycosylated (CHO) amino terminal peptide domain. A third region has very high amino acid sequence homology to human CuZn-SOD. The carboxy terminal domain has multiple charged basic residues (+) which are critical for binding heparin glycosaminoglycan.

FIG. 21A, two μg of poly A(+) MRNA from eight different human tissues were electrophoresed on a denaturing agarose gel, transferred to a charged nylon membrane, and probed with [$^{32}$P]-labeled antisense human EC-SOD cRNA. RNA molecular size markers, (kilobases) are shown on the right. Quantitative transfer was monitored by ethidium bromide staining. The results demonstrate a unique 1.4 kb mRNA present in all eight tissues examined. Interestingly skeletal muscle demonstrates a second, larger MRNA of ~4.2 kb, while brain shows a faint approximately 2.2 kb band. In FIG. 21B, bands corresponding to EC-SOD MRNA were quantitated by laser densitometric scanning, normalized to the 1.4 kb brain band, and expressed as relative absorbance units.

In FIG. 22A, a schematic diagram illustrates the annealing sites for the various oligonucleotides. The dark line represents first-strand reverse transcribed cDNA of human heart poly A(+) mRNA which has been primed with EC7 (an EC-SOD gene specific primer) and poly C tailed using terminal deoxynucleotidyl transferase (TdT). HEC1, HEC2, EC4, and EC7 are 5' human EC-SOD gene specific primers. The anchor primer is supplied with the 5' RACE kit (GIBCO BRL) and hybridized to the poly C tail. In FIG. 22B, PCR was used to amplify segments of DNA using [anchor+EC4] or [HEC1+EC7] as primers and either poly C tailed (+TdT, lanes 1 & 4) or non-poly C tailed (−TdT, lanes 2 & 5) cDNA as template. Lane 3 includes PCR amplified DNA using [HEC1+EC7] as primers and a full-length human EC-SOD cDNA as template. The resulting amplified DNAs were electrophoresed on a 2% agarose gel, transferred to charged nylon membranes, and probed with [$^{32}$p]-labeled HEC2, a 5' nested gene specific EC-SOD primer. DNA molecular weight markers were run between lanes 2 and 3. The expected size of the PCR amplified region in lanes 3, 4 and 5 is 217 bp. Only a single band is seen in lane 1, with a molecular size of approximately 185 to 200 bp.

FIG. 24 to FIG. 24-5 shows the nucleotide sequence and deduced amino acid sequence of the human EC-SOD gene. The complete nucleotide sequence of the human gene is shown. The deduced amino acid sequence of the signal peptide and mature protein is indicated using the single letter amino acid code.

FIG. 26 shows the protection of pulmonary artery endothelial cells from xanthine oxidase-induced injury by

Figure 27:
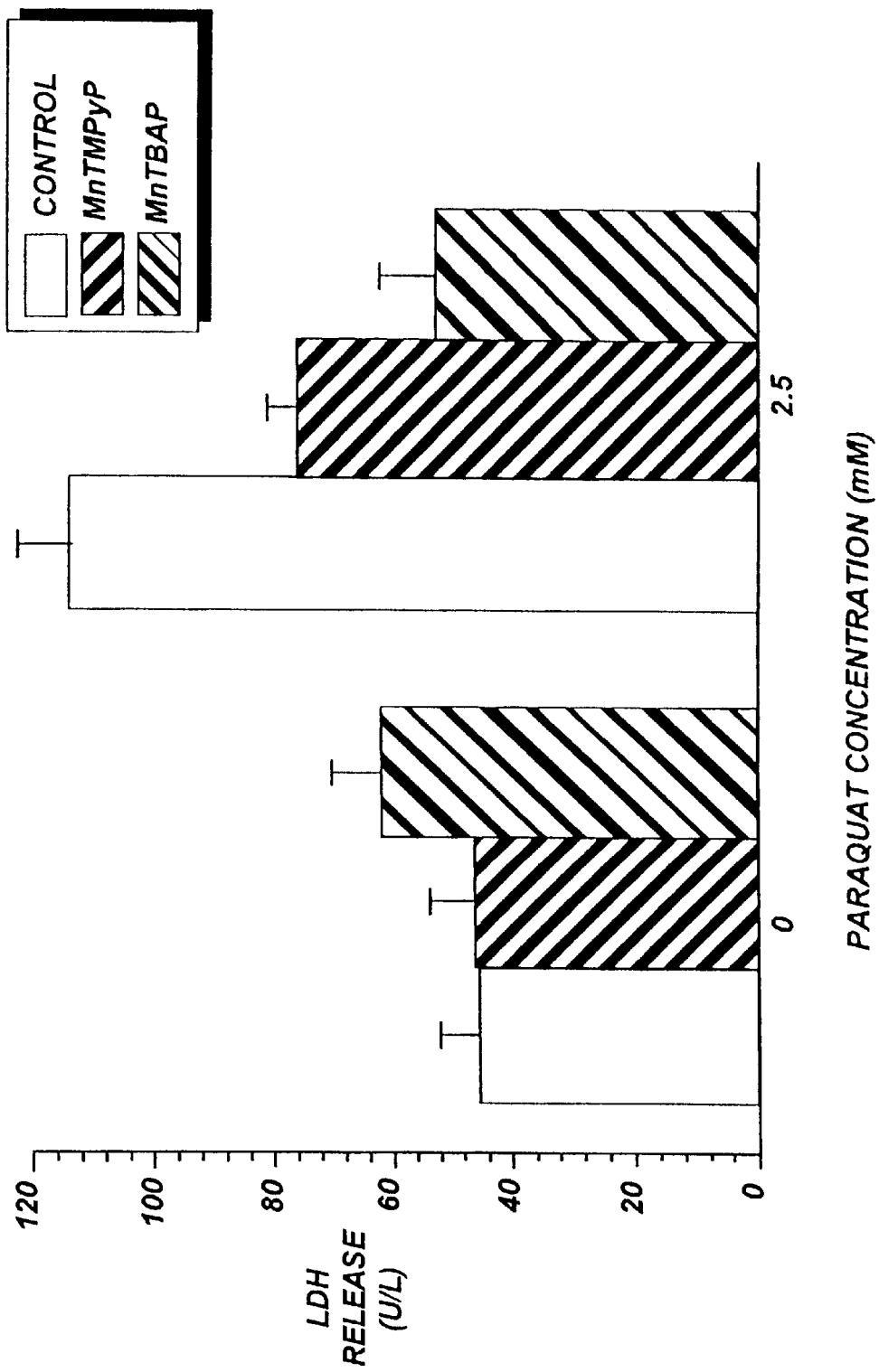

FIG. 27 shows the protection of lung epithelial cells from paraquat-induced injury of SOD mimetics.

Figure 28:
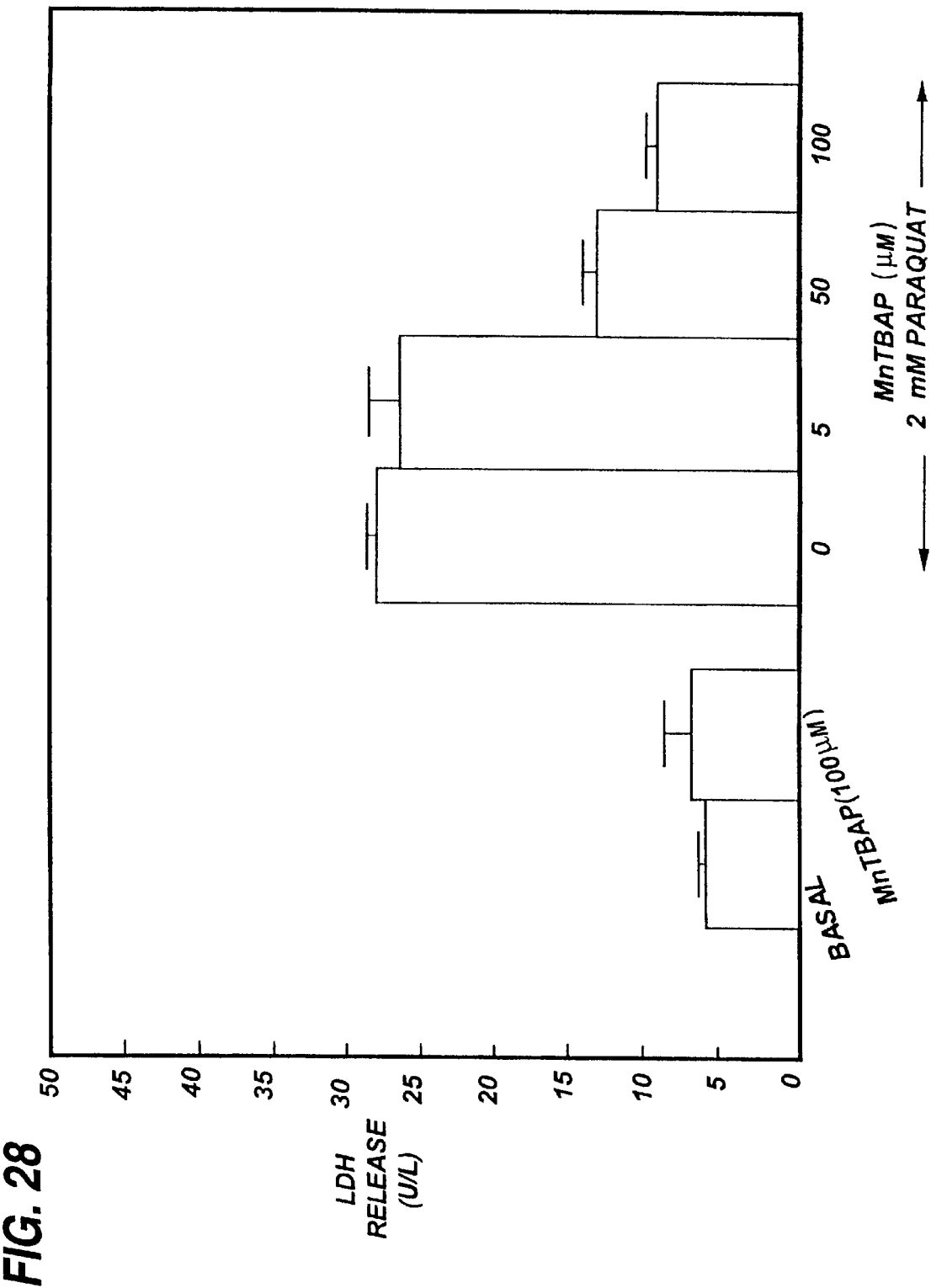

FIG. 28 shows the protection of pulmonary artery endothelial cells from paraquat-induced injury by MnTBAP.

Figure 29:
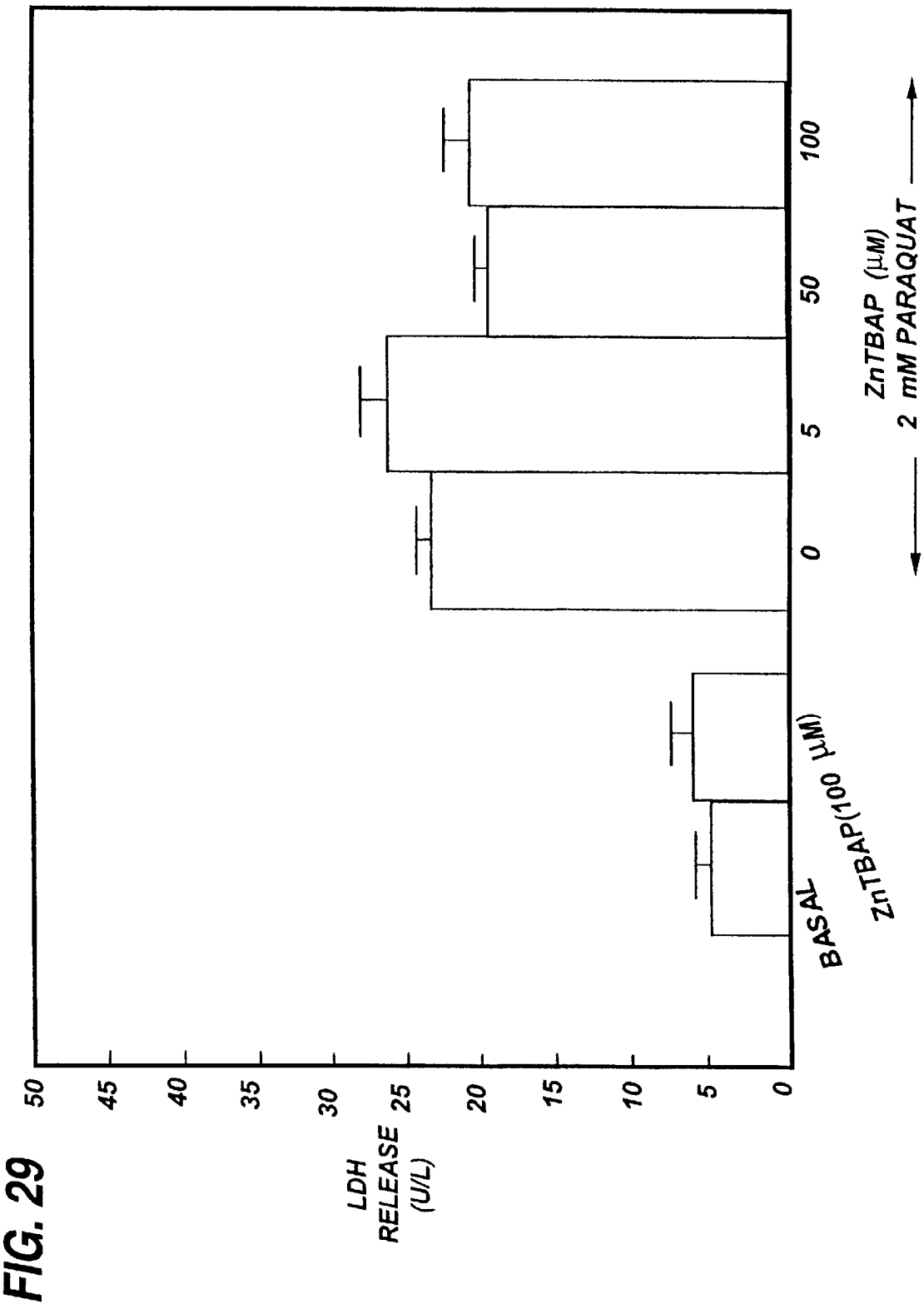

FIG. 29 shows the lack of protection of pulmonary artery endothelial cells from paraquat-induced injury by ZnTBAP.

Figure 30:
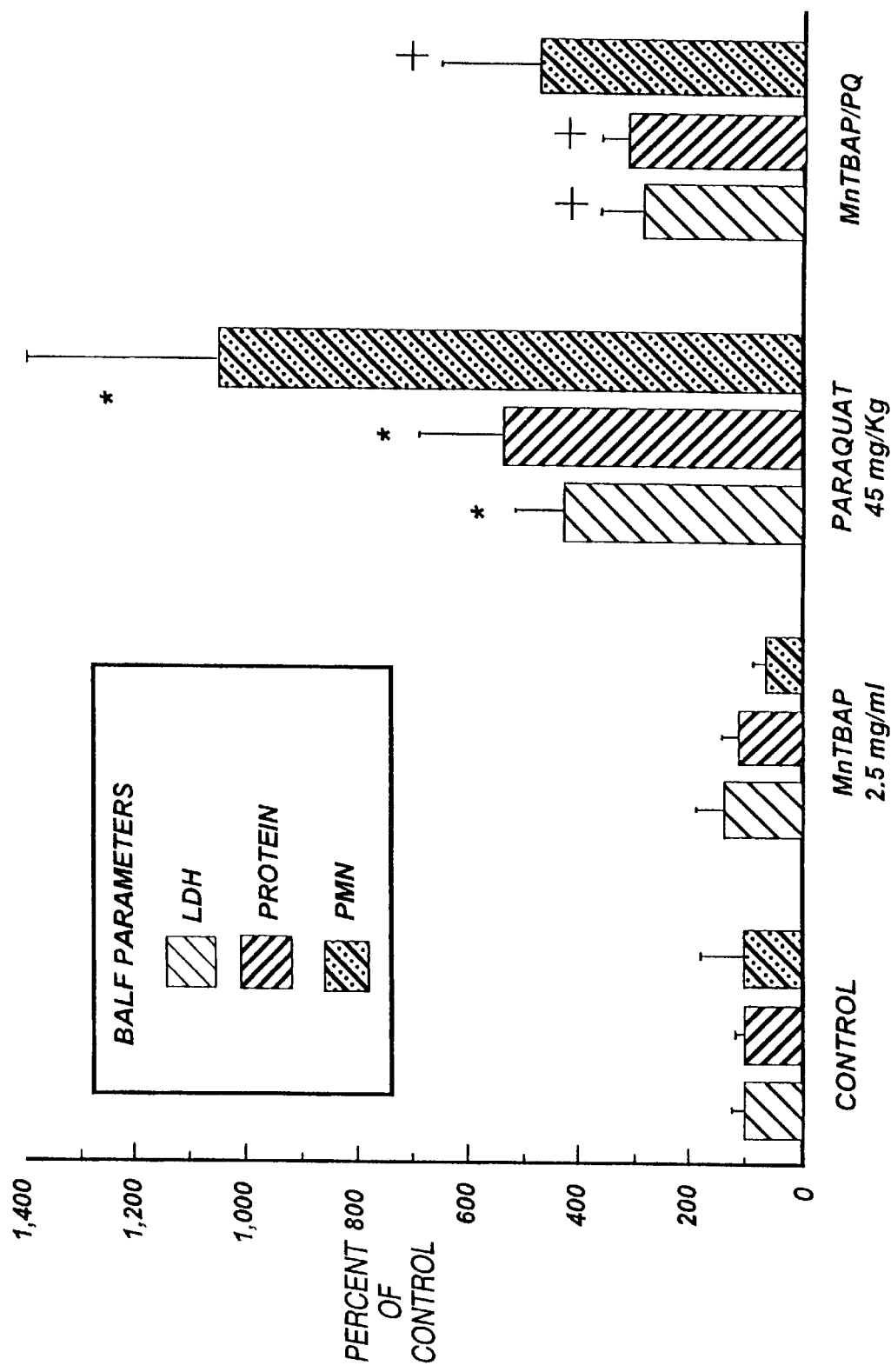

FIG. 30 shows the protection of MnTBAP against paraquat-induced lung injury.

Figure 31:
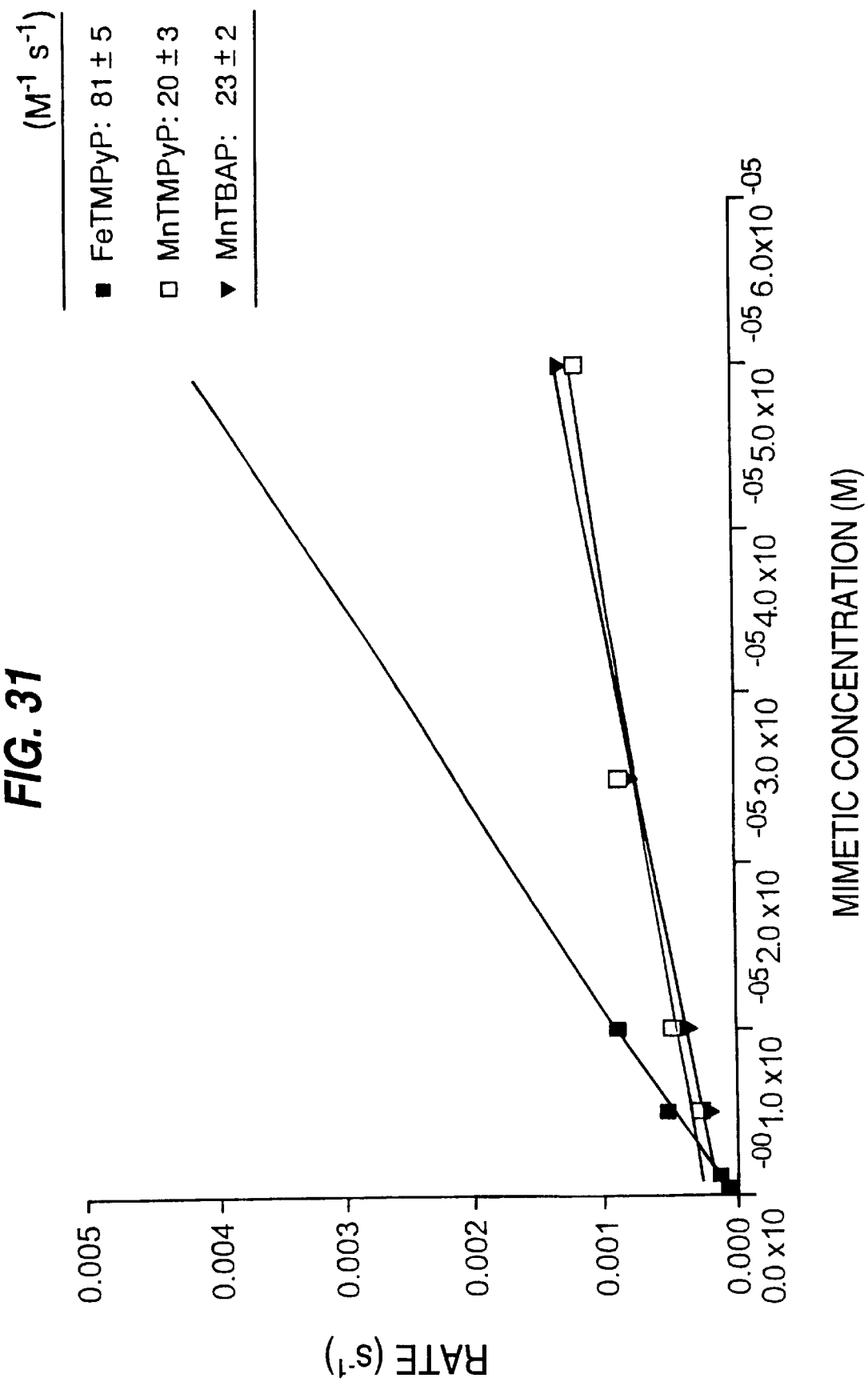

FIG. 31 shows a second order rate constant plot for catalase mimetics.

Figure 32:
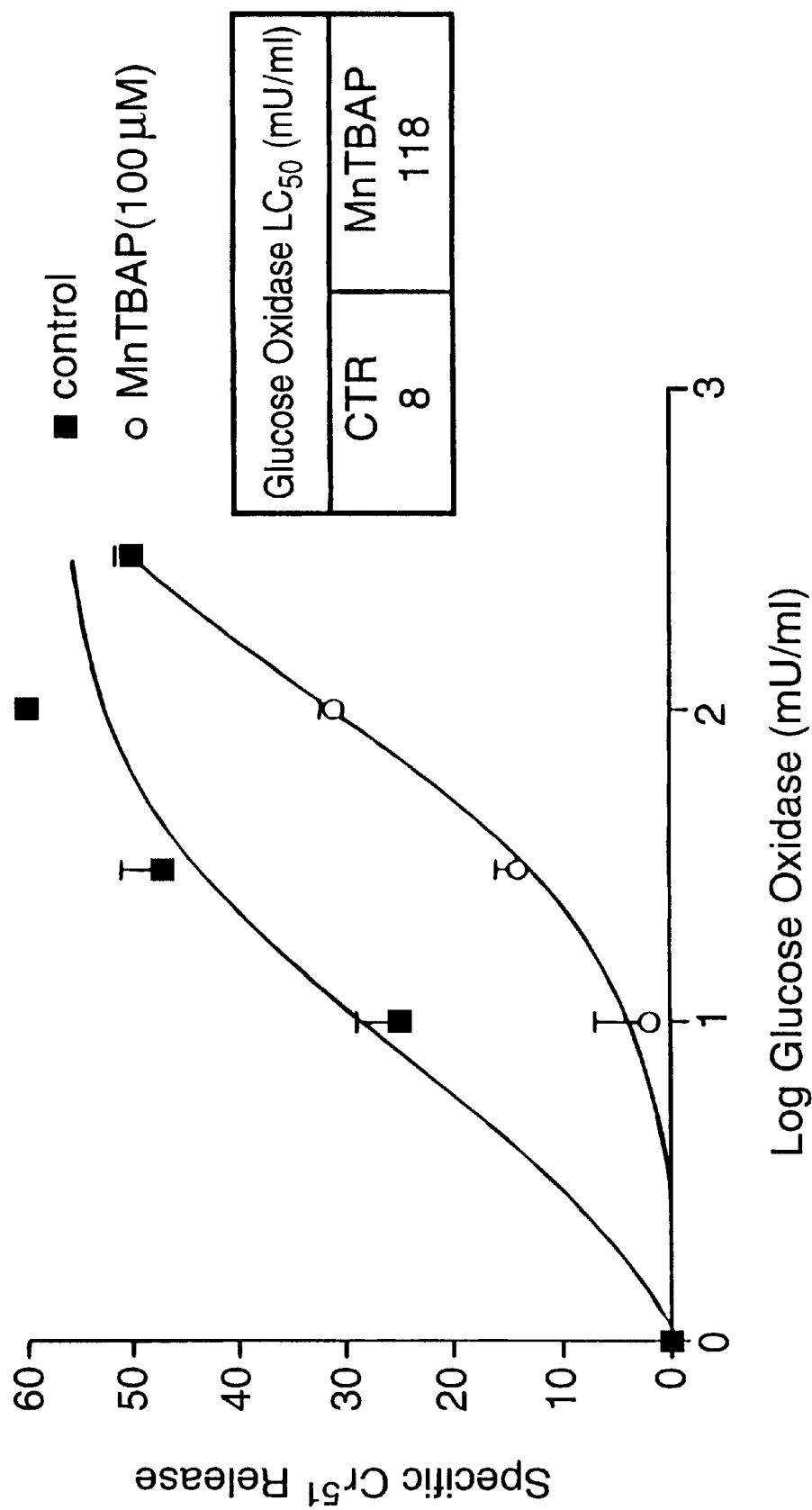

FIG. 32 shows the effect of MnTBAP on $H_2O_2$-induced endothelial injury.

Figure 33B:
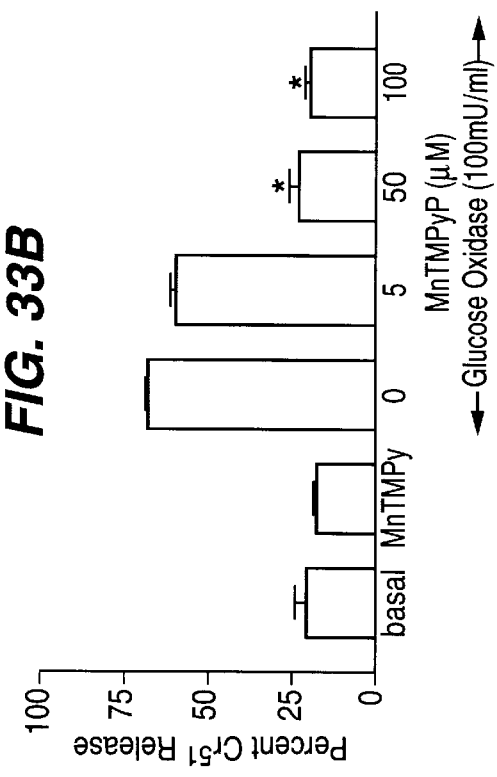
Figure 33D:
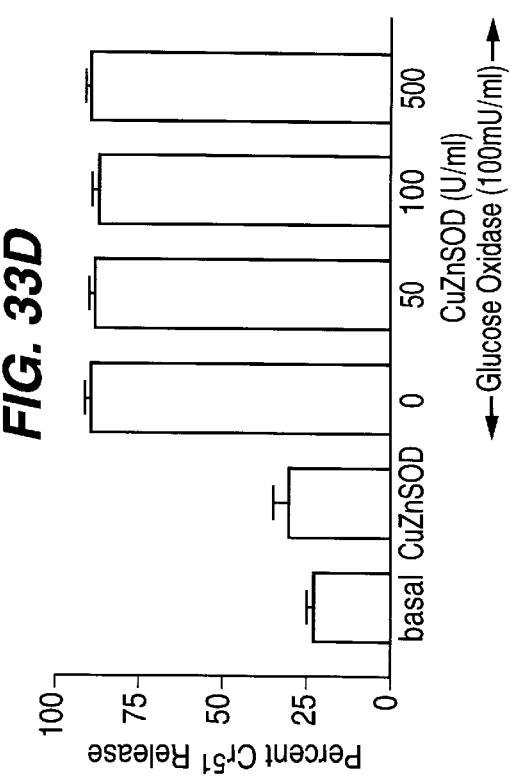
Figure 33A:
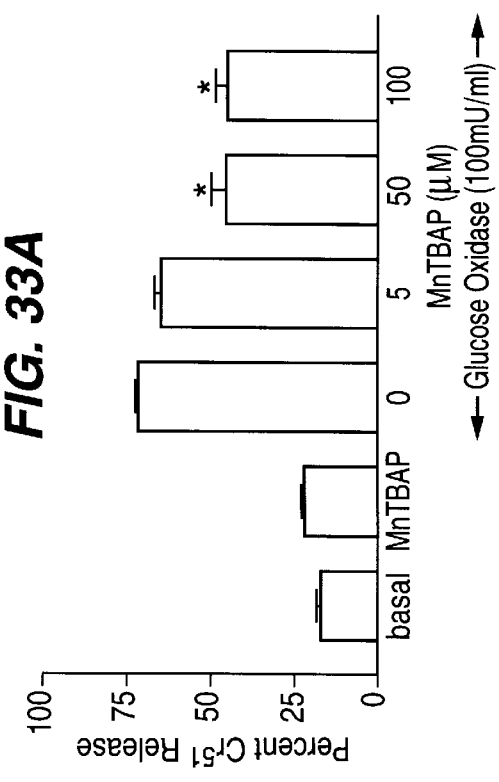
Figure 33C:
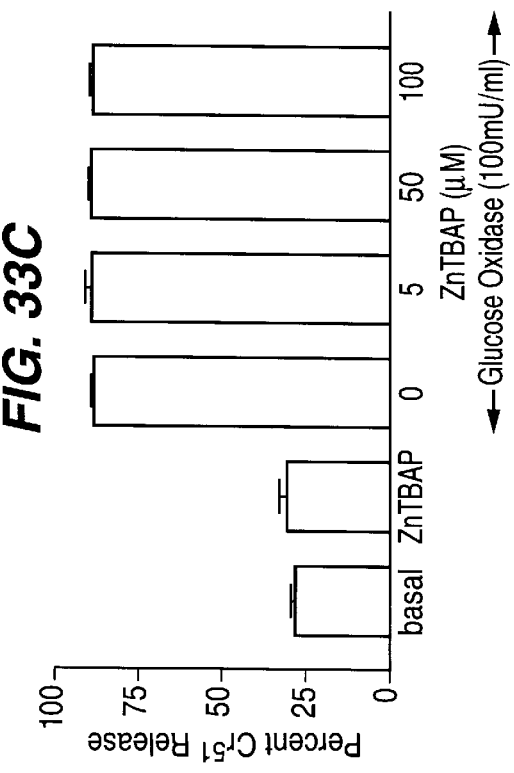

FIGS. 33A and B show the reduction by MnTBAP and MnTmPyP of endothelial cell injuries caused by exposure to glucose oxidase-produced hydrogen peroxide. FIG. 33C shows that ZnTBAP does not reduce hydrogen peroxide-induced endothelial cell injury. FIG. 33D shows that endothelial cells are not protected from hydrogen peroxide-induced injury by CuZnSOD.

DETAILED DESCRIPTION OF THE INVENTION

The present invention relates to methods of protecting against the deleterious effects of oxidants, particularly, superoxide radicals and hydrogen peroxide, and to methods of preventing and treating disease states that involve or result from oxidant stress. The invention also relates methods of modulating biological processes involving oxidants, including superoxide radicals and hydrogen peroxide. The invention further relates to compounds and compositions, including low molecular weight antioxidants (eg mimetics of scavengers of reactive oxygen species, including mimetics of SODs, catalases and peroxidases) and formulations tLereof, suitable for use in such methods.

Mimetics of scavengers of reactive oxygen species appropriate for use in the present methods include manganic derivatives of methine substituted porphines, or pharmaceutically acceptable salts thereof. Preferred mimetics are of the formula:

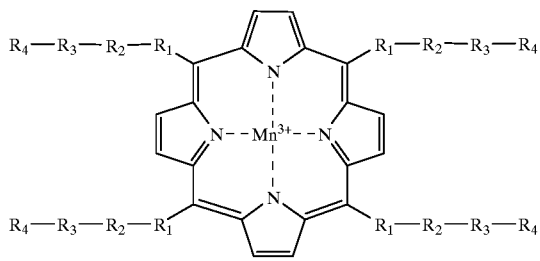

wherein:

$R_1$ is a bond,

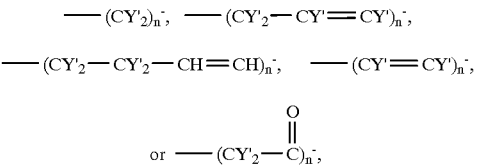

wherein X is a halogen and Y is an alkyl group and wherein

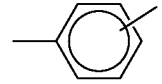

indicates bonding to $R_2$ at any position 1 and

indicates bonding to $R_2$ and the substituent.

$R_2$ is a bond,

—(CY'$_2$)$_n^-$,  —(CY'$_2$—CY'═CY')$_n^-$,

—(CY'$_2$—CY'$_2$—CH═CH)$_n^-$,  —(CY'═CY')$_n^-$, or  —(CY'$_2$—$\overset{O}{\underset{\|}{C}}$)$_n^-$, wherein Y' is hydrogen or an alkyl group and wherein n is 1 to 8;

$R_3$ is a bond, hydrogen, —Y", —OH, —NH—, —N$^+$(Y")$_3$, —COO—, —COO$^-$, —SO$_3$—, —SO$_3^-$, —C—PO$_3$H— or —C—PO$_3$H$^-$, wherein Y" is an alkyl group, and $R_4$ is nothing, hydrogen, a cell surface or extracellular matrix targeting moiety or a linker-cell surface or extracellular matrix targeting moiety (wherein a "linker" is a moiety that links the mimetic core (porphyrin ring and $R_1$, $R_2$, $R_3$) to the targeting moiety).

In a more specific embodiment.

$R_1$ is a bond,

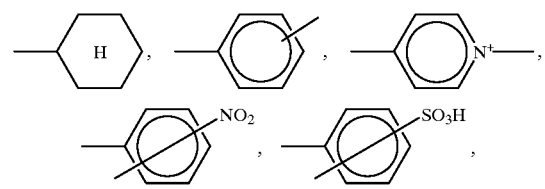

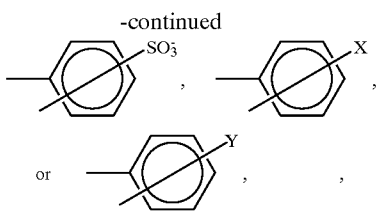

wherein X is Cl or Br and Y is a $C_{1\text{-}4}$ alkyl group;

$R_2$ is a bond, $-(CY'_2)_n-$, $-(CY'_2-CY'=CY')_n^-$, $-(CY'_2-CY'_2-CH=CH)_n^-$, $-(CY'=CY')_n^-$, or

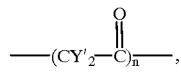

wherein Y' is hydrogen or a $C_{1\text{-}4}$ alkyl group and wherein n is 1 to 4;

$R_3$ is a bond, hydrogen, Y", $-OH$, $-NH-$, $-N^+(Y")_3$, $-COO-$, $-COO^-$, $-SO_3-$, $-SO_3^-$, $-C-PO_3H-$ or $-C-PO_3H^-$, wherein Y" is a $C_{1\text{-}4}$ alkyl group, and $R_4$ is nothing, hydrogen, a cell surface or extracellular matrix targeting moiety or a linker-cell surface or extracellular matrix targeting moiety.

In a further specific embodiment, $R_1$ is a bond,

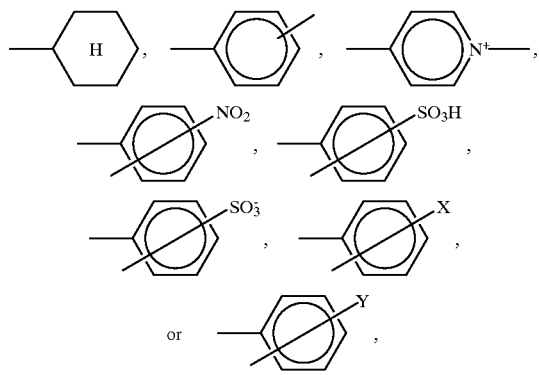

wherein X is Cl or Br and Y is methyl or ethyl, and $R_2$ is a bond,

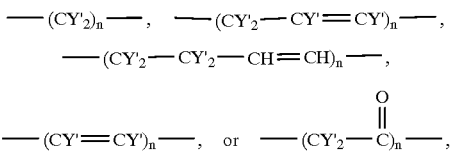

wherein Y' is hydrogen or methyl or ethyl and wherein n is 1 or 2;

$R_3$ is a bond, hydrogen, methyl, ethyl, $-OH$, $-NH-$, $-N^+(CH_3)_3$, $-N^+(CH_2CH_3)_3$, $-COO-$, $-COO^-$, $-SO_3-$, $-SO_3^-$, $-C-PO_3H$ or $-C-PO_3H^-$; and $R_4$ is nothing, hydrogen, a cell surface or extracellular matrix targeting moiety, or a linker-cell surface or extracellular matrix targeting moiety.

In another specific embodiment, $R_1$ is a bond,

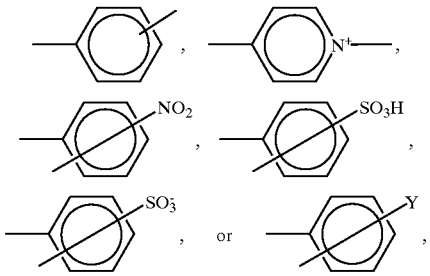

wherein Y is alkyl, preferably, $C_{1\text{-}4}$ alkyl, more preferably methyl or ethyl, $R_2$ is a bond,

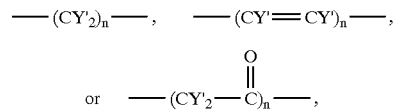

wherein Y' is hydrogen or alkyl (preferably $C_{1\text{-}4}$ alkyl, more preferably methyl or ethyl) and wherein n is 1 to 4 (preferably 1 or 2);

$R_3$ is a bond, hydrogen, $C_{1\text{-}4}$ alkyl (preferably methyl or ethyl), $-OH$, $-NH-$, $-N^+(CH_3)_3$, $-N^+(CH_2CH_3)_3$, $-COO-$, $-COO^-$, $-SO_3-$, $-SO_3^-$, $-C-PO_3H-$ or $-C-PO_3H^+$; and $R_4$ is nothing, hydrogen, a cell surface or extracellular matrix targeting moiety or a linker-cell surface or extracellular matrix targeting moiety.

In yet another specific embodiment, $R_1$ is a bond,

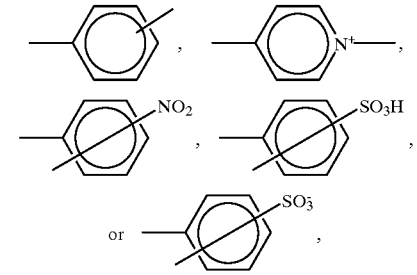

or $R_2$ is a bond, $-(CY'_2)_n^-$ or $-(CY'=CY')_n^-$, wherein Y' is hydrogen or alkyl (preferably $C_{1\text{-}4}$ alkyl, more preferably methyl or ethyl) and wherein n is 1 to 4 (preferably 1 or 2);

$R_3$ is a bond, hydrogen, $C_{1\text{-}4}$ alkyl (preferably methyl or ethyl), $-OH$, $-NH-$, $-N^+(CH_3)_3$, $-N^+(CH_2CH_3)_3$, $-COO-$, $-COO^-$, $-SO_3-$, $-SO_3^-$, $-C-PO_3H^-$or $-C-PO_3H^{31}$; and $R_4$ is nothing, hydrogen, a cell surface or extracellular matrix targeting moiety or a linker-cell surface or extracellular matrix targeting moiety.

In addition to the substituents described above, one or more of the pyrrole rings of the porphyrin can be substituted with an electron withdrawing group, for example, a $NO_2$ group, a halogen (eg Cl), or a nitrile.

Specific mimetics suitable for use in the present methods include Mn(III) tetrakis (1-methy-4-pyridyl)porphyrin (MnTMPyP), Mn(III) tetrakis (4-trimethyl-aminophenyl) porphyrin (MnTMAP) and Mn (III) tetrakis (4-benzoic acid)porphyrin (MnTBAP), with or without a cell surface or extracellular matrix targeting moiety or a linker-cell surface or extracellular matrix targeting moiety at the $R_4$ position.

Although the foregoing mimetics are described as manganese chelates, metals other than manganese, such as iron (III) and copper (II), can also be used. The present invention also relates to the metal-free nitrogen-containing macro cyclic ligand.

Targeted forms of the mimetics can be produced by coupling directly or via a linker to a cell surface or extracellular matrix targeting moiety, as indicated above in the definition of $R_4$. The targeted mimetics can be used to mimic EC-SOD and to scavenger $H_2O_2$. Since the sequence of human EC-SOD is known (Hjalmarsson et al, Proc. Natl. Acad. Sci. U.S.A. 84:6340 (1987)) the C-terminal oligopeptide can prepared and attached to the "mimetic core" (eg, a Mn(III)-porphyrin) via, for example, a free amine or carboxy group with a 1-ethyl-3-(3-dimethylaminopropyl) carbodiimide (EDC) coupling reaction (Yamada et al, Biochemistry 20:4836 (1981); Davis and Preston, Anal. Biochem. 116:402 (1981)) (note the R' group in the structures set forth below). This simple coupling procedure makes it possible to attach a wide variety of different binding domains in order to target the mimetics of the invention. Heparin binding affinity of a mimetic can be assessed by passing the mimetic over a heparin-sepharose CL-6B column (Karlsson et al, Biochem. J. 256:29 (1988)).

Candidate targeting moieties suitable for attaching to the mimetics of the invention to confer GAG binding properties include the following:

i) the A+ helix of protein C inhibitor (Boissinot et al, Biochem. Biophys. Res. Commun. 190:250 (1993)) —$NH_2$—His Arg His His Pro Arg Glu Met Lys Lys Arg Val Glu Asp Leu—COOH;

ii) the C-terminal end of human EC-SOD heparin binding domain) (Karlsson et al, Biochem. J. 255:223 (1988))—$NH_2$—Arg Glu His Ser Glu Arg Lys Lys Arg Arg Arg Glu Ser Glu Cys Lys Ala Ala—COOH;

iii) variants of the C-terminal end of human EC-SOD having heparin binding affinity (Sandstrom et al, J. Biol. Chem. 267:18205 (1992))

a. NH2—Arg Glu His Ser Glu Arg Lys Lys Arg Arg Arg Glu—COOH;

b. $NH_2$—Arg Glu His Ser Glu Arg Lys Lys Arg Arg Arg Ala—COOH;

c. $NH_2$—Arg Glu His Ser Glu Arg Lys Lys Arg Arg Arg Ala Ser Glu Cys Lys Ala Ala—COOH;

d. $NH_2$—Arg Glu His Ser Glu Arg Lys Lys Arg Arg Arg Glu Ser Glu Ala Lys Ala Ala—COOH;

e. $NH_2$—Arg Glu His Ser Glu Arg Lys Lys Arg Arg Arg Glu Ser Glu Cys Ala Ala Ala—COOH;

f. $NH_2$—Arg Glu His Ser Glu Arg Lys Lys Arg Arg Arg Ala Ser Ala Cys Lys Ala Ala—COOH;

g. $NH_2$—Arg Glu His Ser Glu Arg Lys Lys Arg Arg Arg Ala Ser Glu Cys Ala Ala Ala—COOH;

h. $NH_2$—Arg Glu His Ser Glu Arg Lys Lys Gly Arg Arg Ala Ser Glu Cys Ala Ala Ala—COOH;

iv) any combination of repeating positively changed amino acids (ie poly $(Arg)_n$, poly $(Lys)_n$, poly $(Arg)_n$ $(Lys)_n$ or poly (Arg Lys)$_n$, or poly (Lys Arg)$_n$, poly (Lys Lys Arg Arg)$_n$, wherein n is, preferably, in the range of 1 to 12, more preferably, 1 to 8, and, most preferably, 1 to 6, with or without a C-terminal Glu or Ala (Sandström et al, J. Biol. Chem. 267:18205 (1992)); and v) polyethyleneimine, e.g. $(NH—CH_2—CH_2—NH)nH$, wherein n is 1 to 6.

In addition to the foregoing, targeting moieties also include heparin binding proteins generally and sugars, including mannose and oligosaccharides.

Appropriate linkers include

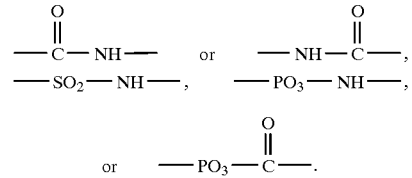

Specific examples of suitable mimetics of the invention are set forth below:

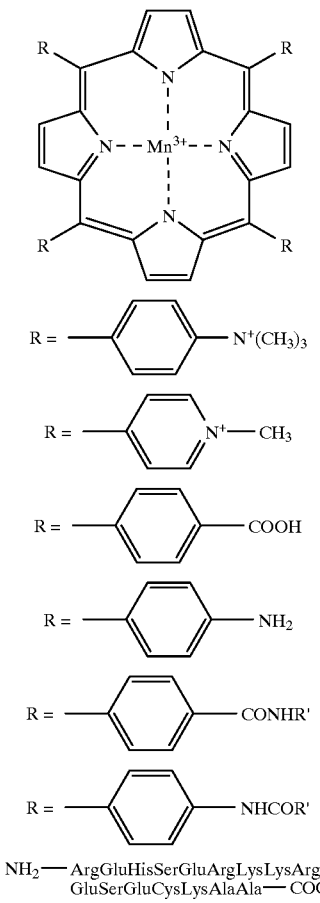

R' = $NH_2$—ArgGluHisSerGluArgLysLysArgArgArg
GluSerGluCysLysAlaAla—COOH 5, 10, 15, 20-Tetra Kis [R-group]
manganese (III) porphyrin Mimetics suitable for use in the present methods can be selected by assaying for SOD, catalase and/or peroxidase activity and stability.

SOD activity can be monitored in the presence and absence of EDTA using the method of McCord and Fridovich (J. Biol. Chem. 244 (1969)). The efficacy of a mimetic can be determined by measuring the effect of the mimetic on the growth of a SOD null E. coli strain versus a wild type strain. Specifically, wild type E. coli (AB1157) and SOD null E. coli. (JI132) can be grown in M9 medium containing 0.2% casamino acids and 0.2% glucose at pH 7.0 and 37° C.;

growth can be monitored in terms of turbidity followed at 700 nm spectrophotometrically. Active mimetics can be tested for toxicity in mammalian cell culture by measuring lactate dehydrogenase (LDH) release. Specifically, rat L2 cells (a lung type II like cell; (Kaighn and Douglas, J. Cell Biol. 59:160a (1973))can be grown in Ham's F-12 medium with 10% fetal calf serum supplement at pH 7.4 and 37° C.; cells can be seeded at equal densities in 24 well culture dishes and grown to approximately 90% confluence; SOD mimetics can be added to the cells at log doses (eg micromclar doses in minimal essential medium (MEM)) and incubated for 24 hours. Toxicity can be assessed by morphology and by measuring the release of the cytosolic injury marker, LDH (eg on a thermokinetic plate reader), as described by Vassault (In: Methods of Enzymatic Analysis, Bergmeyer (ed) pp. 118–26 (1983); oxidation of NADH is measured at 340 nm). Efficacy of active mimetics can be assessed by determining their ability to protect mammalian cells against methylviologen (paraquat)-induced toxicity. Specifically, rat L2 cells grown as described above and seeded into 24 well dishes can be pre-incubated with various concentrations of the SOD mimetic and then incubated with a concentration of methylviologen previously shown to produce an $LC_{75}$ in control L2 cells. Efficacy of the mimetic can be correlated with a decrease in the methylviologen-induced LDH release (St. Clair et al, FEBS Lett. 293:199 (1991)). The efficacy of SOD mimetics can be tested in vivo with mouse and/or rat models using both aerosol administration and parental injection. For example, male Balb/c mice can be randomized into 4 groups of 8 mice each to form a standard 2×2 contingency statistical model. Animals can be treated with either paraquat (40 mg/kg, ip) or saline and treated with SOD mimetic or vehicle control. Lung injury can be assessed 48 hours after paraquat treatment by analysis of bronchoalveolar lavage fluid (BALF) damage parameters (LDH, protein and % PMN) as previously described (Hampson et al, Tox. Appl. Pharm. 98:206 (1989); Day et al, J. Pharm. Methods 24:1 (1990)). Lungs from 2 mice of each group can be instillation fixed with 4% paraformaldehyde and processed for histopathology at the light microscopic level.

Catalase activity can be monitored by measuring absorbance at 240 nm in the presence of hydrogen peroxide (see Beers and Sizer, J. Biol. Chem. 195:133 (1952)) or by measuring oxygen evolution with a Clark oxygen electrode (Del Rio et al, Anal. Biochem. 80:409 (1977)). Peroxidase activity can be measured spectrophotometrically as previously described by Putter and Becker: Peroxidases. In: Methods of Enzymatic Analysis, H. U. Bergmeyer (ed.), Verlag Chemie, Weinheim, pp. 286–292 (1983)

Synthesis of mimetics suitable for use in the present method can be effected using art-recognized protocols. In the case of Mn(III)-porphyrin mimetics, porphyrin rings with various methine bridge carbon side groups can be purchased commercially and the Mn(III) metal ion inserted into the porphyrin ring by methods including the following: (1) admixture of Mn(II) acetate with porphyrin in the presence of oxygen, under which condition selective stabilization of Mn(III) by the porphyrin causes autooxidation of Mn(II); (2) preparation of $Mn(III)(OH)_3$ by a modification of the Winkler method (Sastry et al, Anal. Chem. 41:857 (1969)) followed by reaction with the porphyrin; (3) stirring $MnO_2$ with the porphyrin in the presence of $NH_2OH$, which serves to reduce the Mn(IV) to Mn(III), which is then trapped by the porphyrin; or (4) a method modified from Pasternack et al (Biochemistry 22:2406 (1983)) which refluxes excess $MnCl_3$ with the porphyrin. Mn(III)-porphyrin complexes can be precipitated from solution with sodium perchlorate, washed and residue perchlorate removed by strong anionic exchange resin. Formation of the Mn(III)-porphyrin can be followed spectrophotometrically by monitoring a characteristic Sorét band at 468 nm. Coupling of a binding domain to the "mimetic core" can be carried out as described above.

One embodiment of the present invention results, at least in part, from the realization that EC-SCD specifically regulates NO. function. In addition, the invention is based on the realization that EC-SOD is synthesized by epithelial cells and is primarily localized in the interstitium, on matrix elements and collagen and around smooth muscle cells (particularly lung airways and vasculature). NO. is an intercellular signal and, as such, NO. must traverse the extracellular matrix to exert its effects. NO., however, is highly sensitive to inactivation mediated by $O_2^-$ present in the extracellular spaces. EC-SOD is thus an enzyme ideally suited to increase the bioavailability of NO. by preventing its degradation by $O_2^-$.

One embodiment of the present invention relates to a method of regulating extracellular NO. levels using polypeptides having EC-SOD activity. As indicated above, the invention also relates to mimetics of EC-SOD that can be targeted to strategic locations and to the use of such mimetics in manipulating extracellular levels of NO.. The invention, however, is not limited to NO. manipulation as the sole mechanism of action of the compounds, mimetics, etc, of the invention. Rather, the invention relates to oxygen radical and hydrogen peroxidase scavenging generally.

The present invention relates, in a further specific embodiment, to a method of inhibiting production of superoxide radicals. In this embodiment, the mimetics of the invention are used to inhibit oxidases, such as xanthine oxidase, that are responsible for production of superoxide radicals (see Example VII). The ability of a mimetic to protect mammalian cells from xanthine/xanthine oxidase-induced injury can be assessed, for example, by growing rat L2 cells in 24-well dishes. Cells can be pre-incubated with various concentrations of a mimetic and then xanthine oxidase (XO) can be added to the culture along with xanthine (X). The appropriate amount of XO/X used in the study can be pre-determined for each cell line by performing a dose-response curve for injury. X/XO can be used in an amount that produces approximately an $LC_{75}$ in the culture. Efficacy of the mimetic can be correlated with a decrease in XO/X-induced LDH release. The ability of the mimetics to inhibit the production of such radicals makes possible the use the mimetics as therapeutics for the treatment of gout and reperfusion injuries.

The mimetics of the invention can be used as catalytic scavengers of reactive oxygen species to protect against ischemia reperfusion injuries associated with myocardial infarction, stroke, acute head trauma, organ reperfusion following transplantation, bowel ischemia, pulmonary infarction, surgical occlusion of blood flow, and soft tissue injury. The mimetics can further be used to protect against skeletal muscle reperfusion injuries. The mimetics can also be used to protect against damage to the eye due to sunlight (and to the skin) as well as glaucoma, and macular degeneration of the eye. Diseases of the bone are also amenable to treatment with the mimetics. Further, connective tissue disorders associated with defects in collagen synthesis or degradation can be expected to be susceptible to treatment with the present mimetics.

In addition to scavenging superoxide, the ability of the mimetics of the invention to scavenge hydrogen peroxide would protect from the possible formation of the highly reactive hydroxyl radical by interfering with Fenton chemistry (Aruoma and Halliwell, Biochem. J. 241:273 (1987); Mello Filho et al, Biochem. J. 218:273 (1984); Rush and Bielski, J. Phys. Chem. 89:5062 (1985).

In addition to the above, the mimetics of the invention can be used as catalytic scavengers of reactive oxygen species to increase the very limited storage viability of transplanted hearts, kidneys, skin and other organs and tissues. The invention also provides methods of inhibiting damage due to autoxidation of substances resulting in the formation of $O_2^-$ including food products, pharmaceuticals, stored blood, etc. To effect this end, the mimetics of the invention are added to food products, pharmaceuticals, stored blood and the like, in an amount sufficient to inhibit or prevent oxidation damage and thereby to inhibit or prevent the degradation associated with the autoxidation reactions. (For other uses of the mimetics of the invention, see U.S. Pat. No. 5,227,405). The amount of mimetic to be used in a particular treatment or to be associated with a particular substance can be determined by one skilled in the art.

The availability of the mimetics of the invention also makes possible studies of $O_2^-$ and hydrogen peroxide mediated processes.

In addition to the above, the present invention relates to diagnostic protocols made possible by the availability of the EC-SOD gene sequence (see Example V and FIG. 24). A defect in the EC-SOD gene is more likely to occur than a defect in nitric oxide synthase due to the nature and number of physiological functions served by NO.. Detection of an EC-SOD gene defect would signal the need for measures to be undertaken to elevate levels of functional EC-SOD, or related superoxide scavenging compounds, at strategic locations to correct NO. imbalances and thus disorders involving oxidative stress.

To effect modulation of the efficacy of extracellular NO., eg, in relaxing smooth muscle, molecules (agents) having EC-SOD activity are administered under conditions such that levels of extracellular $O_2^-$ are altered. Molecules suitable for use in this method include forms of SOD that bind heparin sulfate or other glycosaminoglycans (GAG), for example, by virtue of the fact that they contain positively charged amino acids near their carboxy terminal end. Proteinaceous agents suitable for use in the present method include forms of EC-SOD C described in WO 91/04315, as well as additional polypeptides defined and described therein as having comparable or enhanced binding to heparin as compared to recombinant EC-SOD C (eg, polypeptides G1 and SA216; note also polypeptide SA219 which has the same heparin binding as recombinant EC-SOD C. Further proteinaceous agents suitable for use in the present method include chimeric proteins with targeted binding and SOD activity, for example, Cu/Zn SOD linked to an EC-SOD binding sequence (see also Boissinot et al, Biochem. Biophys. Res. Commun. 190:250 (1993)).

Proteinaceous molecules suitable for use in the present method can be synthesized chemically or recombinantly using art-recognized protocols (see WO 91/04315). Non-glycosylated recombinant peptides can be produced, for example, using host cells (ie, *E. coli* cells) that are incapable of effecting glycosylation, or using DNA sequences encoding functional proteins lacking glycosylation sites.

In addition to polypeptides, molecules suitable for use in the present method include mimetics of EC-SOD (eg targeted mimetics), including those described above. The general requirements of such mimetics are that they: (a) be stable enough to retain the ligated metal (eg Cu or Mn) in the presence of the multiple chelating agents present in living systems, (b) be active enough that reasonable doses can serve to significantly augment the total SOD activity in the extracellular spaces, (c) be able to adhere to the surfaces of cells or extracellular matrix elements (eg collagen) when protection against extracellular sources of $O_2^-$ is needed, and d) be of low toxicity. Examples of suitable mimetics include nitrogen-containing macro cyclic ligands effective as catalysts for dismutating superoxide, including Mn(III) complexes of porphyrins with bulky cationic substituents on the methine bridge carbons, such as those described above (eg MnTMAP and MnTMPyP). Such complexes are very active and are stable enough to retain full activity in the presence of excess EDTA or in the presence of tissue extracts.

The polypeptides and mimetics described above can be formulated into pharmaceutical compositions suitable for use in the present methods. Such compositions include the active agent (polypeptide or mimetic) together with a pharmaceutically acceptable carrier, excipient or diluent. The composition can be present in dosage unit form for example, tablets, capsules or suppositories. The composition can also be in the form of a sterile solution suitable for injection or inhalation. Compositions can also be in a form suitable for opthalmic use. The invention also includes compositions formulated for topical administration, such compositions taking the form, for example, of a lotion, cream, gel or ointment. The concentration of active agent to be included in the composition can be selected based on the nature of the agent, the dosage regimen and the result sought.

The dosage of the composition of the invention to be administered can be determined without undue experimentation and will be dependent upon various factors including the nature of the active agent, the route of administration, the patient, and the result sought to be achieved. A suitable dosage of protein administered IV can be expected to be in the range of about 10–1000 mg/day. For topical treatment, it is expected that lower doses will be required (see WO 91/04315); for aerosol administration, it is expected that doses will be in the range of 1 to 10 mg/kg. Suitable doses of mimetics will vary, for example, with the mimetic and with the result sought. The results of Faulkner et al (J. Biol. Chem. 269:23471 (1994)) indicate that the in vivo oxidoreductase activity of the mimetics is such that a pharmaceutically effective dose will be low enough to avoid problems of toxicity. Doses that can be used include those in the range of 1 to 50 mg/kg.

In addition to compositions of the types described above, the present invention also includes compositions suitable for use in gene therapy types of protocols. For example, the invention includes DNA sequences encoding proteins having EC-SOD activity and formulated so as to be incorporated into cells (eg, lung cells) upon contact therewith (eg, via inhalation). The sequence can be present in a vector, eg, a viral vector, and/or the sequence can be present in a delivery vehicle, such as a liposome. The amounts of such compositions to be administered can be readily determined by one skilled in the art.

Further examples of diseases or disorders appropriate for treatment using the compounds and compositions of the present invention include diseases of the central nervous system (including AIDS dementia, stroke, amyotrophic lateral sclerosis (ALS), Parkinson's disease and Huntington's disease) and diseases of the musculature (including diaphramic diseases (eg respiratory fatigue in emphysema, bronchitis and cystic fibrosis), cardiac fatigue of congestive heart failure, muscle weakness syndromes associated with myopathies, ALS and multiple sclerosis). Many neurologic disorders (including stroke, Huntington's disease, Parkinson's disease, ALS, Alzheimer's and AIDS dementia) are associated with an over stimulation of the major subtype of glutamate receptor, the NMDA (or N-methyl-D-aspartate) subtype. On stimulation of the NMDA receptor, excessive neuronal calcium concentrations contribute to a series of membrane and cytoplasmic events leading to production of oxygen free radicals and nitric oxide (NO.). Interactions between oxygen free radicals and NO. have been shown to contribute to neuronal cell death. Well-established neuronal cortical culture models of NMDA-toxicity have been developed and used as the basis for drug development. In these same systems the mimetics of the invention inhibit NMDA induced injury.

The present invention also relates to methods of treating arthritis, systemic hypertension, atherosclerosis, edema, septic shock, pulmona:y hypertension, including primary pulmonary hypertension, impotence, infertility, endometriosis, premature uterine contractions, memory disorders, microbial infections and gout.

Therapeutic regimens, including mode of administration, appropriate for effecting treatment of the conditions described above can be readily determined by one skilled in the art.

Inflammations, particularly inflammations of the lung, are amenable to treatment using the present invention (note particularly the inflammatory based disorders of asthma, ARDS including oxygen toxicity, pneumonia (especially AIDS-related pneumonia), cystic fibrosis, chronic sinusitis and autoimmune diseases (such as rheumatoid arthritis)). EC-SOD is localized in the interstitial spaces surrounding airways and vasculature smooth muscle cells. EC-SOD and $O_2^-$ mediate the antiinflammatory—proinflammatory balance in the alveolar septum. NO. released by alveolar septal cells acts to suppress inflammation unless it reacts with $O_2^-$ to form $ONOO^-$. By scavenging $O_2^-$, EC-SOD tips the balance in the alveolar septum against inflammation. Significant amounts of $ONOO^-$ will form only when EC-SOD is deficient or when there is greatly increased $O_2^-$ release. EC-SOD mimetics, such as those described herein, can be used to protect against destruction caused by hyperoxia. Appropriate therapeutic regimens can be readily established by one skilled in the art.

As indicated above, it is expected that defects in the EC-SOD gene, that are manifest in the protein itself, may in fact be the cause of pathologic problems related to NO. function, rather than defects in nitric oxide synthase. Thus, in a further embodiment, the present invention relates to diagnostic protocols suitable for use in identifying EC-SOD gene defects. This aspect of the invention is based on the availability of the EC-SOD gene sequence. The present invention includes within its scope the gene sequence presented in FIG. 24 as well as portions of non-coding regions of that sequence of at least 15 bases, preferably, at least 50 bases, more preferably, at least 100 bases and most preferably, at least 500 bases. Such portions, and the complements thereof, which are also within the scope of the invention, can be used as probes or primers in protocols including those described in Example VI.

Screening of subjects for defects in the EC-SOD gene can be done using the approach used to identify mutations on the β-adrenergic receptor gene (Reihaus et al, Am. J. Respir. Cell. Mol. Biol. 8:334 (1993)). That approach is similar to the one used by Rosen et al (Nature 262:59 (1993)) (see Example VI).

The following are predicted sites of important gene mutations:

Positions 1–558: This represents a 5' flanking region which contains transcriptional regulatory elements. Mutations here can be expected to lead to deficient levels of EC-SOD or defective enhancement or reduction in EC-SOD levels under conditions which require manipulating the EC-SOD concentration. The following regions have been identified as putative regulatory regions. Mutations in these regions can be expected to result in deficient levels of EC-SOD:

89–95 metal regulatory response element
   121–126 cyclic AMP responsive element
   370–375 glucocorticoid response element
   238–244 skeletal muscle trans-activating factor response element
   251–256 cis responsive element in the induction of the c-fos proto-oncogene
   162–168 TPA reponsive element
   171–179 SV40 enhancer region Positions 560–570: Mutations here can be expected to lead to an inability to splice out intron 1. This would result in no EC-SOD production (or much reduced) due to initiation of translation at multiple cryptic ATG sites located in intron 1 which are upstream of the EC-SOD ATG start codon. For example, base pair 653, 656, 720, 743, 748, etc, would potentially initiate translation.

Positions 564–1135: Intron 1 contains DNA sequence unique to EC-SOD. In addition, there are potential transcription regulatory regions within this DNA stretch which are listed below; mutations in intron 1 would lead to deficient levels of EC-SOD or defective enhancement or reduction in EC-SOD levels under conditions that require manipulating the EC-SOD concentration:

1085–1095 Xenobiotic responsive region
   650–661 Antioxidant responsive element Positions 71–95: Mutations here can be expected to lead to an inability to splice out intron 1. This would result in no EC-SOD production (or much reduced) due to initiation of translation at multiple cryptic ATG sites located in intron 1 that are upstream of the EC-SOD ATG start codon. For example, base pair 653, 656 720, 743, 748, etc, would potentially initiate translation.

Positions 1211–1230: Mutations here can be expected to lead to an inability to splice out intron 2. This would result in no EC-SOD production (or much reduced) due to initiation of translation at multiple cryptic ATG sites located in intron 2 that are upstream of the EC-SOD ATG start codon. Examples of upstream ATG translation start sites can be found at 1339 and 1518.

Positions 5055–5080: Mutations here would lead to an inability to splice out intron 2. This would result in no EC-SOD production (or much reduced) due to initiation of translation at multiple cryptic ATG sites located in intron 2 which are upstream of the EC-SOD ATG start codon. Examples of upstream ATG translation start sites can be found at 1339 and 1518.

Positions 5085–5138: Mutations here would (1) interfere with efficiency of translation of EC-SOD resulting in deficient levels of the enzyme (2) interfere with targeting of EC-SOD to the endoplasmic reticulum which is required for secretion of EC-SOD, (3) interfere with co-translational signal peptide processing (ie, removal of the signal peptide) that may lead to deficient levels due to inability to proteolytically cleave the signal peptide from the mature protein which in turn would result in the protein being trapped in the endoplasmic reticulum, (4) interfere with post-translational processing (specifically glycosylation) which may result in defective levels due to the synthesis of poorly soluble protein.

Positions 5139–5150: Mutations here may interfere with the signal peptidase cleavage site resulting in a mutant EC-SOD which would contain an altered amino terminus leading to defective EC-SOD function of deficient levels.

Positions 5403–5405: Mutations here can be expected to result in loss of glycosylation which may result in defective levels due to the synthesis of poorly soluble protein.

Positions 5424–5720: Mutations here can be expected to result in defective EC-SOD activity. This region is critical for binding to the substrate and catalyzing the dismutation of superoxide anion radical. In addition, this region would also affect any other activities of this enzyme including the reduction of other species such as nitric oxide, etc.

Positions 5721–5804: Mutations in this region would cause defects in binding of EC-SOD to target tissues such as type I collagen in the extracellular matrix, and around smooth muscle cells in both vessels and bronchi. Such mutations here are highly likely to cause disease.

Positions 6385–6395: Mutations here can be expected to result in defective polyadenylation that can lead to deficient levels of EC-SOD due to a decreased half-life of EC-SOD MRNA species.

The present invention relates not only to the entire EC-SOD gene sequence, but to portions thereof for use, for example, as probes or primers in detecting mutations in regions of the gene including those noted above. Such portions can be expected to be, for example, 18–1500 bases in length, preferably 18–22 bases in length, 50–75 bases in length, 100–400 bases in length or 500 to 1500 bases in length.

Certain details of the present invention are described in greater detail in the non-limiting Examples that follow.

EXAMPLE I

Preparation and Characterization of Transgenic Mice

Protocols:

i) Construction of Transgenic Mice

Construction of the human EC-SOD expression vector: The EC-SOD expression vector (FIG. 1) was constructed as follows: The entire human EC-SOD cDNA fragment (Hjalmarrson et al, Proc. Natl. Acad. Sci. U.S.A. 84:6340 (1987); Hendrickson et al, Genomics 8:736 (1990)) flanked by EcoRI restriction sites was converted with mung bean nuclease to form blunt-ends, ligated to Sa1I linkers, digested with Sa1I, and then inserted into the Sa1I site of the human β-actin expression vector pHβAPr-1. The EcoRI-HindIII fragment of the resultant plasmid containing the human β-actin promoter (provided by Dr. Larry Kedes of the University of Southern California, Los Angeles, Calif.), intron, and EC-SOD cDNA was isolated. In addition, the HpaI site of SV40 at position 2666 in plasmid pMSG (Pharmacia LKB Biotechnology, Piscataway, N.J.) was converted to a HindIII site by linker ligation and the HindIII-PstI fragment containing the polyadenylation site of the SV40 early region was isolated. These two DNA fragments were then ligated to an EcoRI plus PstI digested pKS vector (Stratogene, La Jolla, Calif.). The EcoRr-XbaI fragment containing the entire expression construct free of plasmid sequences was isolated and used to establish transgenic mice. All of the recombinant DNA procedures were done according to established methods (Sambrook et al, Molecular Cloning: A Laboratory Manual 3, Cold Spring Harbor; Cold Spring Harbor Laboratory, 1989).

Development of transgenic mice: Purified DNA at 2.5 μg/ml in 5 mM Tris-HCl, pH 7.4, 0.1 mM EDTA was injected into the pronuclei of fertilized eggs isolated from mice ((C57BL/6×C3H)F1×(C57BL/6×C3H)F1)((C57BL/6×C3H)F1 mice were purchased from Charles River). Mouse eggs surviving microinjection were then implanted into the oviducts of pseudcpregnant foster mothers (CD1) (CD1 mice were purchased from Charles River) following procedures described by Hogan et al (Hogan et al, Manipulating the Mouse Embryo, Cold Spring Harbor; Cold Spring Harbor Laboratory 1986, 32). Mice carrying the transgene were identified by Southern blot analysis of tail DNA probed with the entire human EC-SOD cDNA. Transgenic founders were found the first litter screened. These mice were bred with (C57BL/6×C3H)FI to produce offspring for further studies. (In all of the following experiments with the EC-SOD transgenic mice, the nontransgenic mice refer to littermates of the transgenic mice that did not contain the transgene for the human EC-SOD. In experiments in which EC-SOD transgenic mice were not used, wild type (C57BL/6×C3H)FI were used.)

Production of homozycous EC-SOD transgenic mice: Homozygous transgenic mice were produced by an $F_1$ cross of heterozygous transgenic mice. Tail DNA from $F_2$ mice were isolated and treated with RNAase. 10 μg of DNA from each mouse was cut with PstI and then electrophoresed through a 1.2% agarose gel. Southern blot analysis of tail DNA probed with the entire human EC-SOD cDNA was then done. The human EC-SOD cDNA did not cross-react with the mouse EC-SOD gene. Band intensity was compared visually to determine which mice were homozygous, heterozygous, or negative for the human EC-SOD transgene.

ii) Characterization of Transgenic Mice

Northern analysis: Transgenic mice and nontransgenic littermates were killed with an overdose of pentobarbital. Tissues were quickly excised and frozen in liquid nitrogen until ready for further processing. Total RNA was then isolated by the CsCl procedure was described (Sambrook et al, Molecular Cloning: A Laboratory Manual. 3. Cold Spring Harbor, Cold Spring Harbor Laboratory, 1989). Twenty μg of total RNA from the tissues of transgenic mice and nontransgenic littermates and an RNA ladder were then denatured with glyoxal, electrophoresed through a 1.2% agarose gel and blotted to nitrocellulose as described (Sambrook et al, Molecular Cloning: A Laboratory Manual. 3. Cold Spring Harbor, Cold Spring Harbor Laboratory, 1989). The blots were then probed with the entire human EC-SOD cDNA.

Separation of SOD isoenzymes by concanavalin A sepharose chromatography: Tissues taken from 3 mice were weighed, then combined and homogenized in 10 volumes of ice-cold 50 mM potassium phosphate, pH 7.4, with 0.3 M KBr, 3 mM diethylenetriaminepentaacetic acid, and 0.5 mM phenylmethylsulfonyl fluoride. Separation of EC-SOD from CuZn SOD and Mn SOD was accomplished by passing tissue homogenates over a concanavalin A sepharose column as described (Marklund et al, Clin. Chim. Acta 126:4 (1982)).

SOD activity: EC-SOD activity and total SOD activity (CuZn SOD and Mn SOD) remaining after EC-SOD extraction were measured by inhibition of cytochrome C reduction at pH 10, as previously described (Crapo et al, Methods Enzymol. 53:382 (1978)). Total protein was determined by the BCA protein assay (Pierce, Rockford, Ill.). The SOD activities were then expressed as units/mg total protein.

Results i) EC-SOD Transgenic Mice

Figure 1:
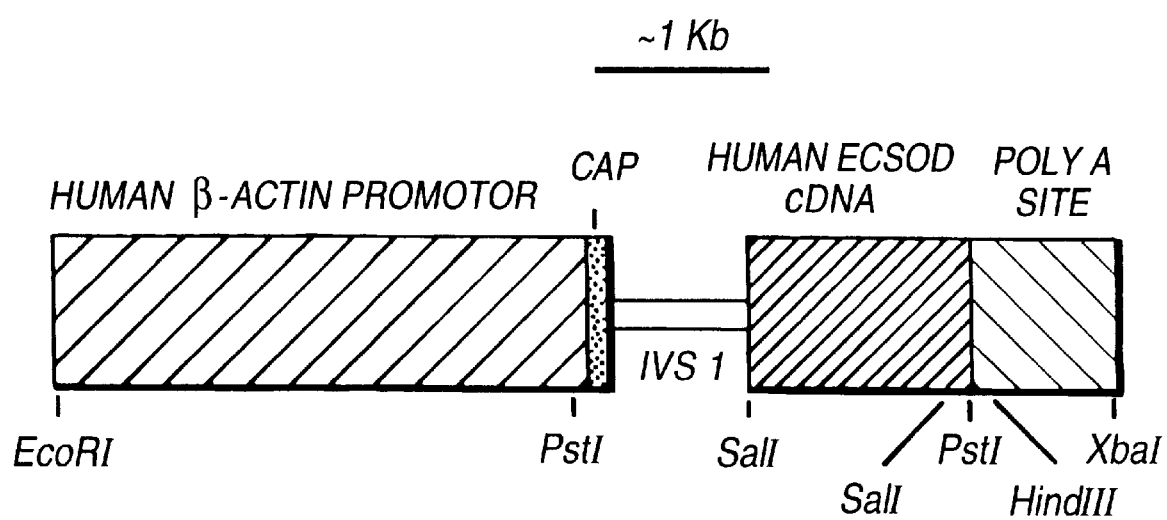
FIG. 1 shows the EC-SOD expression vect:or used to construct transgenic mice. Transgenic mice were generated with the Eco-RI-XbaI fragment. IVS1: Intervening sequence 1 from the human β-actin promoter.
Figure 2:
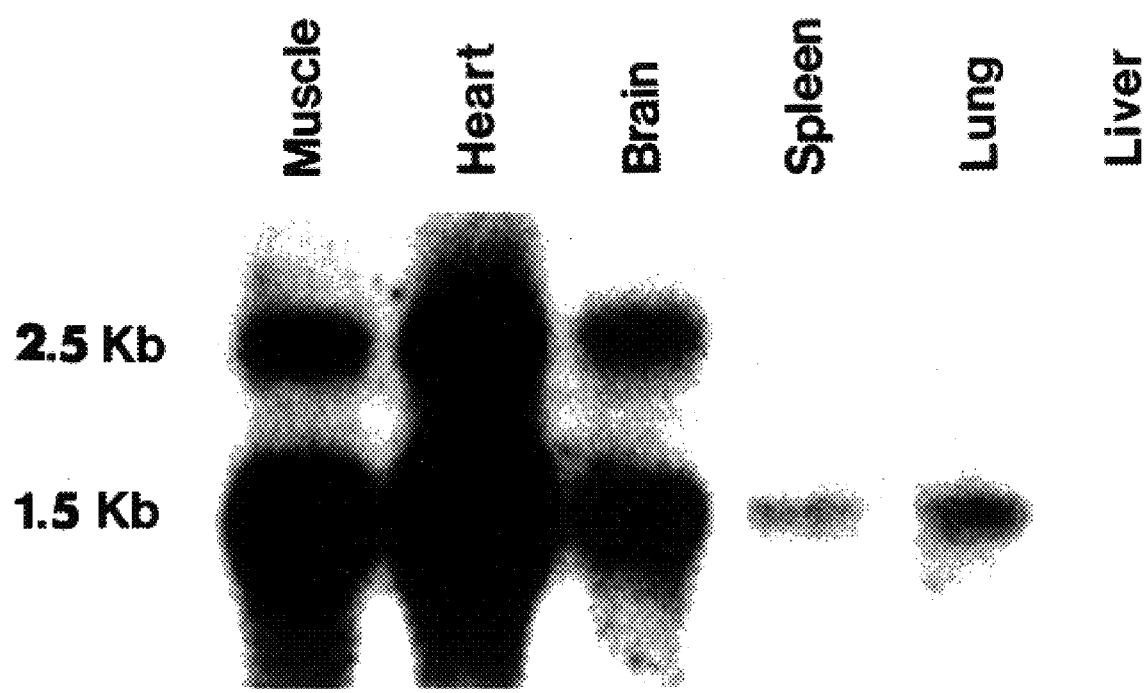
FIG. 2 shows the Northern analysis of tissues from transgenic mice. Twenty μg of total RNA from the tissues of transgenic mice were denatured with gloxal and electrophoresed through a 1.2% agarose gel and blotted onto nitrocellulose. The filter was probed with the entire human EC-SOD cDNA. The 2.5 Kb band corresponds to MRNA of the human EC-SOD transgene containing the 1 Kb intervening sequence (see FIG. 1). The 1.5 Kb band corresponds to the fully processed mRNA of the human EC-SOD transgene.

Characterization of transcenic mice: Mice carrying the human EC-SOD transgene were detected by Southern blot analysis. Northern analysis of various tissues from the F1 of one mouse found to carry the transgene is shown in FIG. 2. High levels of message for human EC-SOD were detected in the heart, skeletal muscle, and brain of transgenic mice, with little or no message observed in the lung, liver, and spleen. No message was detectable in nontransgenic littermates.

Homozygous mice were generated by breeding two heterozygous F1 mice. Homozygous mice were detected by differential band intensities found using Southern blot analysis of equal amounts of PstI digested DNA from the offspring. EC-SOD activity in the mice was found to increase in response to the total copies of the EC-SOD transgene (Table I).

TABLE I

EC-SOD activity in tissues of nontransgenic,
heterozygous transgenic, and homozygous transgenic mice.
Tissues from 3 mice were combined for each measurement.
Activity is expressed as Units/g tissue wet weight.

| Tissue | Nontransgenic | Heterozygous | Homozygous |
|---|---|---|---|
| Brain | 18 | 38 | 50 |
| Heart | 35 | 69 | 102 |

EXAMPLE II

Central Nervous System Oxygen Toxicity

Protocols

Oxygen exposures: 7–8 week old mice were exposed to hyperbaric oxygen five at a time in a small-animal chamber (Bethlehem, Pa.). After flushing the chamber with pure oxygen, compression to 50 meters (6 ATA) was performed within 5 minutes. The oxygen concentration in the chamber was monitored continuously with a Servomex oxygen analyzer (model 572, Sybron, Norwood, Mass.) and maintained at $\geq 99\%$. The carbon dioxide concentration was analyzed from intermittent samples of chamber gas with an IR detector (IR Industries, Santa Barbara, Calif.) and was not allowed to rise above 0.1%. The chamber temperature was maintained at 25–26° C., but the compression of oxygen in the chamber raised the temperature to 30–32° C. transiently, but an environmental control system restored the normal chamber temperature within 3 minutes. The exposures lasted 25 to 75 minutes and were followed by decompression for 5 minutes. The mice were observed continuously for signs of oxygen toxicity from the beginning of the exposure until 4 hours after removal from the chamber. The time to the first generalized convulsion (seizure latency) and the time to death were recorded. These exposure conditions are designed to cause CNS oxygen toxicity without appreciable evidence of pulmonary oxygen toxicity.

Treatment with diethyldithiocarbamate: One hour prior to exposure to 6 ATA oxygen, mice were given either i.p. injections of either 0.008 cc/g saline or 400 mg/kg diethyldithiocarbamate dissolved in normal saline (0.008 cc/g). The mice were then exposed to 6 ATA oxygen for 25 mintues as described above.

To determine the extent of EC-SOD and CuZn SOD inhibition by diethyldithiocarbamate, mice were given diethyldithiocarbamate and sacrificed one hour later. The brains were removed and assayed for EC-SOD and CuZn SOD activity as described above.

Treatment with β-mercaptoethanol: One hour prior to exposure to 6 ATA oxygen, mice were given either i.p. injections of 0.008 cc/g saline or 180 mg/kg β-mercaptoethanol (0.008 cc/g). This dose of β-mercaptoethanol was selected because it contains an equal number of reducing thiols as the dose of diethyldithiocarbamate. The mice were then exposed to 6 ATA oxygen for 30 minutes as described above.

Treatment with N-ω-nitro-L-arginine, an inhibitor of nitric oxide synthase: Ten minutes prior to beginning compression, 0.008 cc/g saline or 20 mg/kg (0.008 cc/g) N-ω-nitro-L-arginine dissolved in sterile water was given i.p to the transgenic and nontransgenic mice. Mice were then exposed at 6 ATA oxygen for 25 or 75 minutes as described above.

Statistical analysis: A paired Student's t-test was used to compare enzyme activities in transgenic and nontransgenic mice. A $\chi^2$ test with Bonferroni correction was used to assess significance in survival differences to hyperbaric exposures. Analysis of variance with a Scheffe F-test was used to compare differences in seizure latency in the different groups of mice.

Results

Figure 3:
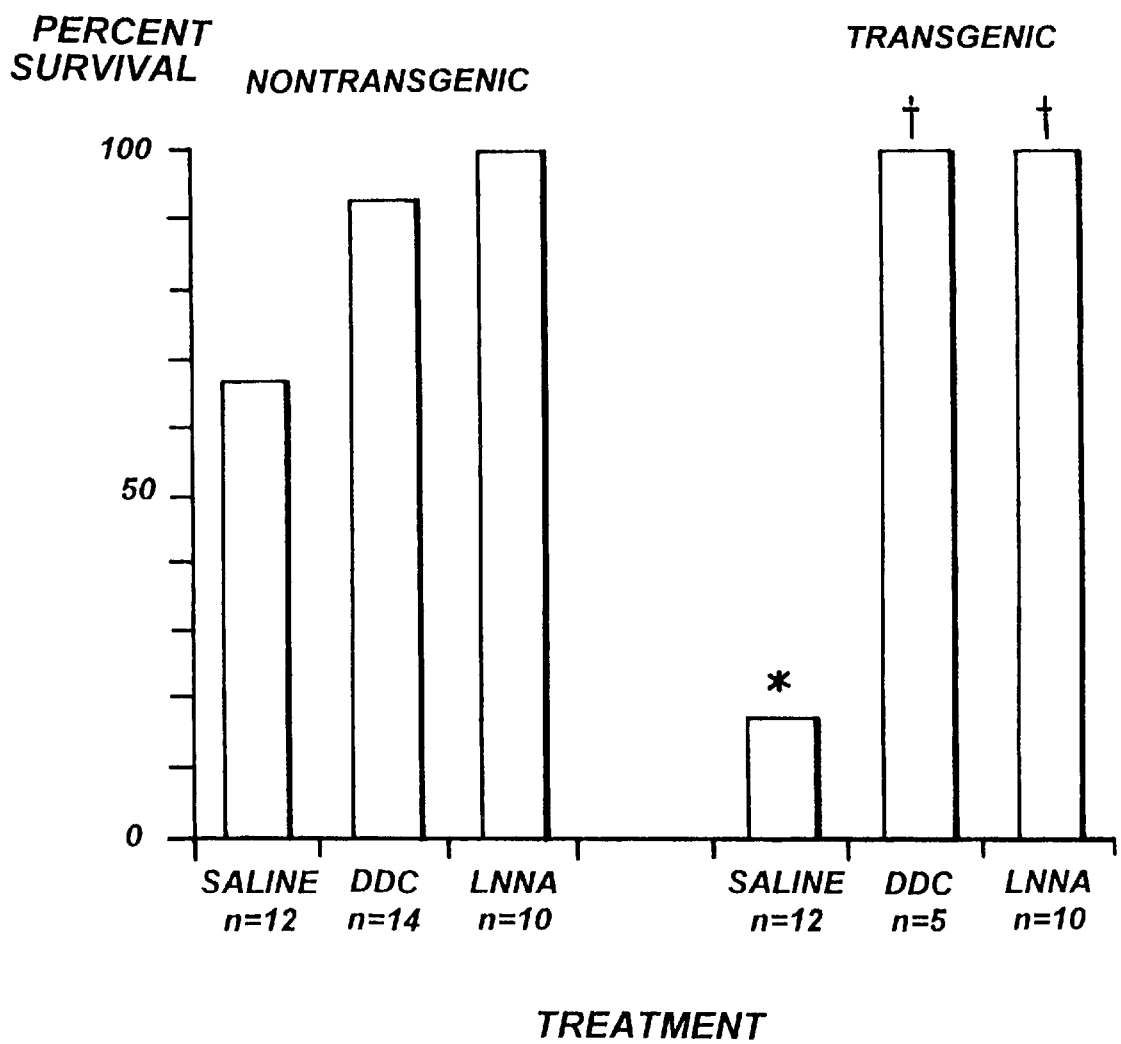
FIG. 3 shows the percent survival of transgenic and nontransgenic mice exposed to 6 ATA oxygen for 25 minutes. Mice were injected with saline or given 20 mg/kg N-ω-nitro-L-arginine (LNNA) i.p. 10 minutes before compression. 400 mg/kg of diethyldithiocarbamate (DDC) in saline was injected i.p. 55 min before compression. $*p<0.017$ tested by $\chi^2$ with Bonferroni correction, compared to transgenic saline treated mice.

Hyperbaric oxygen exposures: To test the effects of increased brain EC-SOD levels on CNS oxygen toxicity, both transgenic and nontransgenic mice (see Example I) were exposed to 6 ATA oxygen for 25 minutes. Transgenic mice were more susceptible (83% mortality) to CNS oxygen toxicity than nontransgenic mice (33& mortality) (FIG. 3).

Figure 4:
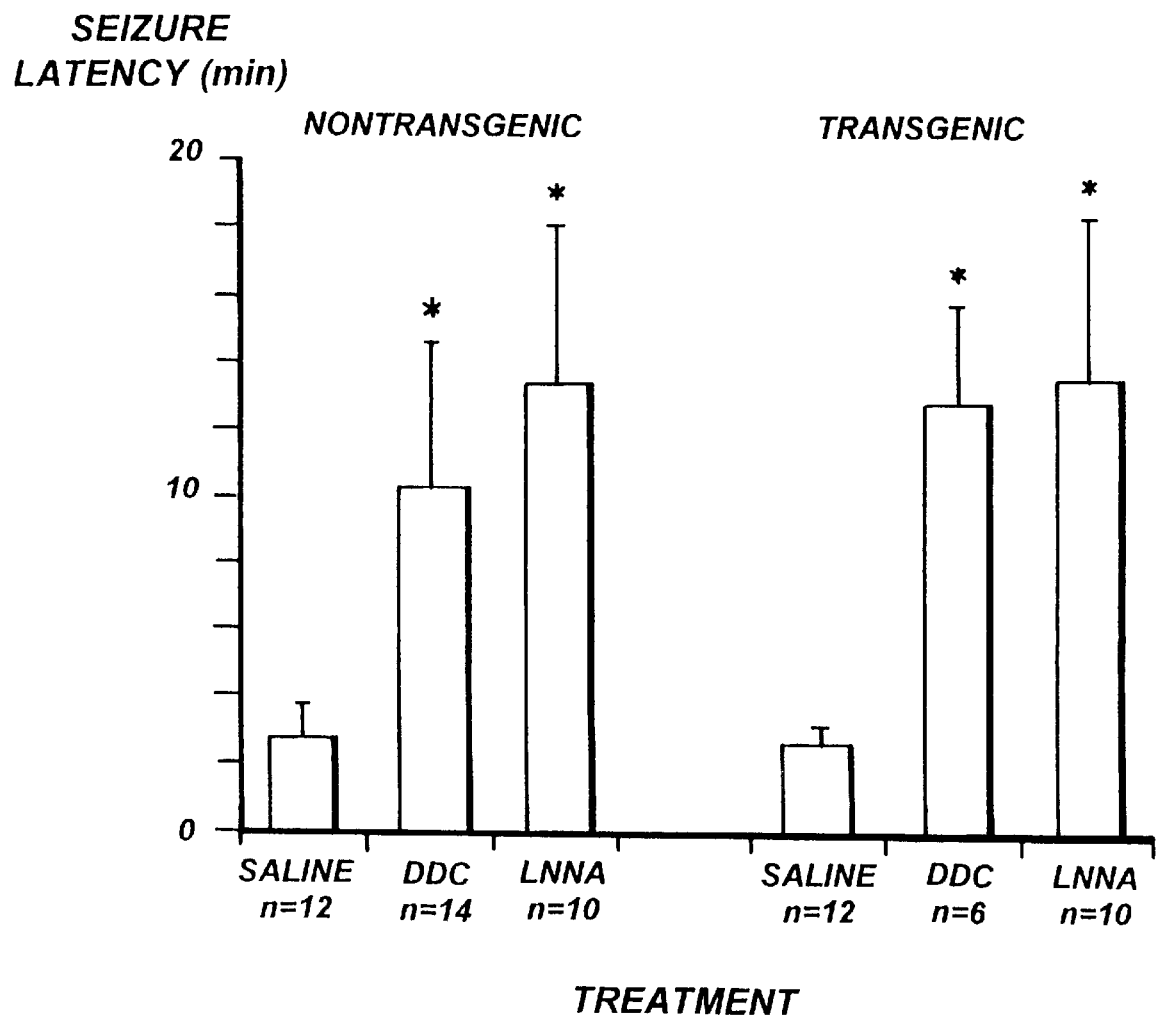
FIG. 4 shows time to onset of first seizure in transgenic and nontransgenic mice exposed to 6 ATA oxygen. Mice were injected with saline or given 20 mg/kg N-ω-nitro-L-arginine (LNNA) i.p. 10 minutes before beginning compression. 400 mg/kg diethyldithiocarbamate (DDC) was injected i.p. 55 minutes prior to compression. Results are expressed as mean ±S.D. of time to first seizure with zero time taken once chamber reached 6 ATA. $*p<0.05$ tested by analysis of variance with the Scheffe F-test compared to nontransgenic saline treated mice.

Transgenic and nontransgenic mice were subsequently treated with an inhibitor of CuZn SOD, diethyldithiocarbamate, to confirm that the increased sensitivity of transgenic mice to CNS oxygen toxicity was the result of increased SOD activity. In both transgenic and nontransgenic mice, treatment with 400 mg/kg diethyldithiocarbamate resulted in 80% inhibition of EC-SOD and 60% inhibition of CuZn SOD in the brain. This is consistent with previous findings (Frank et al, Biochem. Pharmacol. 27:251 (1978); Heikkila et al, J. Biol. Chem. 251:2182 (1976). Treatment with diethyldithiocarbamate conferred increased resistance to CNS oxygen toxicity for both transgenic and nontransgenic mice. Survival increased to 100% in transgenic mice and 93% in nontransgenic mice (FIG. 3). The onset of seizures was also delayed four-fold in mice treated with diethyldithiocarbamate (FIG. 4).

Figure 5:
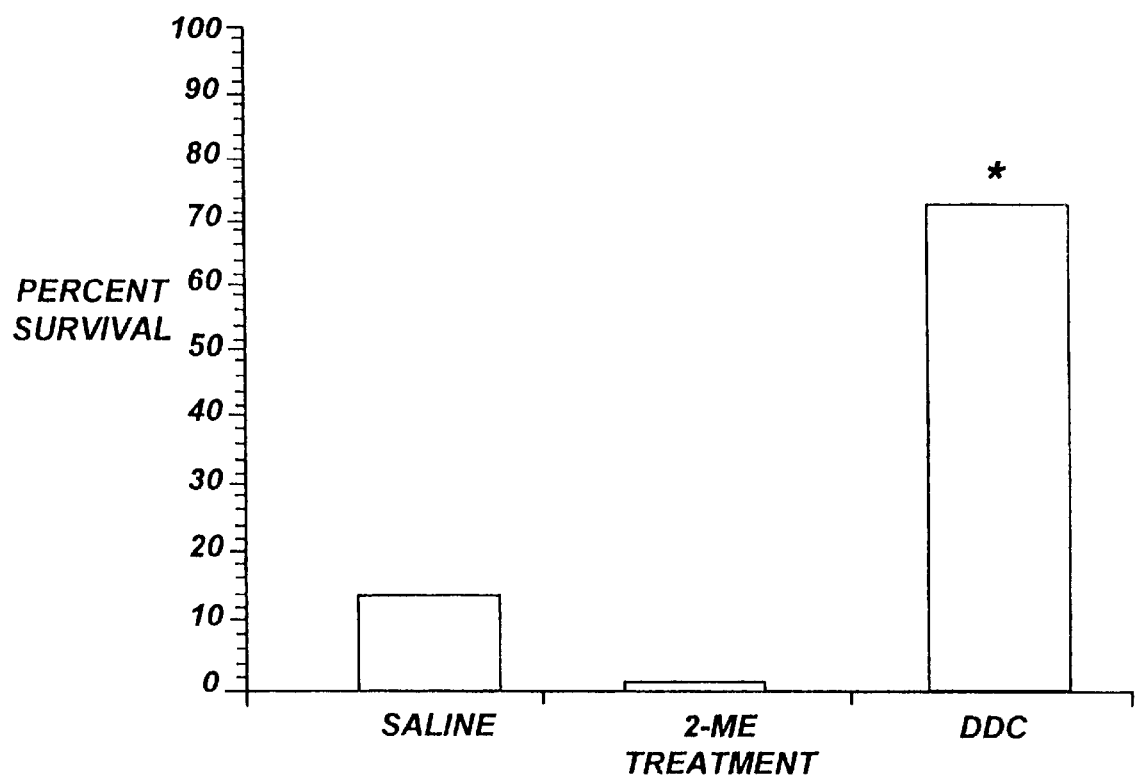
FIG. 5 shows the effect of diethyldithiocarbamate and β-mercaptoethanol on survival in 6 ATA oxygen for 30 minutes. (C57BL/6×C3H)F1 mice were injected i.p. with saline, 180 mg/kg β-mercaptoethanol (2-ME), or 400 mg/kg diethyldithiocarbamate (DDC) in saline 55 min. before compression. $*p<0.025$ tested by $\chi_2$ with Bonferroni correction compared to saline treated mice.

To evaluate whether or not diethyldithiocarbamate protects against CNS oxygen toxicity by acting as a reducing agent rather than as an inhibitor of SOD activity, mice were treated with an equimolar amount of reducing thiols in the form of β-mercaptoethanol and exposed to hyperbaric oxygen. FIG. 5 shows that β-mercaptoethanol did not protect against CNS oxygen toxicity.

Figure 6:
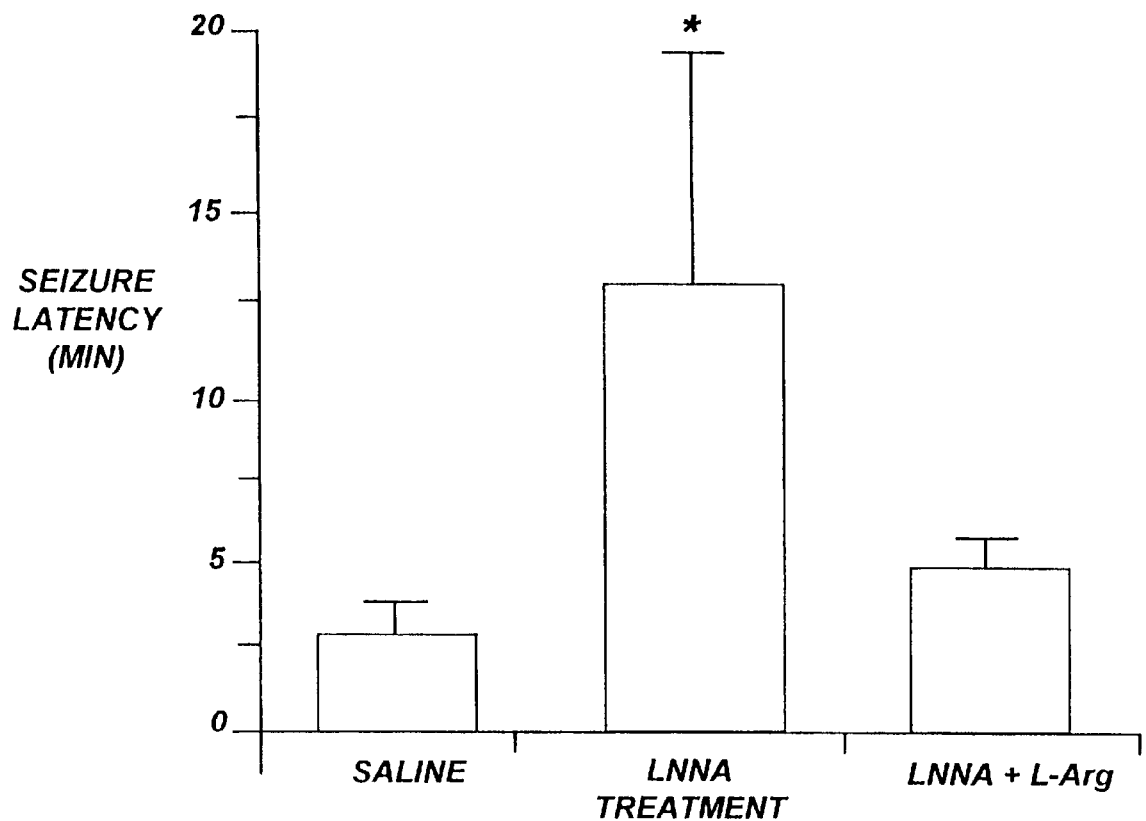
FIG. 6 shows the seizure latency in wild-type mice exposed to 6 ATA oxygen after being treated with saline or 20 mg/kg N-ω-nitro-L-arginine (LNNA) or 20 mg/kg N-ω-nitro-L-arginine plus 50 mg/kg L-arginine (LNNA+L-Arg). $*p<0.05$ tested by analysis of variance with a paired Student's t-test compared to saline treated mice.
Figure 7:
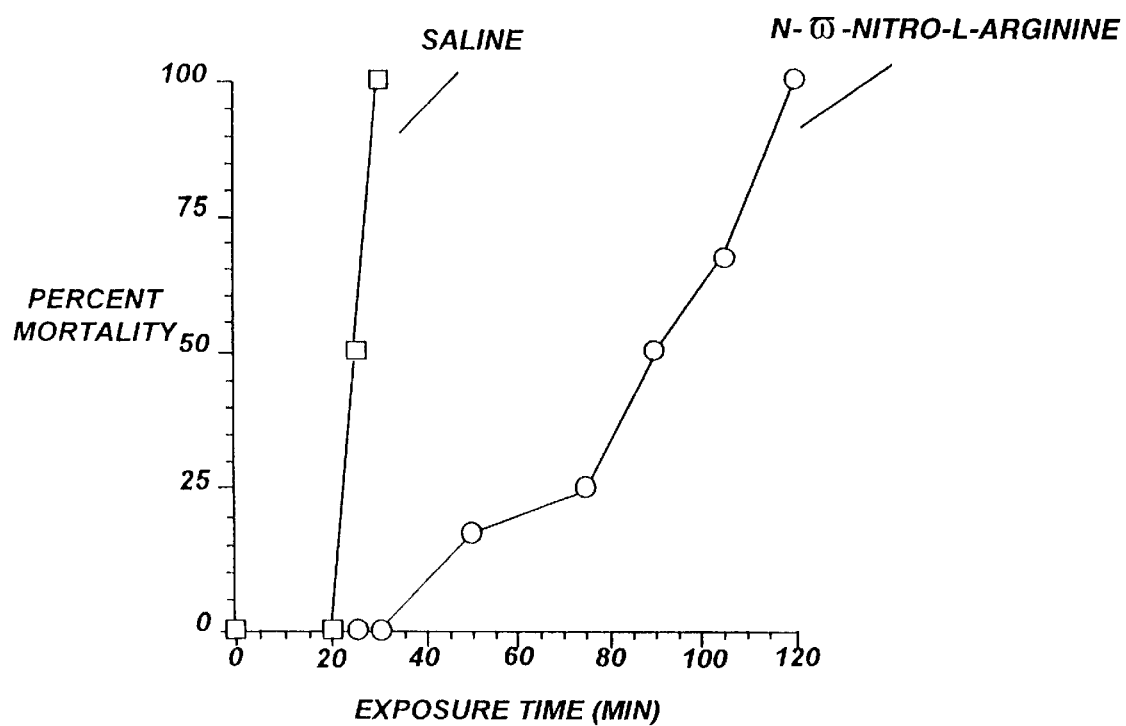
FIG. 7 shows the percent survival in wild-type mice exposed to 6 ATA oxygen. Mice were given an i.p. injection of normal saline (0.008 cc/g) or 20 mg/kg N-ω-nitro-L-arginine (LNNA) (0.008 cc/g) 15 minutes prior to compression. The mice were exposed to 6 ATA of oxygen for 20 minutes (n=10, saline only), 25 minutes (n=10, both groups), 30 minutes (n=10, saline only), 50 minutes (n=6, LNNA only), 75 minutes (n=12, LNNA only), 90 minutes (n=14, LNNA only), 105 minutes (n=6 LNNA only) and 120 minutes (n=6, LNNA only) and percent survival was measured for each group.
Figure 8:
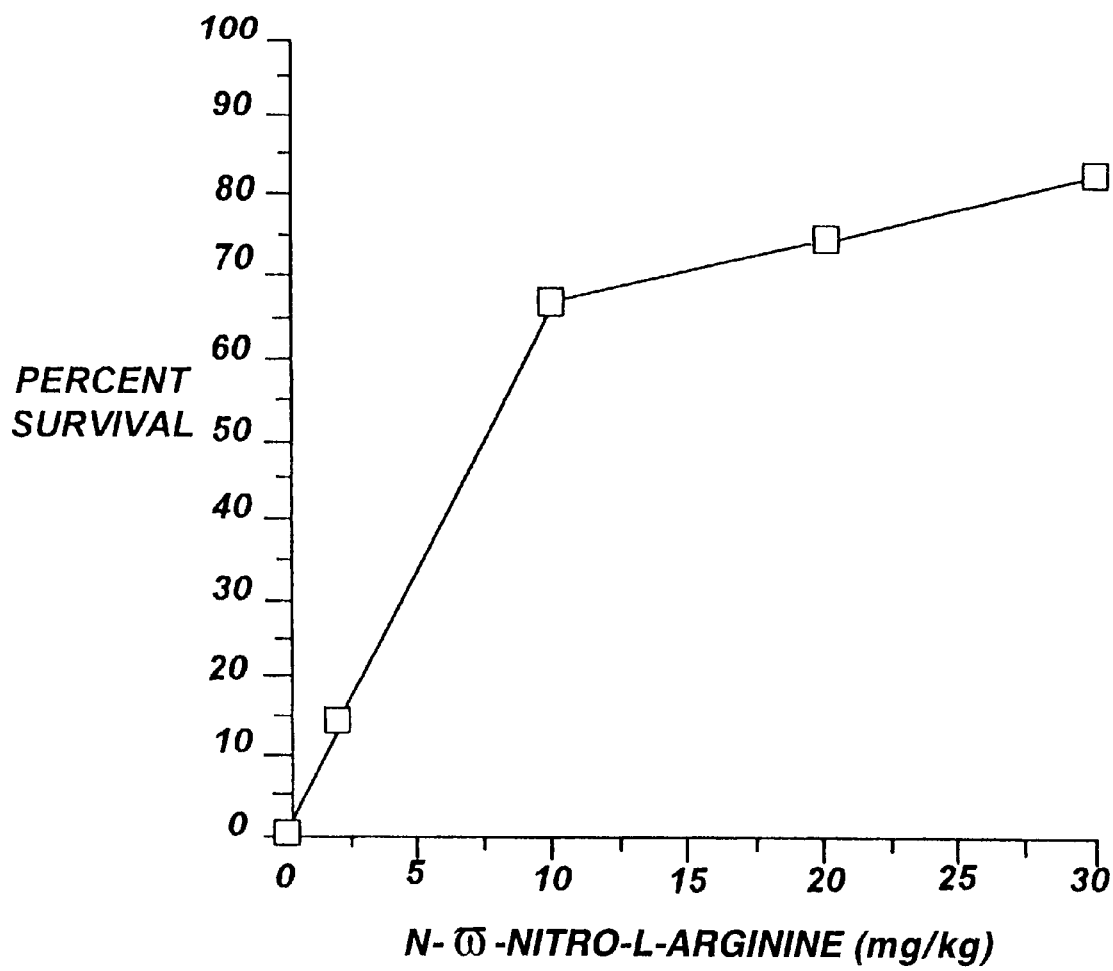
FIG. 8 shows the survival dose response curve for N-ω-nitro-L-arginine (LNNA). Wild-type mice were given an i.p. injection of normal saline (0.008 cc/g) or 0, 2, 10, 20, or 30 mg/kg LNNA (0.008 cc/g) 15 minutes prior to compression and then exposed to 75 minutes at 6 ATA oxygen. Percent survival was calculated for each treatment group.
Figure 9:
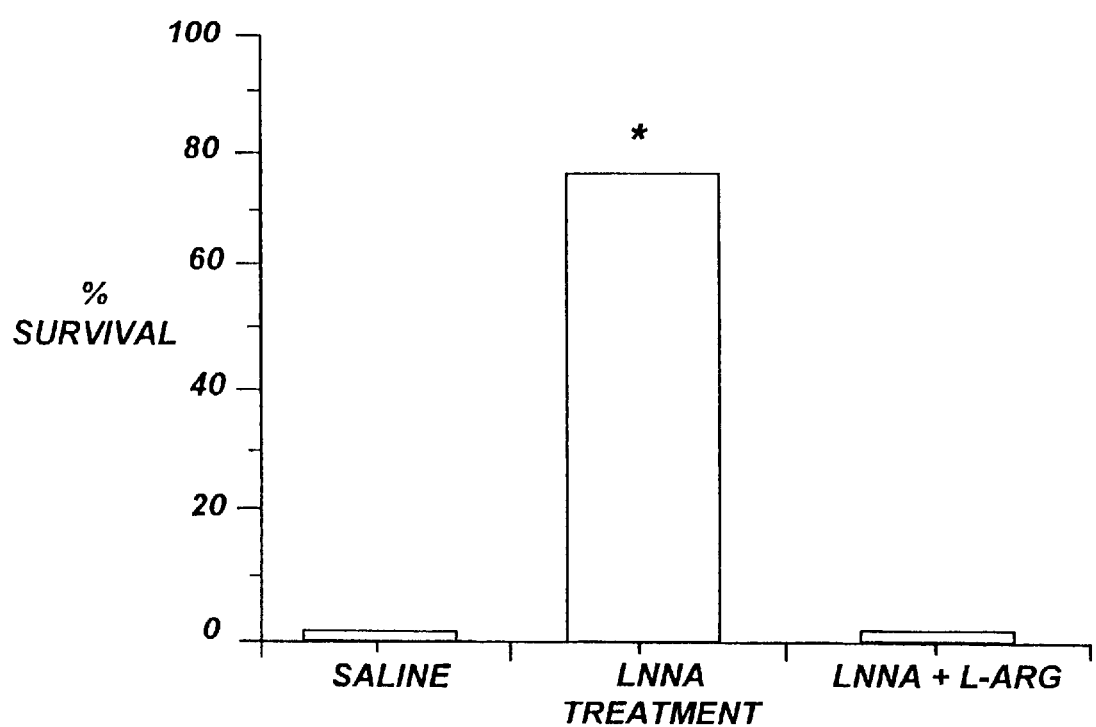
FIG. 9 shows the percent survival in wild-type mice pretreated with saline, 20 mg/kg N-ω-nitro-L-arginine (LNNA), or 20 mg/kg N-ω-nitro-L-arginine plus 50 mg/kg L-arginine (LNNA+L-Arg) and then exposed to 75 minutes of 6 ATA oxygen. $*p<0.05$ tested with a $\chi$-square test with Bonferroni correction.

One possibility that might explain why EC-SOD exacerbates CNS oxygen toxicity would be that nitric oxide is a mediator of CNS oxygen toxicity and EC-SOD is protecting nitric oxide from superoxide mediated inactivation. To test the hypothesis that nitric oxide contributes to CNS oxygen toxicity, wild-type (C57BL/6×C3H)F1 mice were treated with an inhibitor of nitric oxide synthase, N-ω-nitro-L-arginine. FIG. 6 shows the effects of N-ω-nitro-L-arginine on seizure latency in mice. Pretreatment with N-ω-nitro-L-arginine resulted in a significant increase in seizure latency (13.50±5.6 min) when compared to saline treated mice (2.75±1 min). FIG. 7 shows that nitric oxide synthase inhibition also significantly increased survival after exposure to hyperbaric oxygen. Mice given the inhibitor of nitric oxide synthase displayed 50% mortality after exposure to 90 minutes of 6 ATA oxygen and 100% mortality was not obtained until after 2 hours of this exposure. Saline treated mice, however, had a 50% mortality after only 25 minutes of exposure, with 100% mortality after only 30 minutes at 6 ATA of oxygen. FIG. 8 shows that the percent survival in hyperbaric oxygen was dependent on the dose of the inhibitor given. The protection offered by this competitive inhibitor of nitric oxide synthase could be reversed when an excess of L-arginine was given (FIG. 6 and FIG. 9).

Figure 10:
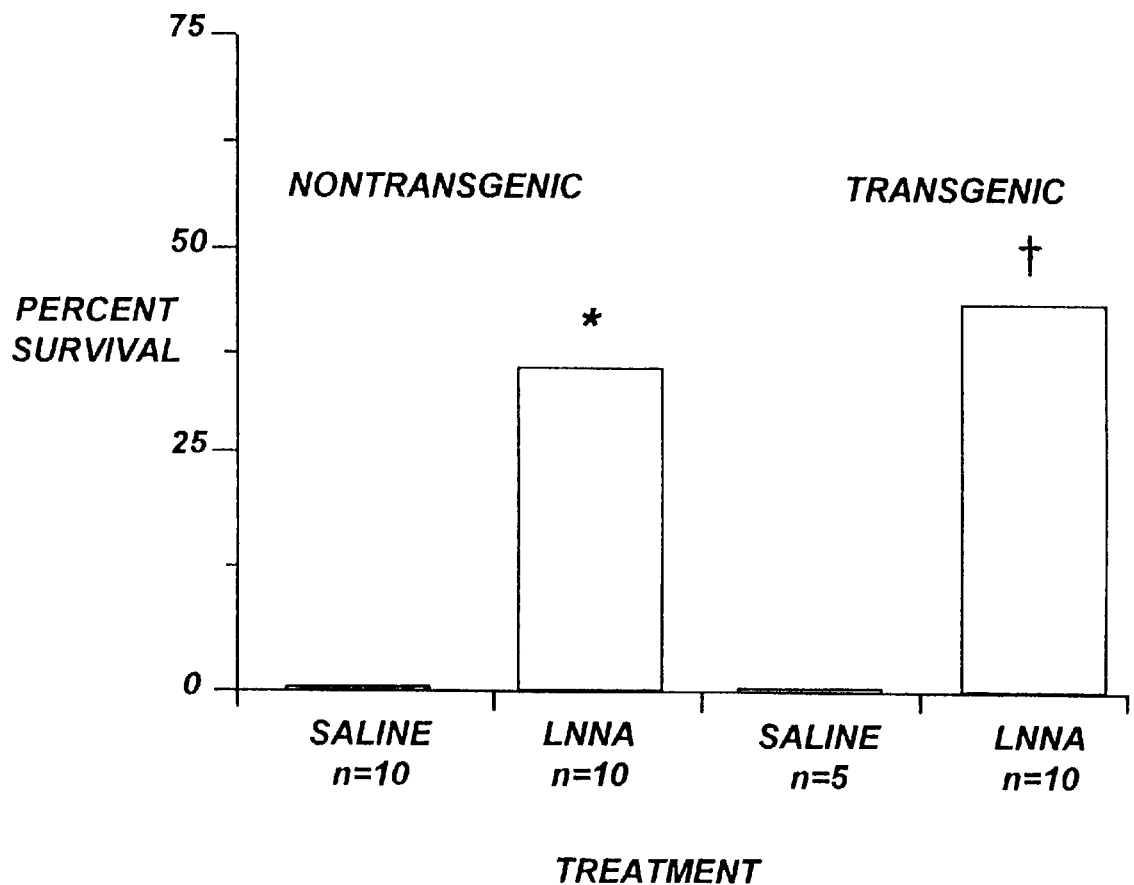
FIG. 10 shows the percent survival in transgenic and nontransgenic mice exposed to 6 ATA oxygen for 75 minutes. Mice were injected with saline or given 20 mg/kg N-ω-nitro-L-arginine (LNNA) i.p. 10 minutes before compression. $*p<0.05$ tested by $\chi^2$ compared to nontransgenic saline treated mice. $+p<0.05$ tested by $\chi^2$ compared to transgenic saline treated mice.

The effects of the nitric oxide synthase inhibitor, N-ω-nitro-L-arginine, upon CNS oxygen toxicity was then studied in the transgenic mice. This treatment dramatically reduced CNS oxygen toxicity in both transgenic and nontransgenic mice. Survival after a 25 minute exposure to 6 ATA oxygen increased to 100% in both groups (FIG. 3). Seizure latency was also significantly delayed (FIG. 4). The exposure time was then increased to 75 minutes to investigate whether transgenic mice were still more sensitive than nontransgenic mice to hyperbaric oxygen. The results in FIG. 10 indicate that treatment with N-ω-nitro-L-arginine abolished the difference in sensitivity that was observed between untreated transgenic and nontransgenic mice during the 25 minute exposure shown in FIG. 3.

EXAMPLE III

Cold-Induced Brain Edema

Protocols

Injury model: Young (6–7 week) mice (see Example I) were anesthetized with 60 mg/kg pentobarbital (Nembutal, Abbott Laboratories, Chicago, Ill.). An incision was then made in the scalp and a steel rod 20 cm long, 3 mm in diameter, equilibrated in liquid nitrogen with an 8 cm bath of liquid nitrogen 4 cm from the end of the rod, was placed on the skull over the right cerebral hemisphere for 30 seconds. The skin incision was then sutured.

Two hours after the injury the mouse was given an additional dose of pentobarbital. The chest cavity was opened, the lungs were excised, and the mouse was then perfused with 20 ml saline through the left ventricle of the heart. The brain was then removed and the cerebellum was excised. The right (R) and left (L) cerebral hemispheres were separated and immediately weighed (wet weight, W). Each hemisphere was then dried at 70° C. for 2–3 days in a hot air oven until a constant weight was achieved (dry weight, D). An index of edema (I) was then calculated as shown in equation 13.

$$I = (W/D\ R - W/D\ L)/(W/D\ L) \times 100 \quad [13]$$

This calculation allowed the left hemisphere to serve as an internal control for the injured right hemisphere in each mouse.

Chemical treatments: Six groups of experiments were conducted to investigate the importance of extracellular superoxide, iron, and nitric oxide in cold-induced brain edema. In all groups, drugs were dissolved in saline and injected at 0.008 cc/g 15 minutes prior to cold injury. In Group 1, edema formation of EC-SOD transgenic mice was compared with that of nontransgenic littermates. Group 2 compared edema formation between wild-type (C57BL/6× C3H)F1 mice treated with saline and (C57BL/6×C3H)F1 mice treated with 0.33 mg/g deferoxamine (0.51 μmoles/g). Group 3 compared (C57BL/6×C3H)F1 mice treated with saline to (C57BL/6×C3H)F1 mice treated with 0.51 μmoles/g $Fe^{3+}$-saturated deferoxamine. Group 4 consisted of (C57BL/6×C3H)F1 mice treated with saline and (C57BL/6×C3H)F1 mice treated with 0.02 mg/g N-ω-nitro-L-arginine methyl ester. Group 5 consisted of (C57BL/6×C3H)F1 mice treated with saline and (C57BL/6×C3H)F1 mice treated with 0.02 mg/g N-ω-nitro-L-arginine methyl ester plus 0.05 mg/g L-arginine. Group 6 compared edema formation between nontransgenic mice, EC-SOD transgenic mice treated with saline, and EC-SOD transgenic mice treated with 0.02 mg/g N-ω-nitro-L-arginine methyl ester.

Iron saturated deferoxamine was made by dissolving equimolar amounts of deferoxamine and then ferric chloride in saline. Saturation of deferoxamine with ferric iron was determined spectrophotometrically be measuring the absorbance at 425 nm ($\epsilon = 2500\ M^{-1}\ cm^{-1}$ for $Fe^{3+}$-deferoxamine) (Monzyk and Crumbliss, J. Amer. Chem. Soc. 104:4921 (1982)).

Evan's blue treatment: One hour and 50 minutes after cold injury, 5 ml/kg of 1% Evan's Blue in saline was injected into the femoral artery of transgenic and nontransgenic mice. The mice were sacrificed 10 minutes later. The lungs were then excised and the mice were then perfused with normal saline through the left ventricle until there was no more blue color in the effluent. The brains were then removed and photographed.

Statistical analysis: A paired Student's t-test was used to compare significance of edema development compared to nontransgenic mice or saline treated mice for each of the groups examined. Analysis of variance with a Fisher PLSD test was used to compare significance in Group 6. P-value less than 0.05 were considered to be significant.

Results

Figure 11:
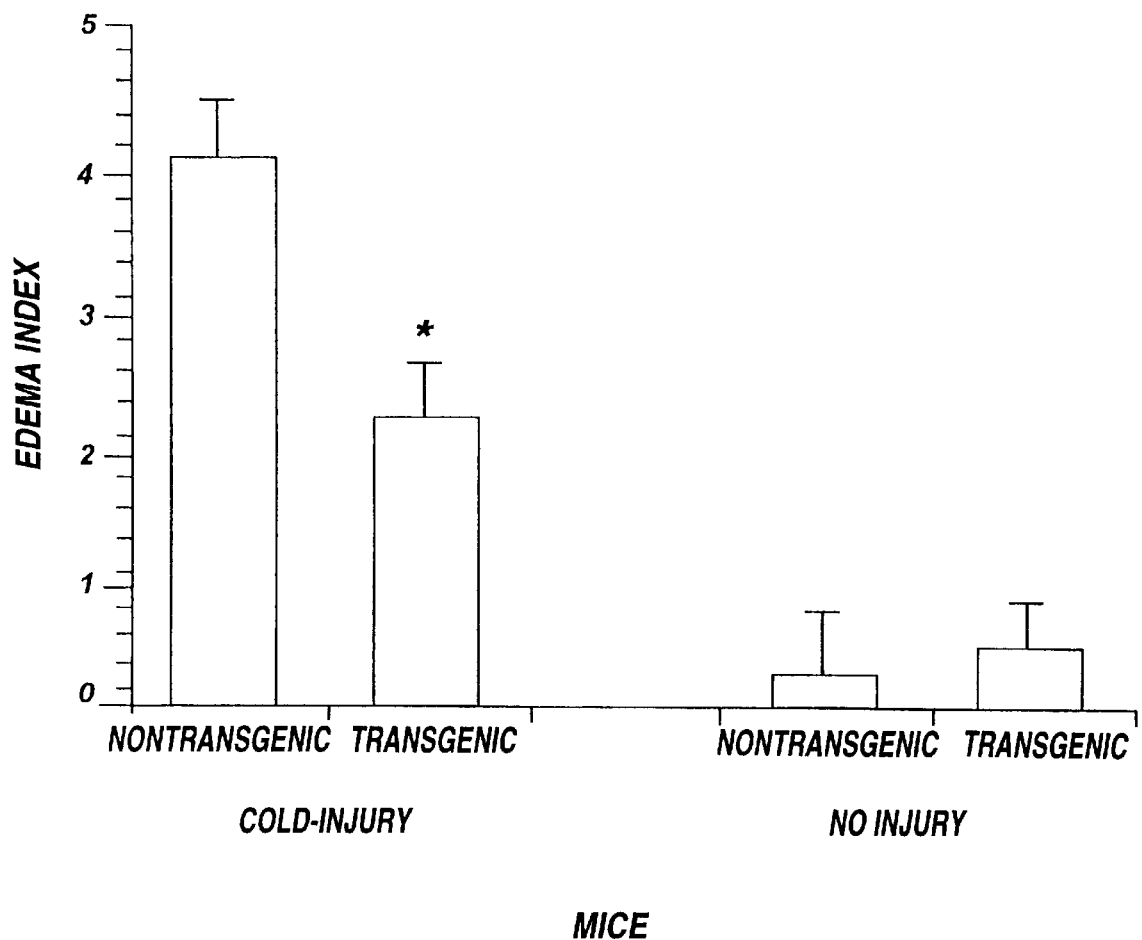
FIG. 11 shows the comparison of edema formation in EC-SOD transgenic mice to edema formation in nontransgenic littermates after cold-induced injury to the right cerebral hemisphere as well as in non-injured mice. Values are presented as mean±standard error. $*p<0.05$ compared to Edema Index of respective nontransgenic controls using a paired Student's t-test.
Figure 12:
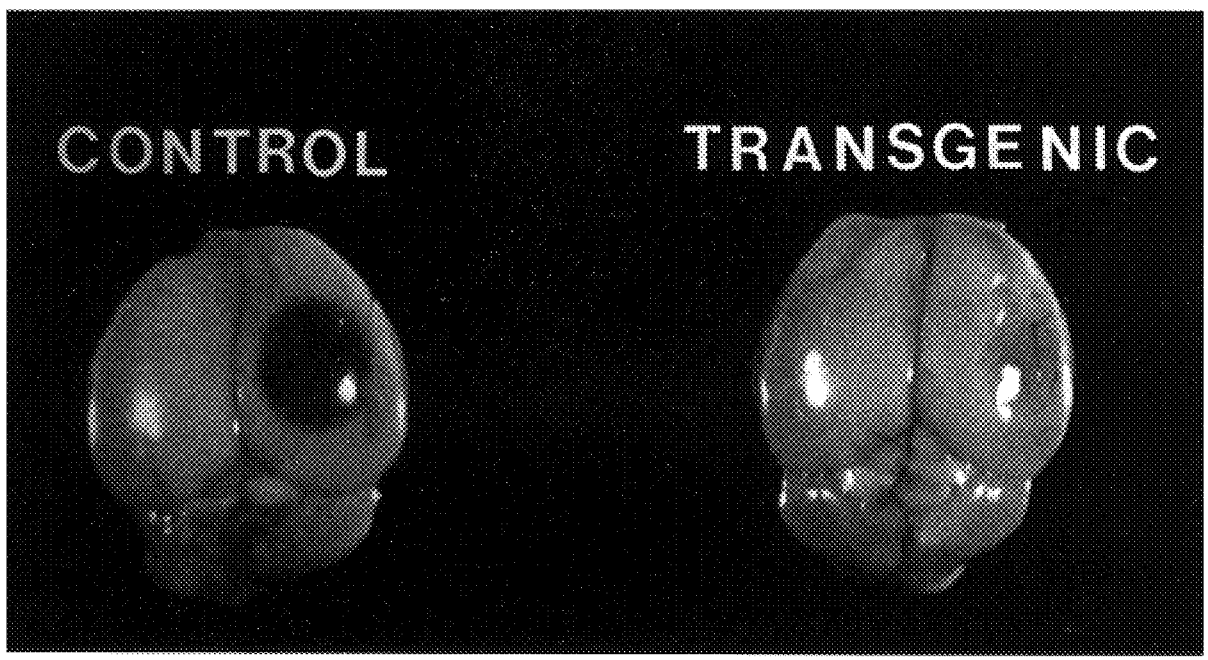
FIG. 12 shows the effect of augmented levels of EC-SOD on vascular permeability changes after cold-induced brain injury. Vascular permeability is demonstrated as Evan's blue leakage in the injuried right cerebral hemispheres of nontransgenic (control) and EC-SOD transgenic mice.

Cold-induced Brain Edema: When transgenic mice and nontransgenic littermates were subjected to cold-induced injury to the right cerebral hemisphere it was found that the transgenic mice were significantly protected against edema formation compared to nontransgenic littermates (FIG. 11). Percent edema was 44% less in transgenic mice then in nontransgenic littermates and Evan's blue dye extravasation was visibly less in transgenic mice compared to nontransgenic littermates (FIG. 12).

To test the contribution of iron to edema formation in this model, mice were pretreated with i.p. injections of deferoxamine or saline prior to cold-induces injury. Table II shows that pretreatment with deferoxamine resulted in 43% less edema formation compared to mice only given saline. Mice were then pretreated with i.p. injections of iron-saturated deferoxamine or saline before cold-induced injury to see if the iron chelating properties of this compound were truly necessary for protection against edema formation. Table IV shows that, even when deferoxamine was saturated with iron, it was still capable of protecting against edema formation and resulted in 32–48% less edema than that found in saline treated controls. The absolute values for the edema index were found to quite variable, however, repeated experiments consistently show the same signficant trends in protection against edema formation in the various treatments examined.

TABLE II

Evaluation of the effect of the ferric iron chelator deferoxamine on edema formation after cold-induced brain injury. Wild-type (C57BL/6 X C3H) F1 mice were treated with deferoxamine to determine what effect the iron chelating properties of this compound had on edema formation. Values are presented as mean ± standard error.

| Treatment | n | Edema Index |
|---|---|---|
| Saline | 7 | 5.92 ± 0.62 |
| Deferoxamine | 7 | 3.41 ± 0.49* |
| Run 1: | | |
| Saline | 6 | 8.24 ± 0.53 |
| Fe-Deferoxamine | 6 | 5.63 ± 0.63* |
| Run 2: | | |
| Saline | 5 | 7.65 ± 1.30 |
| Fe-Deferoxamine | 5 | 3.97 ± 0.59* |

*$p < 0.05$ compared to Edema Index of respective saline treated controls using a paired Student's t-test.

These results indicate that deferoxamine is capable of protecting against edema formation by a mechanism independent of its ability to scavenge iron. Because deferoxamine is capable of scavenging both the peroxynitrite anion (Radi et al, Arch. Biochem. Biophys. 288(2):481 (1991)) as well as the hydroxyl racical (Hoe et al, Chemico-Biological Interactions 41:75 (1982)), it was hypothesized that it is these properties of deferoxamine that enable it to protect against vasogenic edema.

To test this hypothesis, the synthesis of nitric oxide was inhibited with N-ω-nitro-L-arginine methyl ester, a competitive inhibitor of the enzyme ritric oxide synthase, to determine if this would result in protection against edema formation after a cold-induced injury. Table III shows that treatment with N-ω-nitro-L-arginine methyl ester significantly protected mice against edema formation resulting in 37% less edema formation than that occurring in saline treated controls. This protection by N-ω-nitro-L-arginine methyl ester was reversed by simultaneous administration of an excess of L-arginine to the mice (Table III).

TABLE III

The effect of inhibition of nitric oxide synthesis on edema formation after cold-induced brain injury. Wild-type (C57BL/6 X C3H) F1 mice were treated with the competitive inhibitor of nitric oxide synthase, N-ω-nitro-L-arginine methyl ester (LNAME) to determine what effect nitric oxide had on vasogenic edema. Mice were also given N-ω-nitro-L-arginine methyl ester plus an excess of L-arginine (LNAME + L-Arg) to see if the effects seen with LNAME alone could be reversed. Values are presented as mean ± standard error.

| Treatment | n | Edema Index |
|---|---|---|
| Saline | 6 | 5.77 ± 0.29 |
| LNAME | 6 | 3.65 ± 0.51* |
| Saline | 6 | 6.56 ± 0.21 |
| LNAME + L-Arg | 6 | 6.03 ± 0.71 |

*$p < 0.05$ compared to Edema Index of respective saline treated controls using a paired Student's t-test.

In the final experiments, EC-SOD transgenic mice were treated with either saline or N-ω-nitro-L-arginine methyl ester to determine if there was an additive effect in preventing edema formation in mice which have both increased levels of EC-SOD as well as the inhibitor of nitric oxide synthase. Table IV shows that when EC-SOD transgenic mice were given the inhibitor of nitric oxide synthase, no added protection against edema formation was detected relative to transgenic mice protected only by increased levels of EC-SOD in the brain.

TABLE IV

Evaluation of the effect of inhibition of nitric oxide synthesis on edema formation in transgenic mice. Comparison of edema formation in nontransgenic mice to edema formation in transgenic mice with elevated levels of brain EC-SOD activity, and to edema formation in transgenic mice treated with an inhibitor of nitric oxide synthesis (20 mg/kg N-ω-nitro-L-arginine; Transgenic + LNAME) 15 minutes prior to cold-induced injury. Values are presented as mean ± standard error and were compared using analysis of variance with a Fisher PLSD test. No significant difference was seen between transgenic and transgenic + LNAME mice.

| Treatment | n | Edema Index |
|---|---|---|
| Nontransgenic | 6 | 7.91 ± 0.67 |
| Transgenic | 6 | 4.91 ± 0.78* |
| Transgenic + LNAME | 6 | 4.30 ± 0.96* |

*$p < 0.05$ compared to Edema Index of nontransgenic mice.

EXAMPLE IV

Immunolocalization of EC-SOD

Protocols

Human lung: Five human lung samples were obtained to evaluate the distribution of EC-SOD in human lung tissue. One sample was obtained from a surgical pathology specimen of a right upper lobe resected from a 43 year old white female with a 50 pack year smoking history (equivalent to one pack per day for one year) and a solitary nodule found on chest X-ray. The patient was diagnosed with squamous cell carcinoma. Tissue from a region not involved in the carcinoma from this lobe was used in the studies presented here. A second lung was obtained from a right upper lobe surgical pathology specimen resected from a 51 year old white male with a 60 pack year smoking history found to have an isolated nodule on X-ray. The patient had no other illness and was diagnosed with squamous cell carcinoma. Lung tissue not involved in the carcinoma from this specimen was used for the localization of EC-SOD. A third lung was obtained from a rapid autopsy (tissue obtained 6 hours after death) of a 66 year old white male with dementia, but no history of smoking or lung disease. The fourth lung examined was obtained from excess lung tissue of a lung too large for the recipient of a lung transplant. The lung was donated from a 45 year old white female with no history of smoking or lung disease. The fifth lung examined in these studies was also from excess lung tissue used for lung transplantation from a 39 year old white male with no history of smoking or lung disease. Notably, no differences in labeling patterns were seen between the surgical pathology specimens, the autopsy tissues from donors for lung transplantation.

The tissues were fixed in 2% paraformaldehyde/0.2% gluteraldehyde in 0.01 M phosphate buffered saline (PBS; 1.2 g $NaH_2PO_4$, 8 g NaCl, 0.2 g KCl, in 1 liter pH 7.3) for 1 hour followed by overnight fixation in 4% paraformaldehyde at 4° C. and then in O.C.T. compound. The tissues were frozen in liquid nitrogen chilled hexane and stored at −70° C. until they were sectioned for light microscopic studies.

For electron microscopic studies, lung tissues were processed as in the light microscopic studies up to the equilibration in sucrose. After equilibration in sucrose, the lung tissues were infiltrated with 10% gelatin at 37° C. for 10 minutes. The tissue slices, in gelatin, were then solidified on ice, cut into 2 mm/side cubes, and then cryoprotected in 4% polyvinyl alcohol containing 2 M sucrose overnight. These samples were then mounted onto stubs, flash frozen in liquid nitrogen, and then stored in liquid nitrogen until they were sectioned for electron microscopic studies.

Characterization of antibody to human recombinant EC-SOD: Human recombinant EC-SOD (furnished by S. L. Marklund, Umeä, Sweden; Tibell et al Proc. Natl. Acad. Sci. U.S.A. 84:6634 (1987)) and the 20,000×g supernatant of a human lung homogenate were denatured in the presence of β-mercaptoethanol and sodium dodecyl sulfate by boiling for 5 minutes and then electrophoresed through 12% polyacrylamide gel in the presence of sodium dodecyl sulfate. The protein was then electrophoretically transferred to nitrocellulose. The blot was then incubated with 4.3 µg/ml of an IgG purified fraction of rabbit anti-rh-EC-SOD (furnished by S. M. Marklund, Umeä University Hospital, Umeä, Sweden) affinity purified with rh-EC-SOD followed by incubation with $^{125}$I-protein A and autoradiography.

Absorption of anti-EC-SOD IqG: CNBr activated sepharose was swollen in PBS. Swollen gel was mixed with PBS so that the settled gel occupied 50% of the volume. The gel was suspended and 100 µl was mixed with 100 µg pure rh-EC-SOD for 2 hours at room temperature while gently agitating. The gel was then washed 4 times with PBS+1% bovine serum albumin (BSA) and made up 100 µl with PBS+1% BSA. 100 µl of rabbit anti-rh-EC-SOD at two times the concentration used for immunolabeling was then added and mixed for 2 hours with gentle agitation at room temperature. Non-immune rabbit IgG was then added to the supernatant in a concentration equivalent to the predicted concentration of anti-rh-EC-SOD IgG removed by the procedure. This supernatant was then used for subsequent immunolabeling.

Light microscopic immunohistochemistry: 4 µm serial sections of O.C.T. embedded tissue were cut on a cryostat at −20° C. and put on poly-L-lysine-coated slides (3 sections/slide). Sections were stored at −70° C. until labeling was done. Sections were then labeled for EC-SOD using an indirect immunoperoxidase method (Milde et al, J. Histochem. Cytochem. 37:1609 (1989); Randell et al, Am. J. Respir. Cell. Mol. Biol. 4:544 (1991)) with a biotinylated goat anti-rabbit IgG and streptavidin-horseradish peroxidase (Jackson, ImmunoResearch Laboratoreis (West Grove, Pa.)) (Table V). To reduce background staining, the sections were incubated in 1% $H_2O_2$ in methanol to inactivate endogenous peroxidases, 10 mM borohydride to block aldehydes, and nonspecific binding was blocked by incubation with 5% normal goat serum (NGS), 5% milk, and 1% BSA in PBS. The optimal primary and secondary antibody dilutions were determined empirically and made in PBS with 1% milk plus 1% BSA (milk was not included in the streptavidin solution). The slides were developed using diaminobenzidine (10 mg diaminobenzidine, 50 ml 0.05 M Tris.Cl, pH 7.6, 100 µl 3% $H_2O_2$) and counterstained with 1% methyl green. As a control, serial sections were separately labeled with either rabbit anti-rh-EC-SOD (EC-SOD), non-immune rabbit IgG, or rabbit anti-rh-EC-SOD from which EC-SOD binding IgG had been absorbed out (EC-SOD absorbed; see above).

TABLE V

Staining procedures for light microscopic immunohistochemistry. All incubations were performed in a humidified chamber at room temperature.

| | Incubation | Time |
|---|---|---|
| Step 1 | 1% $H_2O_2$ in methanol | 30 minutes |
| Step 2 | 10 mM borohydride in PBS (gluteraldehyde fixed tissue only) | 30 minutes |
| Step 3 | 5% NGS, 5% milk; 1% BSA/PBS | 30 minutes |
| Step 4 | Primary antibody 1% milk, 1% BSA/PBS (various dilutions) | 1 hour |
| Step 5 | Biotin-labeled goat anti-rabbit IgG (1:6000 in 1% milk, 1% BSA/PBS) | 1 hour |
| Step 6 | Streptavidin-Horse radish peroxidase (1:2000 in 1% BSA/PBS) | 1 hour |
| Step 7 | Diaminobenzidine | 15 minutes |
| Step 8 | 1% Methyl Green in water | 15 minutes |

Electron microscopic immunocytochemistry: Ultrathin cryo sections (70 nm) of human lung tissue were immunolabeled with rabbit anti rh-EC-SOD and 10-nm protein A-gold as prevsiously described (Crapo et al, Proc. Natl. Acad. Sci. U.S.A. 89:10405 (1992)) (Table VI). Briefly, sections were first incubated three times for five minutes at room temperature in 0.15% glycine in PBS to block aldehyde groups. Nonspecific binding was further blocked by incubation in 1% BSA in PBS for 10 minutes. Primary and secondary antibody dilutions were determined empirically and made in PBS containing 1% BSA. Sections were stained with uranyl oxalate and uranyl acetate in methyl cellulose as previously described (Crapo et al, Proc. Natl. Acad. Sci. U.S.A. 89:10405 (1992)). Control groups were as described for light microscopy above.

TABLE VI

Staining procedures for electron microscopic immunohistochemistry. All incubations were performed at room temperature.

| | Incubation | Time |
|---|---|---|
| Step 1 | PBS + 0.15% glycine | 3 × 5 minutes |
| Step 2 | 1% BSA/PBS | 5 minutes |
| Step 3 | Primary antibody in 1% BSA/PBS | 45 minutes |
| Step 4 | Protein -A gold | 30 minutes |
| Step 5 | Uranyl oxalate | 5 minutes |
| Step 6 | Uranyl acetate/methyl cellulose | 10 minutes |

Results

Characteristic of EC-SOD antibody: The antibody to rh-EC-SOD was characterized by Western blot analysis of rh-EC-SOD and a human lung homogenate. FIG. 13 shows that the antibody reacted with both the EC-SOD type C (top band) and the type A (bottom band) subunits (Sandström et al, Biochem. J. 267:18205 (1992) in a human lung homogenate. The type A subunit does not exist in the interstium of tissues in vivo (Sandström et al, Biochem. J. 290:623 (1993)). The antibody reacted with three bands in the lane containing purified type C rh-EC-SOD. The two lowest molecular weight species in FIG. 13 are due to partial insufficient glycosylation of the rh-ECSOD in the heavily overproducing CHO-cells.

Figure 14A:
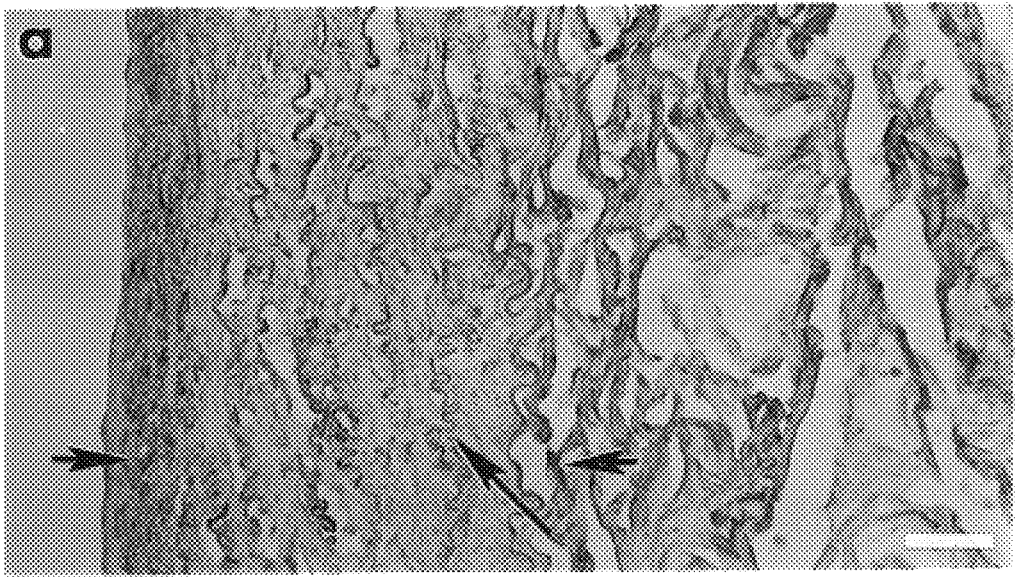
FIGS. 14A–14C show the light microscopic immunohistochemical localization of EC-SOD in human lung. Tissues were labeled using the antibody to recombinant human EC-SOD (5.4 mg/ml; anti-EC-SOD) or the same antibody in which the anti-EC-SOD IgG was absorbed out using purified recombinant EC-SOD attached to CNBr-sepharose (EC-SOD absorbed). Antibody was detected using a biotin/streptavidin-hoseradish peroxidase labeling technique. A, Large elastic pulmonary artery labeled with anti-EC-SOD. Note labeling around smooth muscle cells beneath the endothelium and beneath the elastic layer of the vessel (short arrow), and the lack of labeling for EC-SOC on the surface of endothelial cells (open arrow) and on elastin (long arrow). B, Muscular pulmonary artery labeled with anti-EC-SOD. Note high amount of labeling in the connective tissue matrix surrounding the vessel and lymphatics (long arrow), in the matrix surrounding smooth muscle cells (short arrow), and the lack of labeling on the surface of endothelial cells (open arrow). C, Muscular pulmonary artery labeled with EC-SOD absorbed antisera. The absorption of anti-EC-SOD IgG abolished all labeling in the muscular vessel. (Bars=50 µm).
Figure 14B:
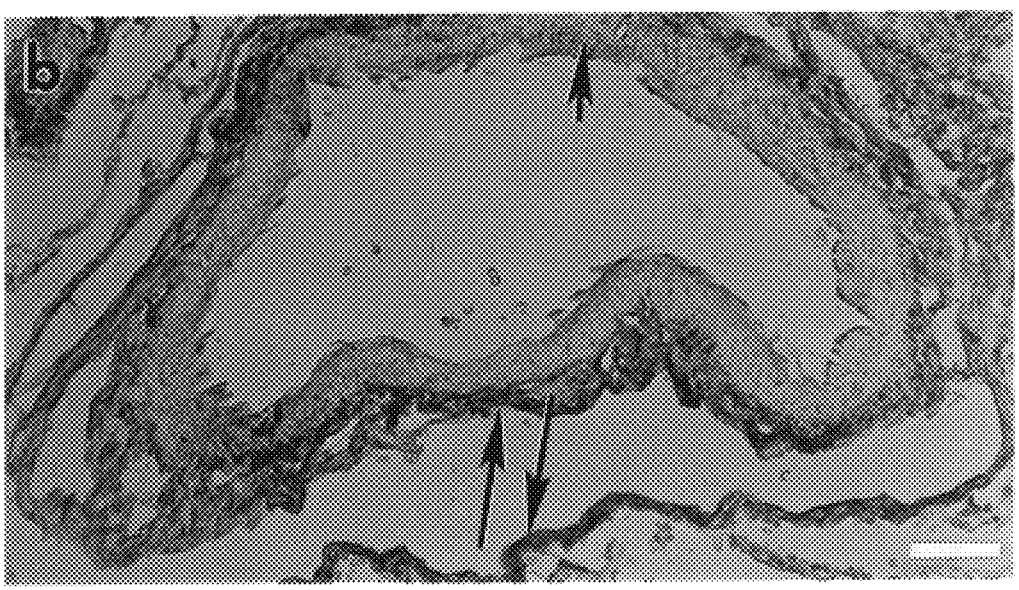
Figure 15A:
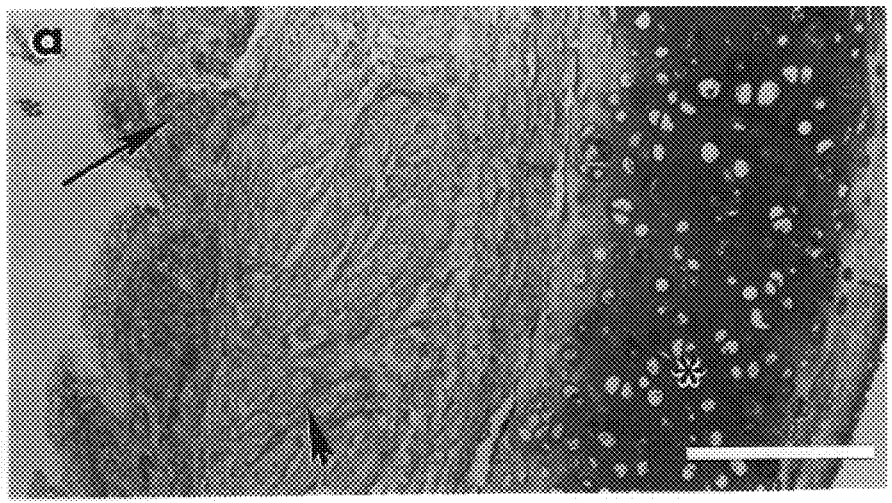
FIGS. 15A–15C show the immunohistochemical localization of EC-SOD in human lung. Tissues were labeled using the antibody to recombinant human EC-SOD (5.4 mg/ml; anti-EC-SOD). Antibody was detected using a biotin/streptavidin-horseradish peroxidase labeling technique. A, Large cartilaginous airway labeled with anti-EC-SOD. Note the intense labeling for EC-SOD in the matrix around smooth muscle cells (short arrow), between the epithelial cells (long arrow), anc the lack of labeling on the surface of the epithelial cells (open arrows), and in the matrix of cartilage (asterisk). B, Noncartilaginous airway labeled with anti-EC-SOD. Note the intense labeling for EC-SOD throughout the entire matrix beneath the epithelium (short arrow), and the lack of labeling on the surface of the epithelium (open arrow). C, Lung parenchyma labeled with anti-EC-SOD. EC-SOD labeling is primarily at alveolar septal tips (short arrow), and in the matrix surrounding small vessels (long arrow). No labeling for EC-SOD was seen on the surface of alveolar epithelial cells (cpen arrow). (Bars=50 µm).
Figure 15B:
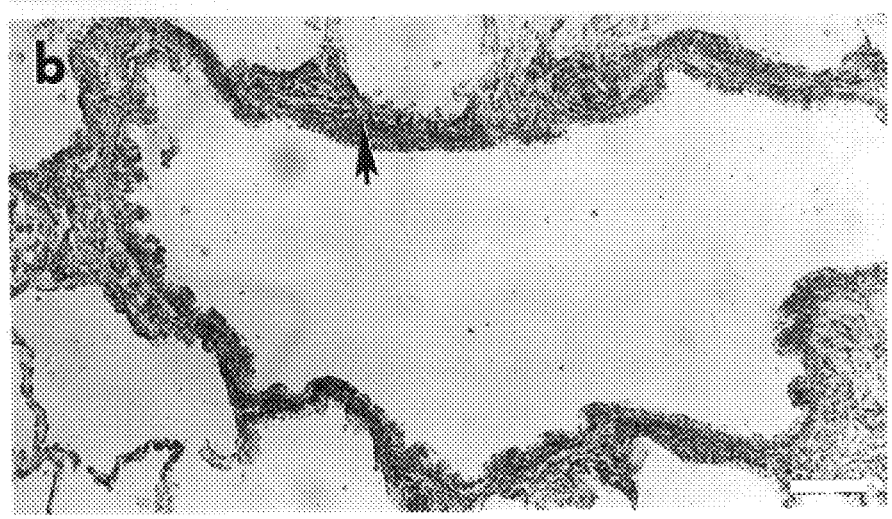
Figure 15C:
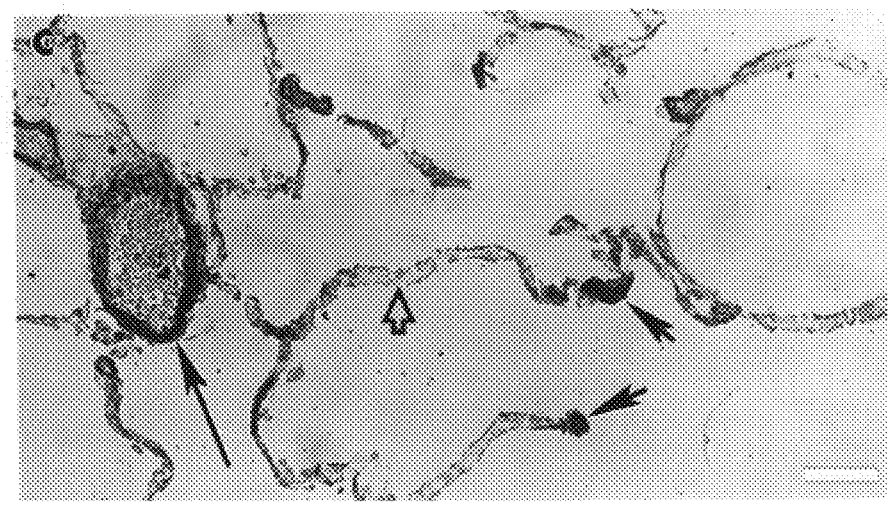

Light microscopic immunohistochemistry: Using an antibody to rh-EC-SOD, this protein was immunolocalized in human lungs. Light microscopic immunohistochemistry revealed with EC-SOD is mainly associated with the connective tissue matrix around vessels and airways in the lung (FIG. 14a and b, FIG. 15a, b, and c). EC-SOD was found in close proximity to vascular and airway smooth muscle (FIG. 14a and b, and FIG. 15a). EC-SOD was also seen in connective tissue of alveolar septal tips (FIG. 15c) suggesting an affinity of EC-SOD for connective tissue matrix. No labeling was seen in association with vascular endothelial cells in large elastic arteries, medium-sized vessels, or capillaries, (FIG. 14a and b). EC-SOD was notably absent from the epithelial cell surfaces of airways (FIG. 15a and b) and was also not present in cartilage (FIG. 15a).

Figure 14C:
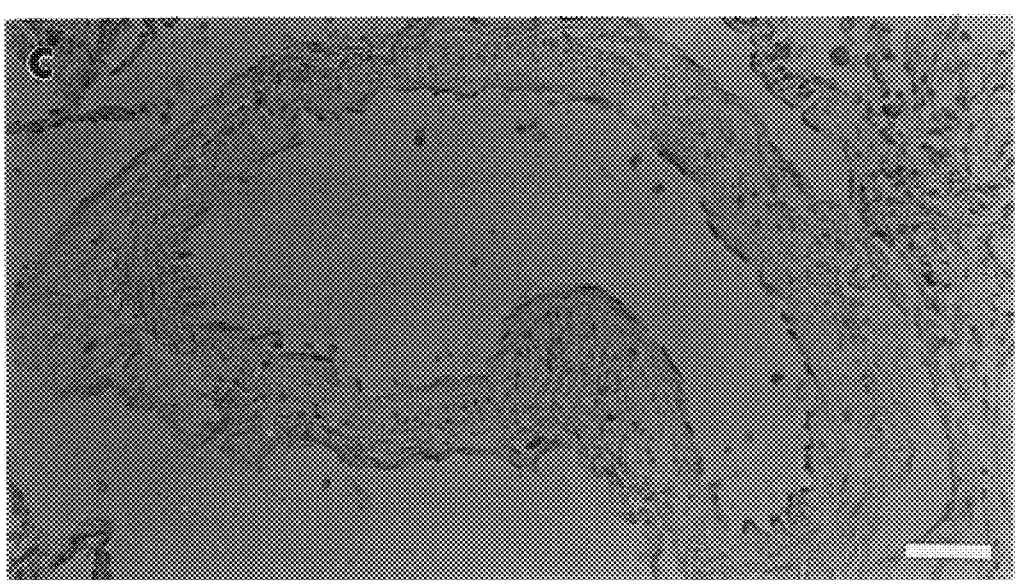

The antibody to EC-SOD was an IgG polyclonal rabbit antibody which was affinity purified using rh-EC-SOD. To test the specificity of the labeling for EC-SOD, IgG specific for EC-SOD was absorbed out of the antisera using pure rh-EC-SOD bound to cyanogen bromide sepharose. Nonimmune rabbit IgG was then added to this absorbed antibody in a sufficient amount to replace the absorbed IgG. Labeling lung tissues with this preabsorbed antibody preparation resulted in the absence of labeling in all areas of the lung including the pulmonary vasculature (FIG. 14c). Labeling lung tissue with nonimmune IgG alone also resulted in the absence of labeling in all areas of the lung. The controls indicate that the labeling observed with the primary antibody is specific for EC-SOD in the lung.

Figure 16A:
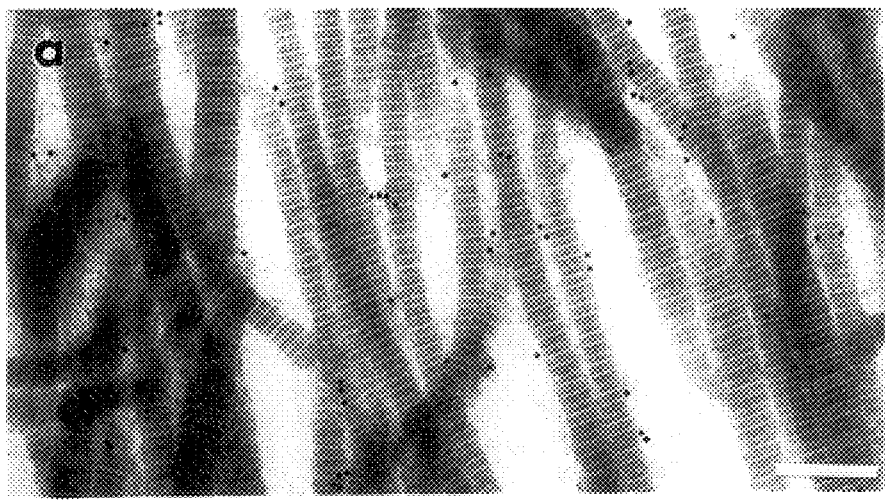
FIGS. 16A–16C show the electron microscopic immunolocalization of EC-SOD in vascular connective tissue. Tissues were labeled using the antibody to recombinant human EC-SOD (40 μg/ml; anti-EC-SOD) or the same antibody after the anti-EC-SOD IgG was absorbed out using purified recombinant EC-SOD attached to CNBr-sepharose (EC-SOD absorbed). Antibody was detected using 10 nm protein-A gold. A, Vascular collagen labeled with anti-EC-SOD, B, Vascular elastin labeled with anti-EC-SOD. C, Vascular collagen labeled with EC-SOD absorbed antisera. Note the intense labeling of EC-SOD in association with type I collagen and the lack of labeling in association with elastin (E). In addition, absorption of anti-EC-SOD antibody abolished all labeling for EC-SOD in association with type I collagen. (Bars=200 nm).
Figure 16B:
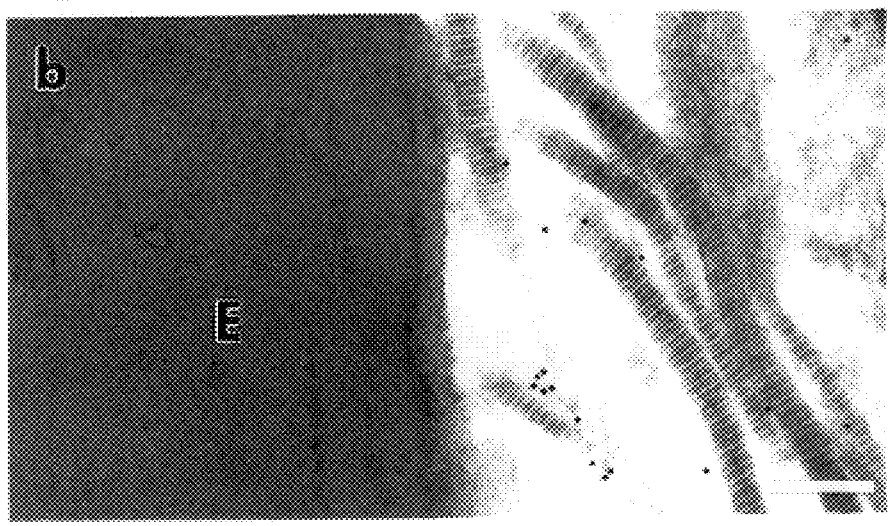
Figure 17:
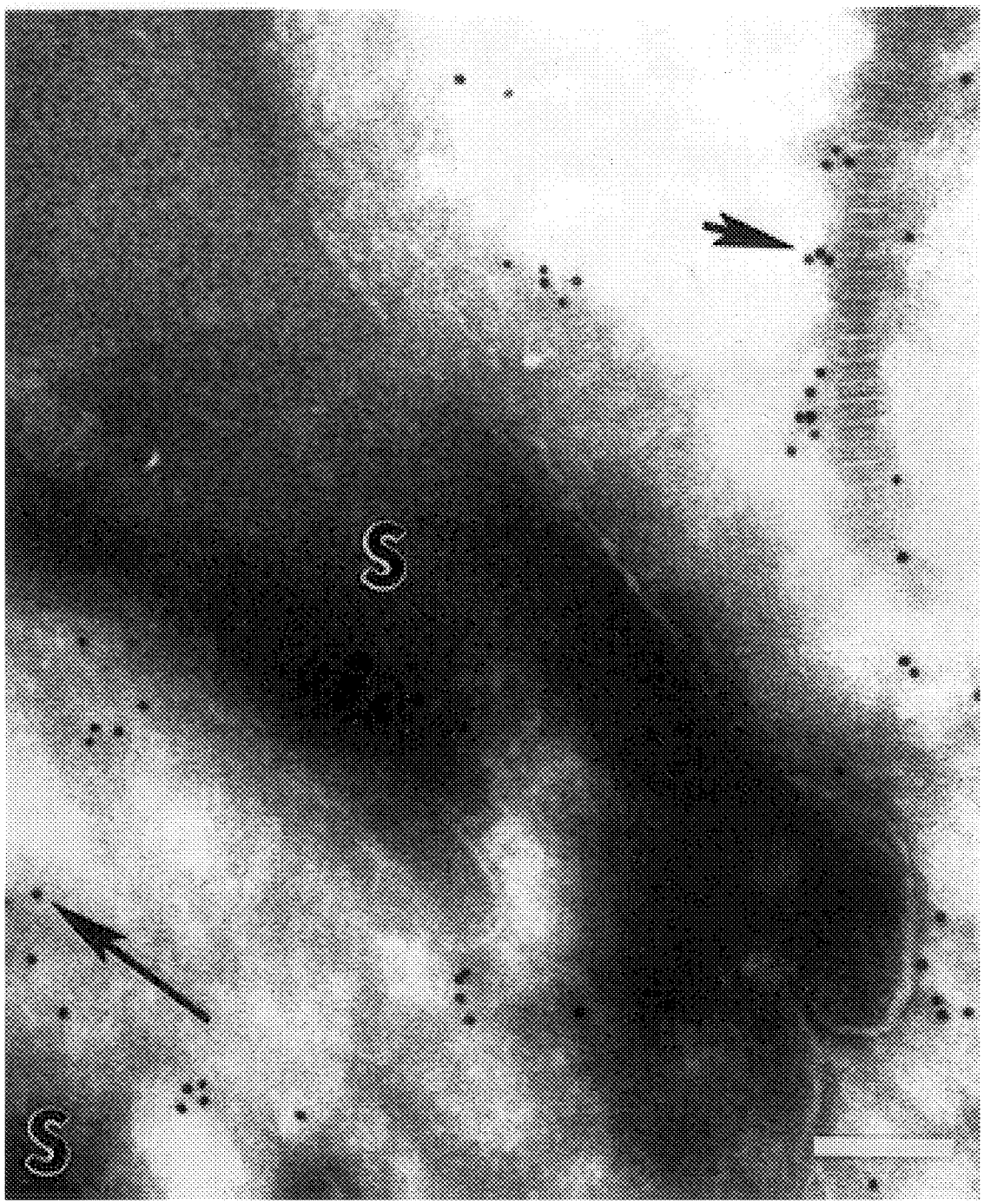
FIG. 17 shows the electron microscopic immunolocalization of EC-SOD around vascular smooth muscle. Tissues were labeled using the antibody to recombinant human EC-SOD (40 μg/ml). Antibody was detected using 10 nm protein-A gold. There is a high degree of labeling in the connective tissue matrix around the vascular smooth muscle cell (S) in association with type I collagen (short arrow), and other unidentified matrix elements (long arrow). (Bars=200 nm).
Figure 18A:
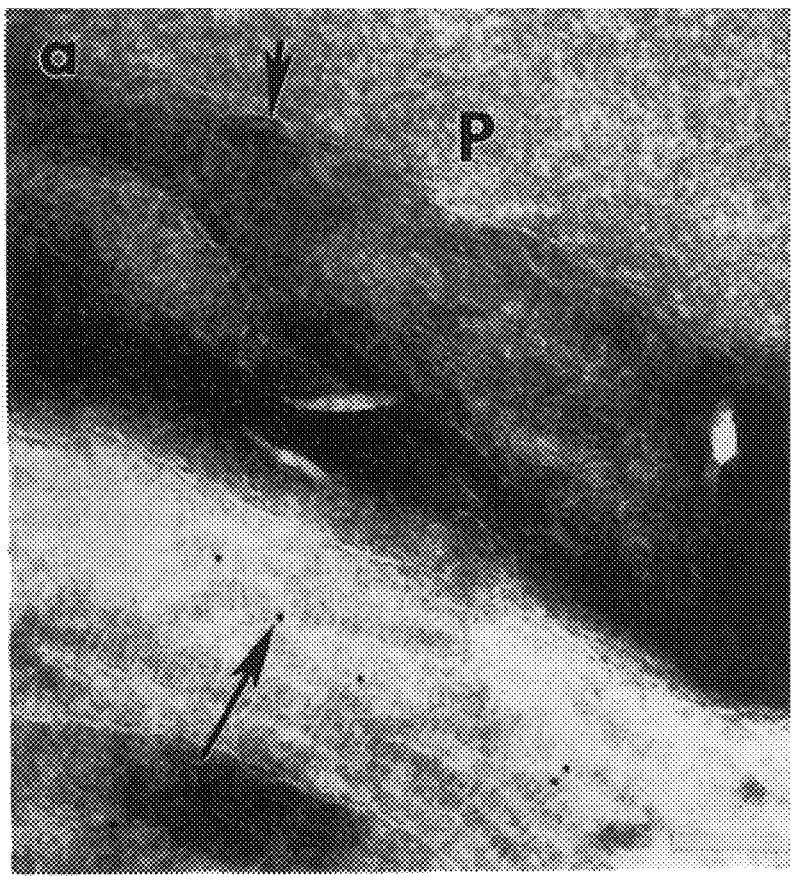
FIGS. 18A–18B show the electron miscropic immunolocalization of EC-SOD on the surface of pulmonary endothelial cells. Tissues were labeled using the antibody to recombinant human EC-SOD (40 μg/ml). Antibody was detected using 10 nm protein-A gold. A, Endothelial cell from a small muscular pulmonary artery, B, Endothelial cell from a pulmonary capillary. No labeling for EC-SOD was on the surface of the endothelial cells (short arrows). EC-SOD is Eeen in the plasma (P) and is associated with extracellular matrix proteins beneath the endothelium (long arrows). (Bars=200 nm).
Figure 18B:
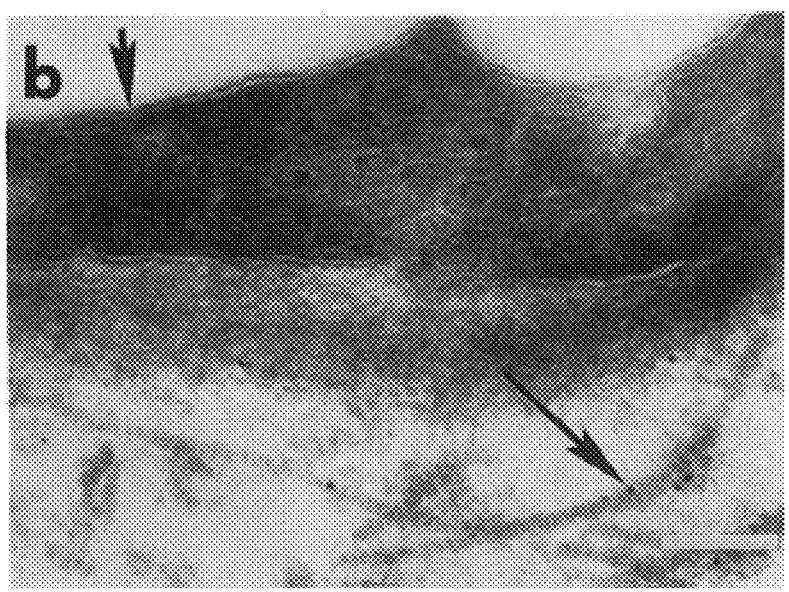
Figure 19:
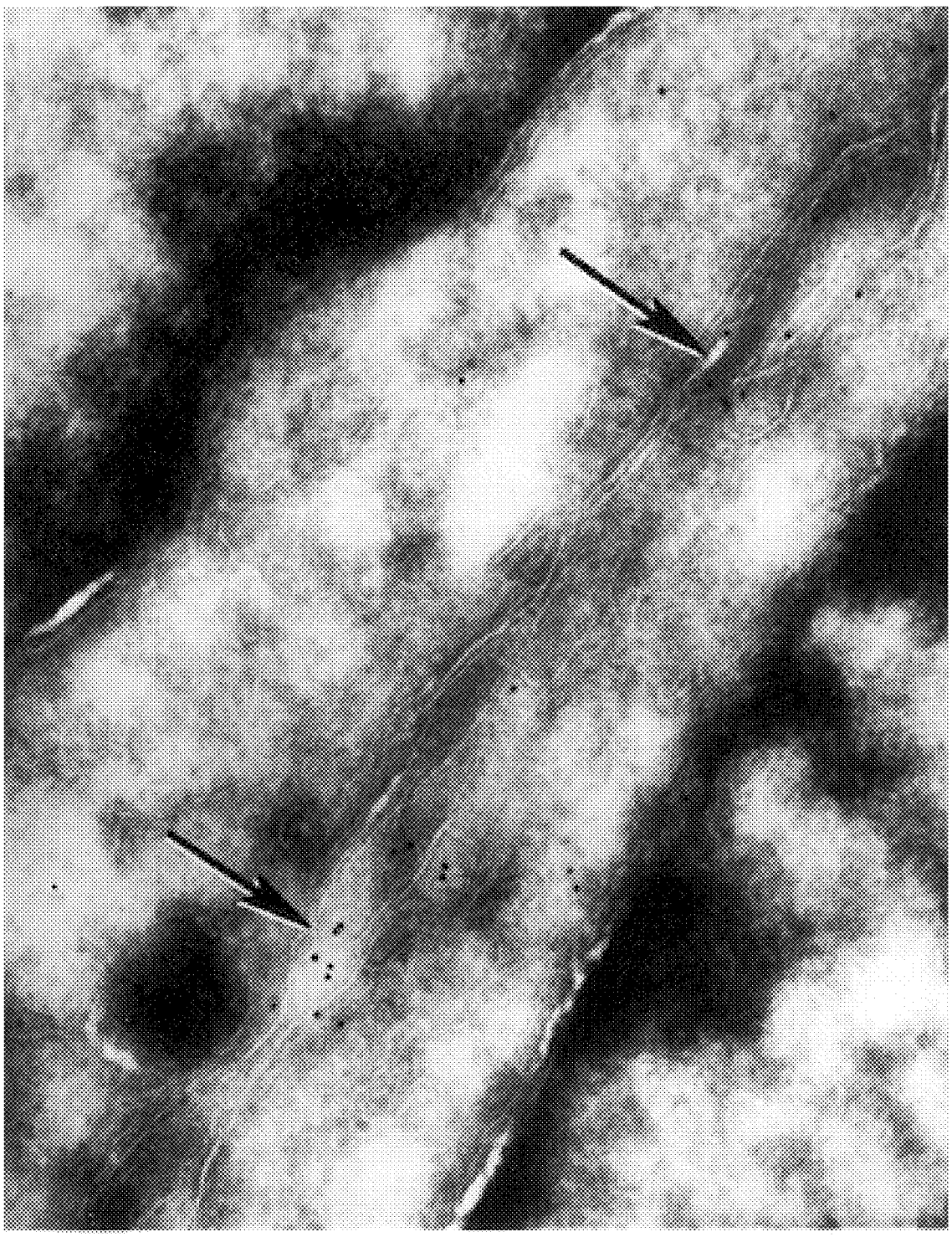
FIG. 19 shows the electron microscopic immunolocalization of EC-SOD around bronchial epithelial cells. Tissues were labeled using the antibody to recombinant human EC-SOD (40 μg/ml). Antibody was detected using 10 nm protein-A gold. EC-SOD was found in the junction between the epithelial cells (arrow) and was also seen to some extent inside the cells. (Bars=200 nm).

Electron microscopic immunocytochemistry: A summary of the labeling for EC-SOD in the lung found using electron microscopic immunocytochemistry is summarized in Table VII. EC-SOD was mainly associated with extracellular matrix proteins in all regions of the lung. In particular, a high degree of labeling was seen in areas rich in type I collagen (FIG. 16) and in association with other unidentified proteoglycans in extracellular matrix (FIG. 17). Notably, no labeling for EC-SOD was seen in elastin-rich areas (FIGS. 16). A high degree of labeling was observed near the surface of smooth muscle cells and in the connective tissue matrix surrounding smooth muscle cells in vessels (FIG. 17) and airways. Labeling was notably absent from the surface of endothelial cells on small, medium and large vessels (FIGS. 18a and b). The lack of endothelial cell labeling found with the light microscopic immunohistochemistry support the electron microscopic findings. Labeling of EC-SOD was also seen in plasma within the lumen of blood vessels (FIG. 18a). The localization of EC-SOD in plasma is expected as this protein was first discovered in plasma (Marklund, Acta Physiol. Scand., 5492:19 (1980)). Labeling for EC-SOD was observed in the intercellular junctions between bronchial epithelial cells (FIG. 19), but was absent from the apical surface of these cells. Finally, EC-SOD labeling was absent from the surface of type I and type II cells. A moderate, but consistent amount of intracellular EC-SOD was found in type II epithelial cells and in bronchial epithelial cells (FIG. 19).

TABLE VII

Distribution of EC-SOD in human lung. (+) indicates presence of labeling for EC-SOD and (−) indicates no labeling for EC-SOD. (±) represents areas where low low amounts of labeling for EC-SOD were inconsistently observed.

| Location | EC-SOD |
| --- | --- |
| Cell Surfaces | |
| Endothelial | − |
| Type I cell | − |
| Type II cell | − |

TABLE VII-continued

Distribution of EC-SOD in human lung. (+) indicates presence of labeling for EC-SOD and (−) indicates no labeling for EC-SOD. (±) represents areas where low low amounts of labeling for EC-SOD were inconsistently observed.

| Location | EC-SOD |
| --- | --- |
| Smooth muscle cell | + |
| Fibroblast | ± |
| Extracellular Matrix | |
| Type I collagen | + |
| Elastin | − |
| Cartilage | − |
| Unidentified matrix elements | + |
| Intracellular | |
| Endothelial cell | ± |
| Type I cell | − |
| Type II cell | + |
| Bronchial epithelial cell | + |
| Smooth muscle cell | − |
| Fibroblast | ± |
| Blood | |
| Plasma | + |
| Red Blood Cell | − |

Figure 16C:
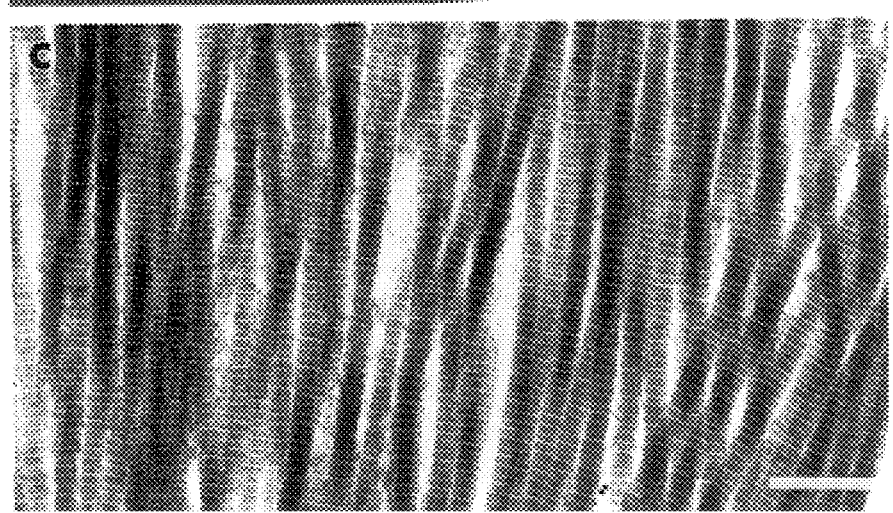

Controls done by absorbing EC-SOD specific antibody out of the primary antibody and replacing this absorbed antibody with nonimmune rabbit IgG resulted in the absence of labeling in all areas of the lung including areas rich in type I collagen as seen in FIG. 16c. In addition, use of nonimmune rabbit IgG instead of the primary antisera also resulted in the absence of labeling in all areas of the lung. The lack of labeling with these controls indicates that the labeling observed with the primary antisera is specific for EC-SOD in the lung.

The localization of EC-SOD on the surface of smooth muscle cells and in the extracellular matrix around these cells in both blood vessels and airways indicates that EC-SOD may have an important function in this location. Superoxide is known to rapidly react with nitric oxide and inactivate its properties as a smooth muscle relaxant. Therefore, the presence of EC-SOD along the diffusion path of nitric oxide to smooth muscle cells should increase the half life of this short lived intercellular messenger in this particular region and thus increase its potency as a vasodilator. The high labeling for EC-SOD seen around vascular and airway smooth muscle cells indicates a function for EC-SOD as a mediator of nitric oxide activity in the maintenance of low pulmonary vascular pressures and airway resistence.

In addition to the labeling of EC-SOD in association with smooth muscle cells, EC-SOD also appears to strongly colocalize with type I collagen. Collagen has previously been demonstrated to be susceptible to attack by reactive oxygen species such as the superoxide anion. In addition, the superoxide anion may be capable of activating latent collagenases from polymorphonuclear leukocytes (PMN) which can lead to further collagen degradation. Because collagen fragments have been shown to chemoattract and activate PMN's, any increased produced of superoxide that results in collagen degradation may accelerate inflammatory reactions and tissue destruction through PMN recruitment and activation. Consequently, the association of EC-SOD with collagen may be important in preventing superoxide mediated degradation of collagen and therefore, represent a means of controlling inflammatory responses.

EXAMPLE V

Human EC-SOD Gene

Protocols

Materials and radiochemicals:

[α-$^{35}$S]dATP (~1400 Ci/mmol), [γ-$^{32}$P]ATP (3000 Ci/mmol), and [α-$^{35}$P]CTP (800 Ci/mmol), were purchased from New England Nuclear. Human genomic DNA, T$_7$, T$_3$, and SP6 RNA polymerase, RNasin, and the pGEM3Zf(+) plasmid were obtained from Promega Biotec. Sequenase sequencing kit (V 2.0) was from United States Biochemicals Corporation. Human poly A+ RNA was acquired from Clontech. SeaPlaque GTG agarose was from FMC BioProducts. Restriction enzymes were from New England Biolabs. All other reagents used were molecular biology grade. Oligonucleotides were synthesized using an Applied Biosystems 380B or 392 by the Duke University, Department of Botany DNA synthesis facility. Charged nylon membranes (GeneScreen Plus) were from DuPont.

Human Northern blot or analysis:

Two μg poly A+ RNA were purified from eight different human tissues. These mRNAs were electrophoresed on a denaturing formaldehyde 1.2% agarose gel and transferred to a charge-modified nylon membrane followed by UV irradiation fixation. The membrane was prehybridized in 50% formamide, 0.25 M NaPO$_4$ (pH 7.2), 0.25 M NaCl, 1 mM EDTA, 7% SDS, and 5% polyethylene glycol (molecular weight 8000). The blot was hybridized in the same buffer overnight at 60° C. with 1×10$^6$ cpm/ml of [$^{32}$p]-labeled human EC-SOD RNA generated by transcription of the full-length cDNA using T$_3$ RNA polymerase in the presence of [α-$^{32}$P]CTP. The blot was washed in 0.25 M NaPO$_4$ (pH 7.2), 1% SDS, and 1 mM EDTA at 75° C. followed by a second wash using 0.04 M NaPO$_4$ (pH 7.2), 1% SDS, and 1 mM EDTA at 75° C. for 30 minutes. This was followed by exposure to XAR-5 film using a Lightening Plus intensifier screen at −70° C. The autoradiogram was scanned using an LKB Ultrascan XL laser densitomer, and the peaks were quantitated by integration using the internal digital integrator of the densitometer or by cutting out the peak from a printer tracing and weighing.

5' Rapid amplifciation of cDNA ends:

0.5 μg of poly A+ mRNA from human heart was reversed transcribed using 2 pmoles of EC7, a 5' EC-SOD gene specific anti-sense oligonucleotide (5'-ATGACCTCCTGCCAGATCTCC-3'), following a protocol by GIBCO BRL (5' RACE System). The RNA template was degraded by the addition of RNase H at 55° C. for 10 minutes. The resulting cDNA was isolated using a Glass-MAX DNA (GIBCO BRL) isolation spin cartridge. The purified cDNA was dC-tailed using terminal deoxynucleotidyl transferase (TdT, 0.5 units/ul). 200 μM dCTP, 10 mM Tris-HCl (pH 8.4), 25 mM KCl, 1.25 mM MgCl$_2$ and 50 μg/ml bovine serum albumin for 10 minutes at 37° C. The TdT was heat inactivated for 10 minutes at 70° C.

Products of this reaction were next PCR amplified using the "anchor" primer (GIBCO BRL), which hybridizes to the homopolymeric tail, and EC4 (a nested internal 5' EC-SOD gene specific anti-sense oligonucleotide, 5'-AGGCAGGAACACAGTAGC-3'). Alternatively, the dC-tailed products were PCR amplified using EC7 and HEC1 (a sense-strand EC-SOD gene specific primer, 5'-TGGGTGCAGCTCTCTTTTCAGG-3'). The final composition of the reaction included 20 mM Tris-HCl (pH 8.4), 50 mM KCl, 2.5 mM MgCl$_2$, 100 μg/ml bovine serum albumin, 400 nM Anchor primer, 200 nM gene-specific primer, and 200 μM each of dATP, dCTP, dGTP, dTTP. After incubating the PCR reaction for 5 minutes at 94° C., amplitaq (Perkin Elmer Cetus) was added at a final concentration of 0.04 units/μl. PCR cycling was performed on a Perkin Elmer 9600 for 35 cycles with melting at 94° C. for 45 seconds and annealing at 53° C. for 15 seconds and extension at 72° C. for 90 seconds. The full-length EC-SOD cDNA (6 ng) was used as a positive control in the PCR reaction. The PCR products were electrophoresed in a 2% SeaPlaque GTG agarose gel, transferred to charged nylon membranes by the method of Southern (Southern, J. Mol. Biol. 98:503 (1975)) using the alkaline transfer protocol (Reed et al, Nuc. Acids Res. 13:7207 (1985)). The DNA was fixed to the membrane by baking at 80° C. in a vacuum oven for 2 hours. The subsequent blot was hybridized to [$^{32}$p] end-labeled HEC2 (an internal, nested EC-SOD specific primer, 5'-TCCAGCTCCTCCAAGAGAGC-3') overnight at 37° C. The blot was washed at increasing stringencies until background hybridization was removed. This was followed by exposure to XAR-5 film using a Lightening Plus intensifier screen at −70° C.

Human genomic Southern blot analysis:

Ten μg human genomic DNA were digested BamH I, EcoR I, Kpn I, and Pst I restriction endonuclease enzymes until completion. The DNA was then electrophoresed on 1% agarose gel and transferred to a charged nylon membrane by the Southern technique (Southern, J. Mol. Biol. 98:503 (1975)), after alkaline denaturation (Reed et al, Nuc. Acids Res. 13:7207 (1985)). The DNA was fixed to the membrane by heating to 80° C. in a vacuum oven for 2 hours. [$^{32}$P]CTP-labeled human EC-SOD antisense strand cRNA was synthesized using the EC-SOD cDNA which had been linearized with Stu I. The blot was hybridized (500×10$^3$ cpm/ml) in 50% formamide, 0.25 M NaPO$_4$ (pH 7.2), 0.25 M NaCl, 1 mM EDTA, 7% SDS, and 5% polyethylene glycol (molecular weight 8000), at 50° C. Following overnight hybridization, they were washed in 0.25 M NaPO$_4$ (pH 7.2), 2% SDS, and 1 mM EDTA followed by 0.04 M NaPO$_4$ (pH 7.2), 1% SDS, and 1 mM EDTA at increasing stringencies until background hybridization was minimized. The blot was exposed to XAR-5 film using a Lightening Plus intensifier screen at −70° C.

Isolation of the human gene for EC-SOD:

A human adult female leukocyte genomic library constructed in the EMBL-3 vector was obtained from Clontech. Approximately 1×10$^6$ pfu were screened at a density of ~50,000 pfu/plate using [$^{32}$P]CTP-labeled human EC-SOD cRNA (1×10$^6$ dpm/ml). The primary through tertiary screens identified approximately 7 unique putative positive plaques. Individual plaques were isolated and lambda DNA purified using LambdaSorb phage adsorbent (Promega Biotec). The size of the insert DNA from each clone was assessed by Sal I restriction endonuclease digestion followed by electrophoresis in 0.7% agarose. Selected clones underwent extensive restriction endonuclease mapping. Based on the restriction mapping results and asymmetric hybridization using 5' and 3' annealing EC-SOD oligonucleotides, Clone #7 was selected for all subsequent DNA sequence analysis. Clone #7 contains an approximate 18–20 kb fragment.

DNA sequencing of the human EC-SOD gene:

The overall strategy used for sequencing clone #7 is illustrated in FIG. 20. Various size restriction endonuclease DNA fragments from clone #7 were subcloned into the pGEM3Zf(+) vector DNA. The dideoxy sequencing method using double-stranded DNA (Ausubel et al, Current Protocols in Molecular Biology, Green Publishing Assoc. and Wiley Interscience, New York (1992)) as template and Sequenase enzyme (United States Biochemicals) were employed (Sanger et al, Proc. Natl. Acad. Sci. U.S.A. 74:5463 (1977)). Both the Universal and −40 M13 sequencing primers were used to initiate DNA sequencing for each subcloned fragment. Oligonucleotides derived from this initial sequencing data were synthesized approximately every 250 base pairs until the complete nucleotide sequence was obtained. Sequencing data were obtained from both strands as shown in FIG. 20B except at the 3' portion of the gene where DNA sequence was obtained on one strand only.

Computer-assisted sequence analysis and transcriptional database search:

The IntelliGenetics Geneworks program (Version 2.2) was used for organizing the DNA sequence data. Homology searching was performed at the NCBI using the BLAST (Altschul et al, J. Mol. Biol. 215:403 (1990)) network service and the non-redundant nucleotide sequence database (GenBank(77.0)+EMBL(35.0)+EMBLUpdate+GBUdate). Transcriptional factor database searching was performed using both the SIGNAL SCAN 3.0 algorithm (Prestridge et al, CABIOS 9:113 (1993)) as well as the FINDPATTERNS program of the GCG Package (V 7.2) using Release 6.3 of the Transcription Factor Database (Gosh, Nuc. Acids Res. 18:1749 (1990)). For a prediction of the site of signal peptide cleavage, the programs, SIGSEQ1 (Folz et al, J. Biol. Chem. 261:14752 (1986)) and SIGSEQ2 were employed (Folz et al, Biochem. Biophys. Res. Commun. 146:870 (1987)).

Results

Figure 21A:
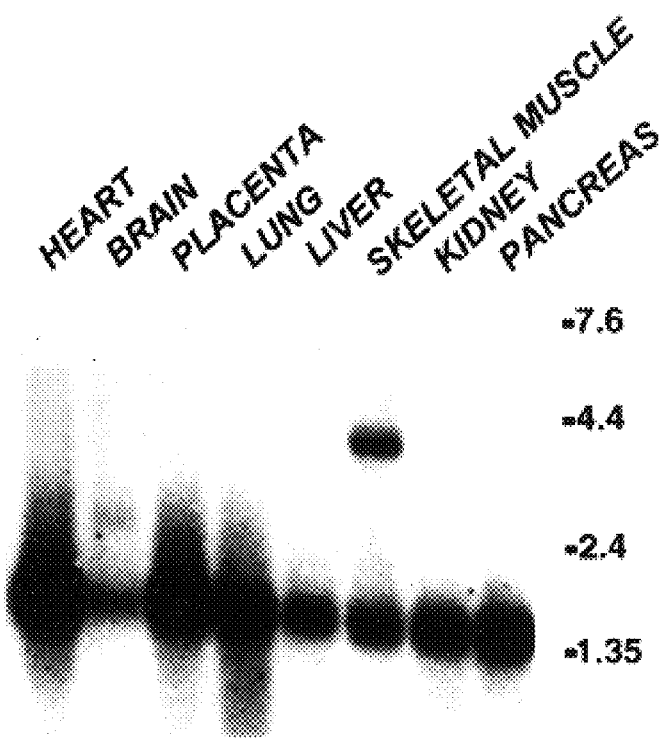
FIGS. 21A–21B show human multiple tissue Northern blots of EC-SOD.
Figure 21B:
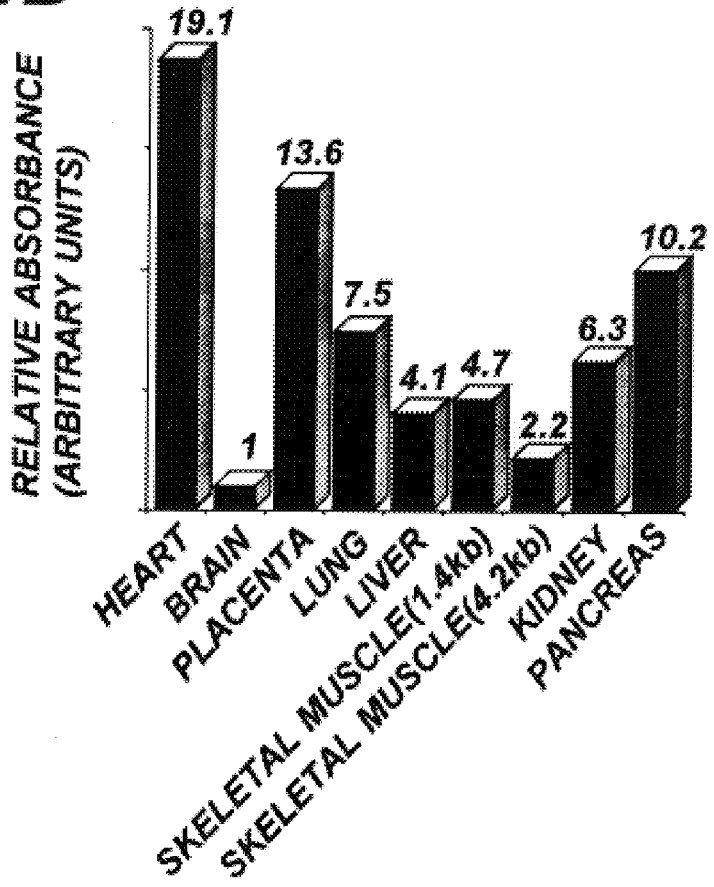

Tissue specific expression of human EC-SOD:

To investigate the expression of human EC-SOD, poly A(+) MRNA from eight different human tissues was fractionated on a denaturing agarose gel and transferred to a charged nylon membrane. Because a previous paper reported long exposures times in order to identify EC-SOD specific bands during genomic Southern analysis (Hendrickson et al, Genomics 8:736 (1990)), a radiolabeled antisense cRNA probe derived from full-length human EC-SOD cDNA was used (Oury et al, Eroc. Nat. Acad. Sci. U.S.A. 89:9715 (1992)). A discrete band of approximately 1.4 kb can be seen in all eight human tissues analyzed (FIG. 21A). In addition, skeletal muscle contains an approximate 4.2 kb message, not detected in the other tissues. By densitometric scanning of the 4.2 and 1.4 kb bands, it can be calculated that larger message to make up about 32% of the total skeletal muscle EC-SOD message. In brain, a very faint band of 2.2 kb can be seen. This band was too weak for quantitation by laser densitometer. Quantitation of these bands was performed by laser densitometry and integration of peaks of autoradiograms obtained in the linear range of exposure (FIG. 21B). After normalizing to the brain, the heart showed the most expression with 10.1 times brain. This was followed by the placenta, pancreas, and lung which gave 13.6, 10.2, and 7.5, respectively. Expression in skeletal muscle was 4.7 for the 1.4 kb band or 6.9 for both 1.4 kb and 4.2 kb message, while the kidney and liver gave 6.3 and 4.1 time expression over brain. These patterns of expression have been reproduced based on probing an additional independent multiple tissue Northern blot. The bands are specific based on the relatively high stringencies of washing and from data using a sense strand EC-SOD cRNA as a probe which showed no hybridization under the conditions given.

Figure 22A:
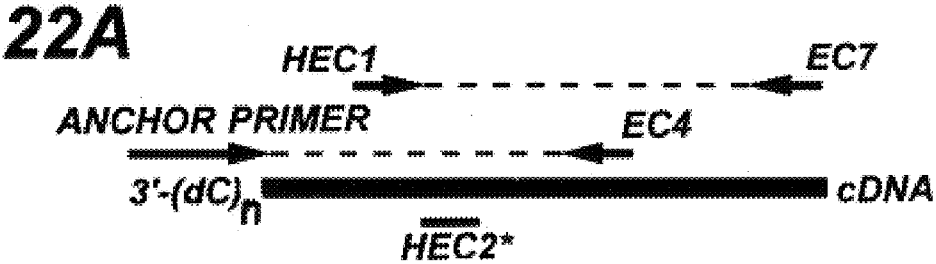
FIGS. 22A–22B show analysis of the transcription initiation site. The 5' rapid amplification of cDNA ends (5' PACE) technique was used to identify the site of transcription initiation for the human EC-SOD gene.
Figure 22B:
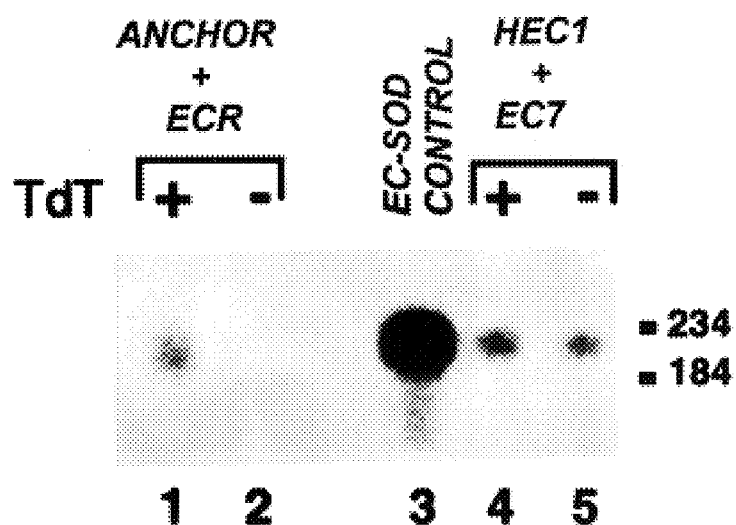

Mapping the site transcription initiation:

Initially, mapping of the site of transcription initiation was attempted using the primer extension method. Using several different end-labeled 5' oligonucleotides and both human lung and human heart poly A+ mRNA as well as total RNA isolated from human foreskin fibroblasts, a positive signal was not obtained even after long exposure times. This did not seem to be due to technique since it was not possible to get positive signals using RNA generated by in vitro transcription of the EC-SOD cDNA. Whether lack of success using this technique was due to very low abundance of MRNA encoding EC-SOD or some other problem(s) is unclear. Working under the assumption of low abundance MRNA, the technique of rapid amplification of cDNA ends in order to PCR amplify this signal was attempted. The EC-SOD gene specific primer EC7 was used for hybridization and reverse transcription of human heart poly A+ mRNA as shown in FIG. 22. Half of this reaction was 3' dC tailed using terminal deoxynuclectidyl transferase and the remaining half was not. These templates were then subjected to PCR amplification using the gene specific primers HECl+ EC7 as well as the anchor primer+EC4. The products of these reactions were fractioned by agarose electrophoresis, transfered to nylon membranes, and probed with the interal nested gene specific primer HEC2. An autoradiogram of this experiment is shown in FIG. 22A. Using EC-SOD cDNA as a control template and HEC1+EC7, a band of 217 bp is expected (lane 3 of FIG. 22A). Since the primers HEC1 and EC7 are expected to amplify independant of dC tailing, bands of equal intensity in lanes 4 and 5, which are also of the same size as the EC-SOD control, are seen. Using the anchor primer (which hybridizes to the dC tail) and EC4, only one band of ~190 bp was seen (lane 1). Since the template was not poly C tailed, lane 2 shows no signal as expected. By subtracting 48 bp (the size of the anchor primer), the size of the reverse transcribed DNA would correspond to ~136 bp 5' of the EC4 primer. This analysis would predict that there is approximately 6 base pairs of additional 5' sequence on the cDNA clone and that transcription initiation starts about 6 bp upstream of the first intron (indicated by a dashed box). Although eukaryotic transcription initiation usually begins at an adenosine residue, it is expected that it will begin at a G (Breathnach et al, Ann. Rev. Biochem. 50:349 (1981)).

Figure 23:
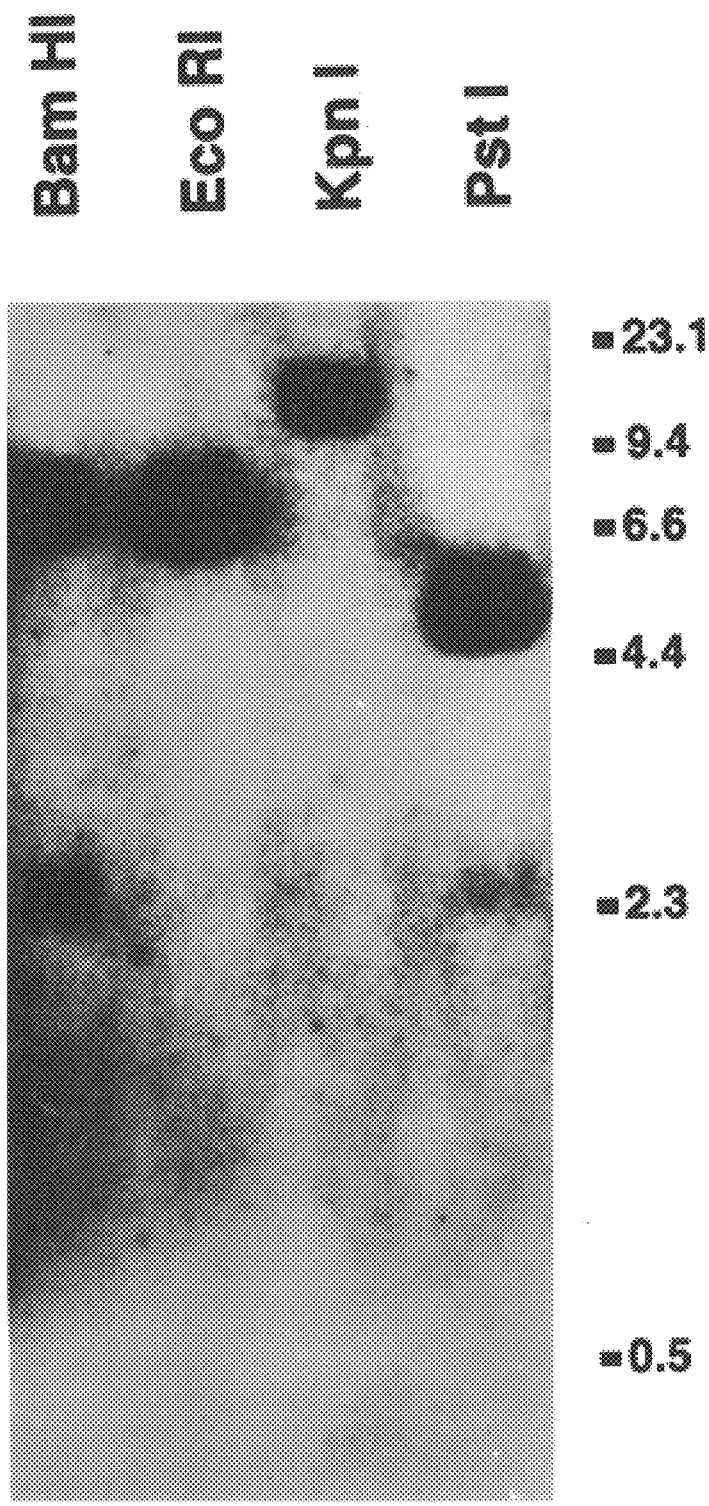
FIG. 23 shows genomic Southern blot analysis of the human EC-SOD gene. Ten micrograms of human genomic DNA were completely digested with each of the restriction enzymes shown, electrophoresed on a 1% agarose gel and transferred to charged nylon membranes. The blots were proved with a [$^{32}$p]-labeled EC-SOD partial length CRNA which corresponds to the first approximate 1050 nucleotides and autoradiographed. The specific restriction endonuclease is shown at the top of each lane. DNA molecular size markers (in kilobases) are shown on the right.

Genomic Southern blot analysis:

To begin to charcterize the human EC-SOD gene, 10 μg of the total human genomic DNA was restriction digested and the reaction products electrophoresed on an agarose gel followed by transfer to a nylon membrane. The blot was probed with a [$^{32}$p]-labeled partial EC-SOD cRNA. An autoradiogram of this blot is shown in FIG. 23. As can be seen for each lane, there are unique bands associated with each restriction digest. No shadow bands which might suggest pseudogenes were seen. When a full-length cRNA probe was used for Kpn I digested DNA, an additional band of ~4000 bp was seen which corresponds to the 3' end of the gene. In addition, the Kpn I lane shows a 0.5 kb band which was better seen on other blots. This banding pattern was similar to a restriction map of the human EC-SOD clone #7 (see FIG. 20A)

Isolation and characterization of the human EC-SOD by DNA sequencing:

Multiple independent positive clones were identified from a human adult leukocyte genomic library constructed in EMBL-3. These clones underwent extensive restriction endonuclease mapping and were probed with EC-SOD specific 5' and 3' oligonucleotides in order to determine the relative orientation of the inserts. Based on these results, clone #7 was picked for further analysis. Clone #7 is about 18 to 20 kb and contains at least 5000 bp of 5' flanking DNA and at least 4000 bp of 3' flanking DNA. Restriction mapping of clone #7 is shown in FIG. 20A. This map is similar to the results obtained with genomic Southern blot analysis data indicating that clone #7 contains the EC-SOD gene. The strategy for sublconing and sequencing clone #7 is shown in FIG. 20B. Various size continguous and overlapping restriction fragments were subcloned into the plasmid vector pGEM32f(+) (FIG. 20B). The DNA inserts were sequenced on both strands using a combination of primer walking and vector specific, universal sequencing primers. The 3' half of 7K36 insert was sequenced on one strand only. Published sequence data for the human EC-SOD cDNA (Hjalmarsson et al, Proc. Natl. Acad. Sci. U.S.A. 84:6340 (1987)) as well as DNA sequence information obtained from an independant cDNA clone which contained additional 5' untranslated data (Hendrickson et al, Genomics 8:736 (1990)) were used to determine the genomic intron/exon structure. Based on a comparison of these data with the genomic sequence information, the human EC-SOD gene was determined to contain three exons and two introns (FIG. 20C). Exon 1 contains at least 5 base pairs and is probably larger (by about 6 base paris), since the exact start of transcription initiation was not determined (note below). Exon 2 contains 84 bp and is separated from exon 1 by a 572 bp intervening sequence marked as intron 1. Exon 3 is separated from exon 2 by intron 2, a 3849 bp segment. Exon 3 contains a total of 1336 bp and at 17 bp into this exon starts the beginning of the complete coding sequence for preEC-SOD (FIG. 20D). This includes an 18 amino acid signal peptide that precedes the 222 amino acid mature protein sequence. There are no introns separating the various structural domains of EC-SOD. These domains are shown schematically in FIG. 20D and include amino acids 1–95 which contain a glycosylated Asn-89 and show no sequence homology with other proteins. Resides 96–193 show strong homology with CuZn-SOD protein sequences with preservation of critical amino acids important in enzyme catalysis and structure. Amino acids 194–222 contain multiple charged resides which have been shown to be important in binding to sulfated proteoglycans. 558 bp of the 5'-flanking region containing putative regulatory elements and 3675 bp of the 3'-flanking region were also sequenced. The exonic DNA sequence data are in agreement with the published cDNA sequence (Hjalmarsson et al, Proc. Natl. Acad. Sci. U.S.A. 84:6340 (1987)). The intron-exon boundries are shown in Table VIII and conform to the eukaryotic consensus splice sequence (Senapathy et al, Methods Enzymol. 183:252 (1990)). Both introns split sequences in the 5'-nontranslated region of the EC-SOD gene.

TABLE VIII

Sequences at intron/exon splice junctions
The size of the introns and exons are shown in base pairs (bp). The uppercase letters indicate exon sequence while the lowercase letters indicate intron sequence. The splice junctions shown conform to previously published concensus sequences for splice junctions (Senapathy et al, Methods Enzymol. 183:252 (1990)).

| Donor | Intron size (bp) | Acceptor | Exon |
|---|---|---|---|
| TGCGGG gt ggac | 572 | gccc ag GCTCCA | 84 |
| GGAAAG gt gggt | 3849 | ccgc ag GTGCCC | 1336 |

FIG. 24 shows the entire sequence for the human EC-SOD gene. Exonic sequences are shown in boxed uppercase letters while intronic, 5'- and 3'-flanking sequence are shown in lowercase. Exon 3 contains the entire uninterrupted coding region for EC-SOD and the protein sequence is shown using the single letter amino acid code. The 18 amino acid signal peptide and 222 amino acid mature protein sequence are highlighted. The identification of the signal peptide cleavage site is consistent with computer algorithms which predict the site of eukaryotic signal peptide cleavage (Folz et al, Biochem. Biophys. Res. Comm. 146:870 (1987)); Von Heijne, Eur. J. Biochem. 133:17 (1983)).

Transcriptional factor database searching was used to putatively identify transcriptional regulatory elements. Although almost all eukaryotic promoters utilize a TATA box element to fix the position of transcription initiation, an obvious TATA box cannot be discerned for the EC-SOD gene. Two CAAT box elements were identified. One is in the reverse orientation and located about 20 bp upstream of the first exon, while the second can be found about 335 bp upstream. The putative signal for polyadenylation is shown and the site of poly A adenylation is indicated. Transcriptional factor database searching of the 5'-nontranslated region and first intron identified several potential regulatory elements. A cAMP responsive element (CREB) (TGACGT) which is similar to the adenovirus transcription virus (ATF) element can be found starting at 121 bp (Fink et al, Proc. Natl. Acad. Sci. U.S.A. 85:6662 (1988); Sassone-Corsi Proc. Natl. Acad. Sci. U.S.A. 85:7192 (1988)). A half site for the glucocorticoid response element (GRE) (TGTCCT) is located at 370 bp (Karin et al, Nature 308:513 (1984)). A skeletal muscle specific trans-activating factor response element (M-CAT) (CATTCCT) is found in the reverse orientation beginning at position 238 (Mar et al, Mol. Cell. Biol. 10:4271 (1990)). A xenobictic responsive element (XRE) (CACGCW) is found within the first intron at position 1085 bp (Rushmore et al, J. Biol. Chem. 265:14648 (1990)). A metal regulatory element (MRE) (TGCRCYC) is found at position 89 (Culotta et al, Mol. Cell. Biol. 9:1376 (1989)). Two putative antioxidant response elements (ARE) (RGTGACNNNGC) are found at position 650 and 5022 (Rushmore et al, J. Biol. Chem. 266:11632 (1991)). A sis responsive element (SIF) (CCCGTC) important in the induction of the c-fos proto-oncogene is found in the reverse orientation at position 251 (Wagner et al, EMBO J. 9:4477 (1990)). There is an AP1 binding site or TPA responsive element (TRE) (TGACTCA) found at position 162 (Risse et al, EMBO J. 8:3825 (1989)). The SV40 enhancer region AP4 (CAGCTGTGG) can be found at position 171 (Jones et al, Genes Dev. 2:267 (1988)).

EXAMPLE VI

Screening Patients for Gene Defects in EC-SOD

Preparation of leukocyte derived genomic DNA frcm patients: Normal healthy control patients and patients with asthma, primary pulmonary hypertension, and secondary pulmonary hypertension will be identified. Genomic DNA will be purified utilizing a Qiagen Blood PCR Kit. One ml of blood containing ~$10^7$ leukocytes/ml will be collected in sodium citrate from each patient or control subject. The blood is placed into a QIAGEN-spin column and the leukocytes are entrapped in the resin by brief centrifugation, while erythrocytes and hemoglobin are washed through. The leukocytes are lysed by the addition of 0.7 ml of lysis buffer and incubated at room temperature for 30 minutes. DNA that is released, binds to the resin in the tube. Remaining cellular debris is washed away by multiple wash/spin cycles. The DNA is eluted by the addition of 1.2 M KCl, 50 mM MOPS, 15% ethanol, pH 8.3. This typically yields ~10 μg of genomic DNA (Reihsaus et al, Am. J. Respir. Cell. Mol. Biol. 8:334 (1993)).

Primer design and PCR amplification of EC-SOD exonic sequences: Sense and antisense oligonucleotide primers (or use primers already obtained from sequencing the genomic DNA) will be designed containing a 3' GC clamp (Sheffeld et al, Proc. Natl., Acad. Sci. U.S.A. 86:232 (1989)). These primers will encode the intronless coding region of the EC-SOD gene. A 172 bp region in the 3' untranslated region has been amplified using DNA sequencing primers and human genomic DNA. PCR conditions are as described (Reihause et al, Am. J. Respir. Cell. Mol. Biol. 8:334 (1993); Innis et al (eds) Academic Press San Diego pp. 1–12 (1990)) using Taq polymerase, with temperature cycling as follows: initial denaturation at 95° C. for 5 min followed by 35 cycles of 94° C. denaturing for 20 sec, 57° C. annealing for 15 sec, and 72° C. elongation for 45 sec. Because of the GC composition and actual primer sequence, it will be necessary to experimentally optimize conditions for PCR amplification using each set of primers. Three sets of primers will be used to encompass the entire coding region.

Identification of mutations with single-strand conformational polymorphism (SSCP) analysis: SSCP analysis has been used to detect single base pair mismatch (Orita et al, Genomics 5:874 (1989)). Temperature-gradient gel electrophoresis (TGGE) will be used to detect differences in mobility (Wartell et al, Nuc. Acids Res. 18:2699 (1990)). Samples for TGGE will be prepared by heat denaturing the PCR product at 98° C. for 5 min, then renaturing at 50° C. for 15 min with the corresponding wild-type DNA derived from PCR of the cloned gene. Electrophoresis will be carried out on a 5% acrylamide, 8 M urea gel over a temperature gradient. The temperature gradient will be optimized for each of the EC-SOD DNA segments. Typical gradients for the detection of $\beta_2$-adrenergic receptor mutations were between 35° C. to 60° C., and required 4 to 6 hours of run time (Rosen, Nature 262:59 (1993)).

All PCR samples found to be positive for mutations by TGGE will be sequenced directly using the dideoxy technique (Sanger et al, Proc. Natl. Acad. Sci. U.S.A. 74:5463 (1977)).

EXAMPLE VII

Inhibition of Xanthine Oxidase

Figure 25:
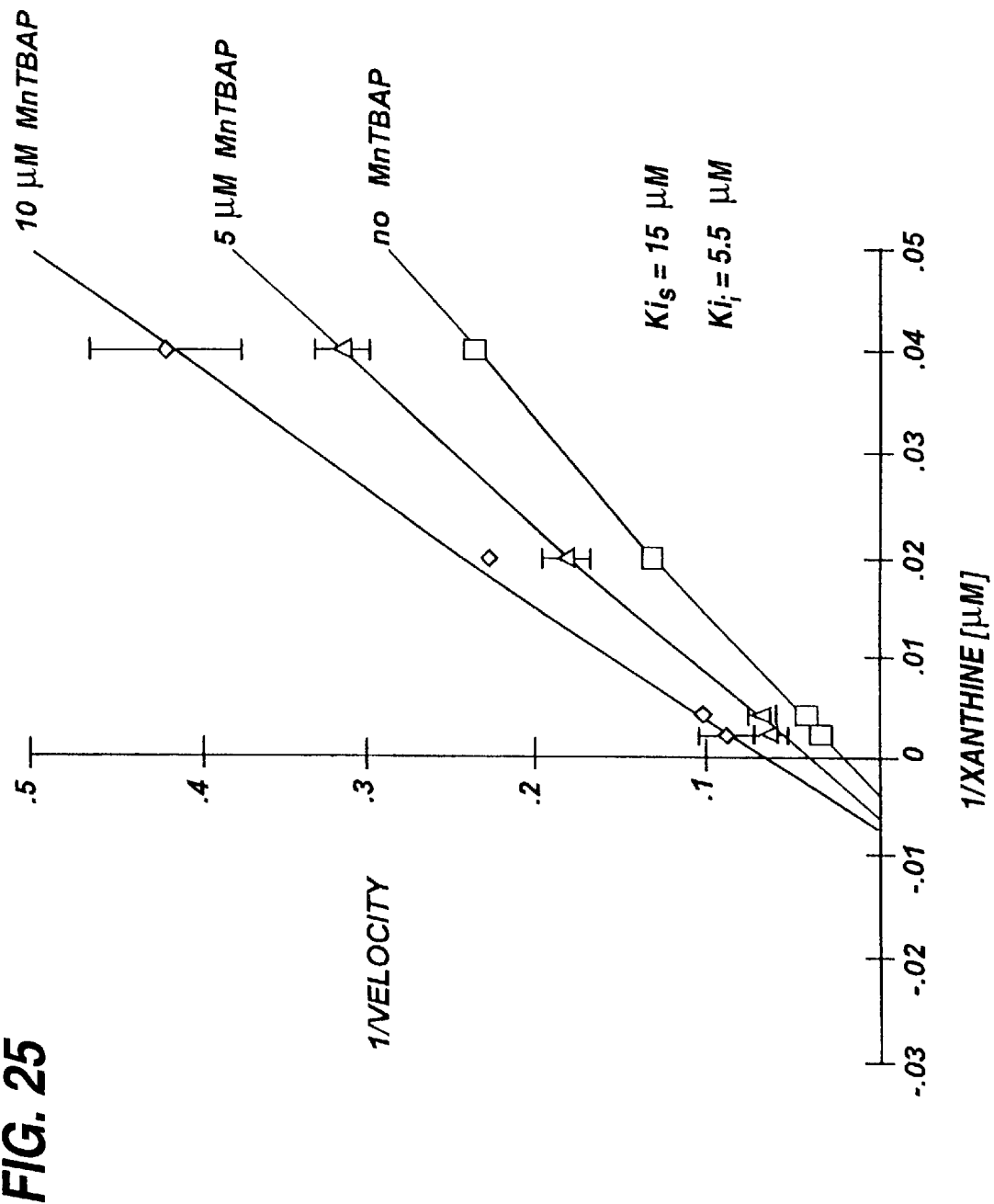
FIG. 25 shows a Lineweaver-Burk plot demonstrating non-competitive inhibition of xanthine oxidase by MnT-BAP.

In a first study, assays were performed in a 1 ml quartz cuvette containing 50 mM carbonate buffer, pH 10, 0.1 mM EDTA, 1 nM xanthine oxidase (Boehringer Mannheim) at 25° C. Xanthine oxidase activity was measured spectrophotometrically by following the loss of xanthine over time at 295 nm. Four concentrations of xanthine (25, 50, 250, 500 μM) and 2 concentrations of MnTBAP (5, 10 μM) were used. Two inhibition constants were then derived from the curve's intercepts (Kii=5.5 μM) and slopes (Kis=15 μM). The results presented in FIG. 25 show that MnTBAP inhibits xanthine oxidase in a non-competitive manner.

Figure 26:
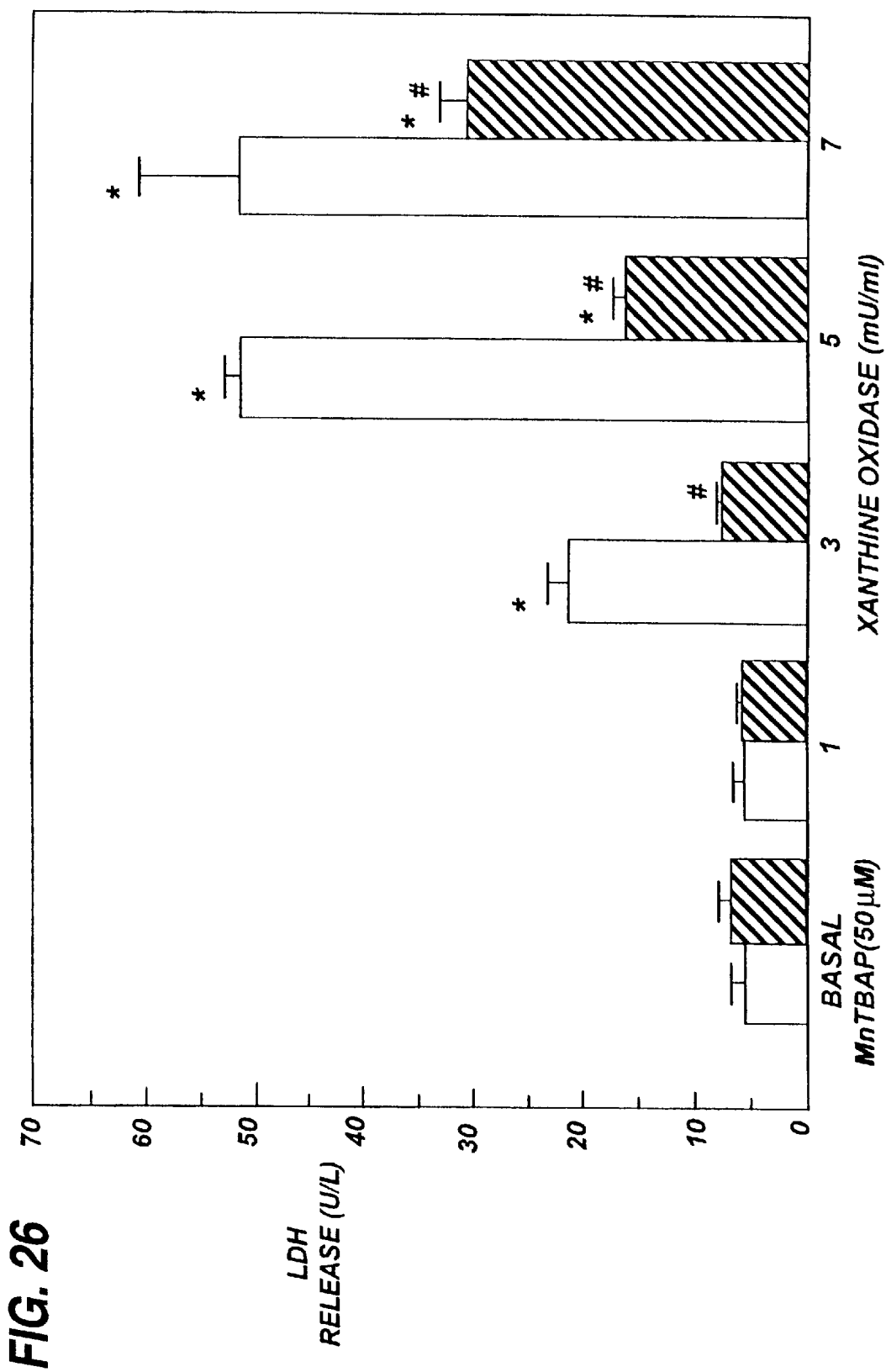

In a second study, calf pulmonary artery endothelial cell cultures (CPA-47 (Tissue and Cell 10:535 (1978)) were grown to confluence in Ham's F-12K medium with 10% fetal bovine serum at pH 7.4 and 37° C. Cells were then trypsinized and seeded at equal densities in 24 well plates and grown to 90% confluence. Cells were washed and pre-incubated for 1 hour with 50 μM of MnTBAP in minimum essential medium (MEM) or MEM only. Varing amounts of xanthine oxidase (XO) plus 200 μM xanthine (X) were added and allowed to incubate for 24 hours. Cell injury was quantitiated by measuring the release of cellular lactate dehydrogenase (LDH) into the medium. The efficacy of MnTBAP is shown in FIG. 26 by the decrease in XO/X-induced LDH release.

EXAMPLE VIII

SOD Mimetic Affords Cellular Protection From Paraquat-Induced Injury

Rat pulmonary epithelial cell cultures (L2 (Kaighn and Douglas J. Cell Biol. 59:160a (1973)) were grown to confluence in Ham's F-12K medium with 10% fetal bovine serum at pH 7.4 and 37° C. Cells were then trypsinized and seeded at equal densities in 24 well plates and grown to 90% confluence. Cells were washed and pre-incubated for 1 hour with 100 μM of MnTBAP or MnTMPyP in MEM or MEM only. Paraquat (2.5 mM) was added and allowed to incubate for 48 hours. Cell injury was quantitiated by measuring the release of cellular lactate dehydrogenase (LDH) into the medium. FIG. 27 shows that MnTPyP (hatched bars) and MnTBAP (grey bars) decrease paraquat-induced LDH release.

In a further study, calf pulmonary artery endothelial cell cultures (CPA-47 (Tissue and Cell 10:535 (1987)) were grown to confluence in Ham's F-12K medium with 10% fetal bovine serum at pH 7.4 and 37° C. Cells were then trypsinized and seeded at equal densities in 24 well plates and grown to 90% confluence. Cells were washed and pre-incubated for 1 hour with varing concentrations of MnTBAP in MEM or MEM only. Paraquat (2 mM) was added and allowed to incubate for 24 hours. Cell injury was quantitiated by measuring the release of cellular lactate dehydrogenase (LDH) into the medium. MnTBAP decreases paraquat-induced LDH release in a dose-dependent manner (see FIG. 28).

In contrast to MnTBAP, ZnTBAP does not protect against paraquat-induced injury. Calf pulmonary artery endothelial cell cultures (CPA-47) were grown to confluence in Ham's F-12K medium with 10% fetal bovine serum at pH 7.4 and 37° C. Cells were then trypsinized and seeded at equal densities in 24 well plates and grown to 90% confluence. Cells were washed and pre-incubated for 1 hour with varing concentrations of ZnTBAP in MEM or MEM only. Paraquat (2 mM) was added and allowed to incubate for 24 hours. Cell injury was quantitiated by measuring the release of cellular lactate dehydrogenase (LDH) into the medium. The results presented in FIG. 29 demonstrate that ZnTBAP does not possess SOD-like activity. ZnTBAP can be used as a negative control to show that the redox metal is important in the protection against paraquat toxicity.

EXAMPLE IX

Protection by MnTBAP Against Paraquat-Induced Lung Injury

Mice were treated with either paraquat (PQ, 45 mg/kg, ip) or saline (10 ml/kg, ip) and exposed to MnTBAP (2.5 mg/ml, nebulized into a 2 L chamber at 2 L/min for 30 minutes twice daily for 2 days) or room air. Mice were killed 48 hours after start of treatment and lung injury was assessed by analysis of bronchoalveolar lavage fluid (BALF). BALF damage markers used were lactate dehydrogenase (LDH, as units/L), protein concentration (as mg/dl), and percent of polymorphonuclear leukocytes (PMN). MnTBAP treatment provided partial protection against paraquat-induced lung injury (see FIG. 30).

EXAMPLE X

Catalase activity was measured by means of a Clark oxygen electrode using a modified assay previously described by Del Rio et al, Anal. Biochem. 80:409 (1977). Briefly, reactions were performed in a nitrogen degassed phosphate buffer (50 mM, pH 7.8) containing 0.1 mM EDTA at 25° C. Three concentrations of hydrogen peroxide (1–4 mM) and four metalloporphyrin concentrations (0.5–50 $\mu$M) were used to determine second order rate constants. The rate of oxygen evolution was followed for 2 minutes. The results are shown in FIG. 31.

Calf pulmonary endothelial cell (CPA-47) line was grown to near confluence in 12-well plates with F-12K medium containing 10% fetal calf serum. CPA-47 cells were loaded with $Cr^{51}$ as previously described by Simon et al J. Clin. Invest. 78:1375 (1986) in high glucose minimum essential medium (DMEM). Cells were pretreated with MnTBAP (100 $\mu$M) for 1 hour and then exposed to various concentrations of hydrogen peroxide generator, glucose oxidase, for 4 hours. Cell injury was then quantitated as the specific $Cr^{51}$ release from CPA-47 cells which has been adjusted for spontaneous $Cr_{51}$ release. The results are shown in FIG. 32.

Calf pulmonary endothelial cell (CPA-47) line was grown to near confluence in 12-well plates with F-12K medium containing 10% fetal calf serum. CPA-47 cells were loaded with $Cr^{51}$ as previously described by Simon et al (J. Clin. Invest. 78:1375 (1986)) in high glucose minimum essential medium (DMEM). Cells were pretreated with various concentrations of either: (A) MnTBAP; (B) MnTMPyP; (C) ZnTBAP; or (D) CuZnSOD for 1 hour and then exposed to the hydrogen peroxide generator, glucose oxidase (100 Mu/ml), for 4 hours. Cell injury was then quantitated as the specific $Cr^{51}$ release from CPA-47 cells which has been adjusted for spontaneous $Cr^{51}$ release. The results are shown in FIG. 33A–33D.

All documents cited above are hereby incorporated in their entirety by reference.

One skilled in the art will appreciate from a reading of this disclosure that various changes in form and detail can be made without departing from the true scope of the invention. In addition to the compounds described herein, compound disclosed in the following references can also be used as oxidant scavengers consistent with the invention: U.S. Pat. No. 5,227,405; Nagele et al, Biochem. Pharmacol. (UK) 47:555–562 (1994); Baudry et al, Biochem. Biophys. Res. Comm. 192:964–968 (1933); Duran et al, Cancer Lett (IRE) 69:167–172 (1993); Itami et al, Biochem. Biophys. Res. Comm. 197:536–541 (1993); Kitajima et al, Inorg. Chem. 32:1879–1880 (1993); Riley et al, Free Radical Biol. & Med. 15:514 (1993); Weiss et al, J. Biol Chem. (U.S.) 268:23049–23054 (1993); Foye, Ann. Pharmacother. 26:1144–1147 (1992); Haseloff et al, J. Biolumin. Chemilumin. (UK) 7:171–175 (1992); Pelletier, J., Biochem. Pharmacol. 43:1061–1066 (1992); Yaping et al, J. Free Radic. BiolMed 13:533–541 (1992); Schechinger et al, Biol. Met. 1:112 (1988); Linss et al, Inorg. Chim. Acta 125:117 (1986); and Weser et al, Adv. Exp. Med. Biol. 264:51 (1990).

---

What is claimed is:

1. A method of treating an inflammatory condition in a patient in need of such treatment comprising administering to said patient an effective amount of a mimetic of superoxide dismutase (SOD) or extracellular SOD (EC-SOD) comprising a porphyrin moiety, under conditions such that said treatment is effected, wherein the mimetic is of the formula:

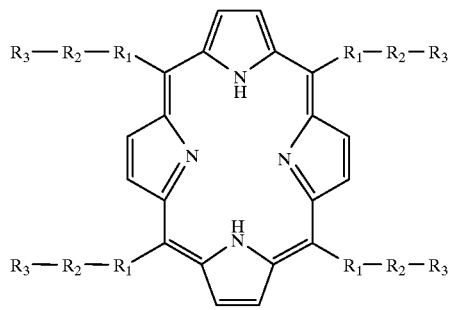

or a pharmaceutically acceptable salt thereof, wherein:

$R_1$ is a bond

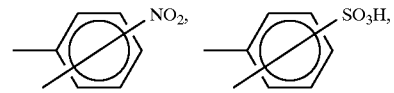

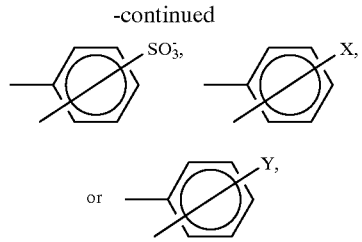

wherein X is a halogen and Y is an alkyl group and wherein

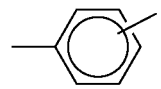

indicates bonding to $R_2$ at any position and

indicates bonding to $R_2$ and the substituent at any position; and $R_2$ is a bond $$—(CY'_2)_n^-, \quad —(CY'_2—CY'=CY')_n^-,$$

$$—(CY'_2—CY'_2—CH=CH)_n^-, \quad —(CY'=CY')_n^-,$$

or 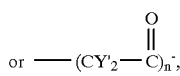

wherein Y' is hydrogen or an alkyl group and wherein n is 1 to 8; and

R$_3$ is —Y", —OH, —NH$_2$, —N$^+$(Y")$_3$, —COOH, —COO$^-$, —SO$_3$H, —SO$_3^-$, —CH$_2$—PO$_3$H$_2$ or —CH$_2$—PO$_3$H$^-$, wherein Y" is an alkyl group, optionally complexed with a metal selected from the group consisting of manganese, copper and iron.

2. A method of treating a disorder resulting from aberrant smooth muscle function in a patient in need of such treatment comprising administering to said patient an effective amount of a mimetic of SOD or EC-SOD comprising a porphyrin moiety, under conditions such that said treatment is effected, wherein the mimetic is of the formula:

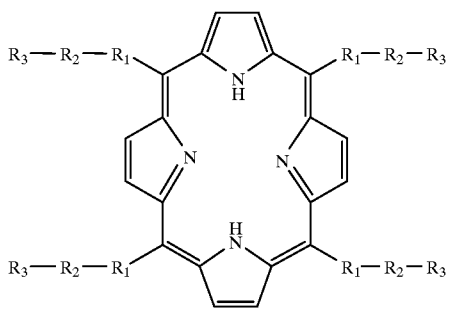

or a phamraceutically acceptable salt thereof, wherein:

R$_1$ is a bond,

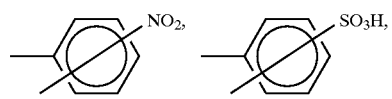

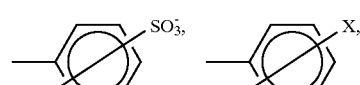

or 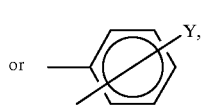

wherein X is a halogen and Y is an alkyl group and wherein

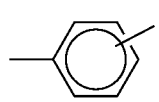

indicates bonding to R$_2$ at any position and

indicates bonding to R$_2$ and the substituent at any position; and

R$_2$ is a bond,

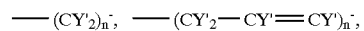

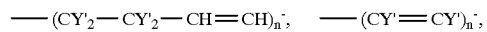

or 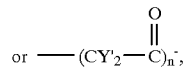

wherein Y' is hydrogen or an alkyl group and wherein n is 1 to 8; and

R$_3$ is —Y", —OH, —NH$_2$, —N$^+$(Y")$_3$, —COOH, —COO$^-$, —SO$_3$H, —SC$_3^-$, —CH$_2$—PO$_3$H$_2$ or —CH$_2$—PO$_3$H$^-$, wherein Y" is an alkyl group, optionally complexed with a metal selected from the group consisting of maganese copper and iron.

3. The method according to claim 1 wherein said inflammatory condition is an inflammation of the lungs of said patient.

4. The method according to claim 2 wherein said aberrant smooth muscle function is in the lung airways or vasculature of said patient.

5. The method according to claim 1 wherein —R$_1$—R—R$_3$ is

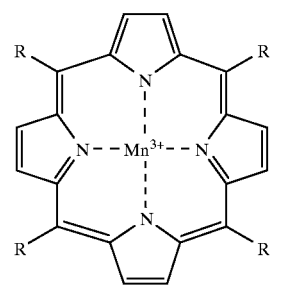

R = 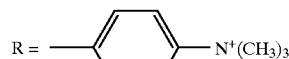

R = 

R = 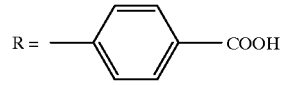

R = 

6. The method according to claim 2 wherein —R$_1$—R$_2$—R$_3$ is:

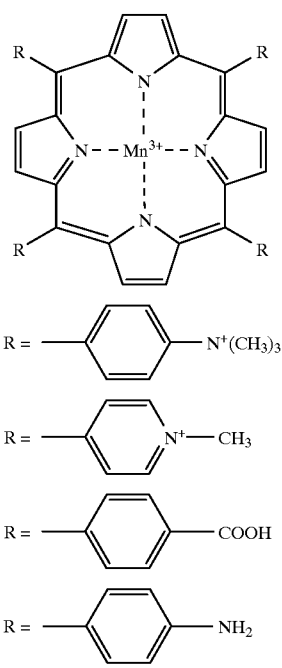

7. The method according to claim 5 wherein said inflammatory condition is an inflammation of the lungs of said patient.

8. The method according to claim 6 wherein said aberrant smooth muscle function is in the lung airways or vasculature of said patient.

9. The method according to claim 1 wherein a GAG binding moiety is attached to said mimetic.

10. The method according to claim 9 wherein said GAG binding moiety corresponds to the C-terminal end of EC-SOD, or portion thereof, having heparin binding affinity.

11. The method according to claim 9 wherein said GAG binding moiety comprises a repeat of positively charged amino acids.

12. The method according to claim 2 wherein a GAG binding moiety is attached to said mimetic.

13. The method according to claim 12 wherein said GAG binding moiety corresponds to the C-terminal end of EC-SOD, or portion thereof, having heparin binding affinity.

14. The method according to claim 12 wherein said GAG binding moiety comprises a repeat of positively charged amino acids.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 15 amino acids
      (B) TYPE: amino acid
      (D) TOPOLOGY: linear (ii) MOLECULE TYPE: protein (xi) SEQUENCE DESCRIPTION: SEQ ID NO:1:

```
His Arg His His Pro Arg Glu Met Lys Lys Arg Val Glu Asp Leu
1               5                  10                  15
```

(2) INFORMATION FOR SEQ ID NO:2:

(i) SEQUENCE CHARACTERISTICS:
      (A) LENGTH: 18 amino acids
      (B) TYPE: amino acid
      (D) TOPOLOGY: linear (ii) MOLECULE TYPE: peptide (xi) SEQUENCE DESCRIPTION: SEQ ID NO:2:

```
Arg Glu His Ser Glu Arg Lys Lys Arg Arg Glu Ser Glu Cys Lys
1               5                  10                  15

Ala Ala
```

(2) INFORMATION FOR SEQ ID NO:3:

(i) SEQUENCE CHARACTERISTICS:

(A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:3:

Arg Glu His Ser Glu Arg Lys Lys Arg Arg Arg Glu
1               5                  10

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:4:

Arg Glu His Ser Glu Arg Lys Lys Arg Arg Arg Ala
1               5                  10

(2) INFORMATION FOR SEQ ID NO:5:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:5:

Arg Glu His Ser Glu Arg Lys Lys Arg Arg Arg Ala Ser Glu Cys Lys
1               5                  10                  15

Ala Ala (2) INFORMATION FOR SEQ ID NO:6:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:6:

Arg Glu His Ser Glu Arg Lys Lys Arg Arg Arg Glu Ser Glu Ala Lys
1               5                  10                  15

Ala Ala (2) INFORMATION FOR SEQ ID NO:7:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:7:

Arg Glu His Ser Glu Arg Lys Lys Arg Arg Arg Glu Ser Glu Cys Ala
1               5                  10                  15

Ala Ala (2) INFORMATION FOR SEQ ID NO:8:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:8:

Arg Glu His Ser Glu Arg Lys Lys Arg Arg Arg Ala Ser Ala Cys Lys
1               5                   10                  15
Ala Ala (2) INFORMATION FOR SEQ ID NO:9:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:9:

Arg Glu His Ser Glu Arg Lys Lys Arg Arg Arg Ala Ser Glu Cys Ala
1               5                   10                  15
Ala Ala (2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ATGACCTCCT GCCAGATCTC C                                                     21

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGGCAGGAAC ACAGTAGC                                                         18

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TGGGTGCAGC TCTCTTTTCA GG                                                    22

(2) INFORMATION FOR SEQ ID NO:13:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TCCAGCTCCT CCAAGAGAGC                                               20

(2) INFORMATION FOR SEQ ID NO:14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TGCGGGGTGG AC                                                       12

(2) INFORMATION FOR SEQ ID NO:15:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GGAAAGGTGG GT                                                       12

(2) INFORMATION FOR SEQ ID NO:16:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GCCCAGGCTC CA                                                       12

(2) INFORMATION FOR SEQ ID NO:17:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CCGCAGGTGC CC                                                       12

(2) INFORMATION FOR SEQ ID NO:18:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

RGTGACNNNG C                                                               11

(2) INFORMATION FOR SEQ ID NO:19:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CAGCTGTGG                                                                   9

(2) INFORMATION FOR SEQ ID NO:20:

(i) SEQUENCE CHARACTERISTICS:
        (A) LENGTH: 10079 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 5086..5803

(xi) SEQUENCE DESCRIPTION: SEQ ID NO:20:

```
GGATCCAGAG ATTTAGATTT TTTATAAGCT TTCCTGCCAC CGAAACGGGT GTTTGGGACC       60

TCACGAGGCC CTGTTCATTC TTCGTCGCTG CGCTCCCCAC TCTGTACTGG ATGCATTTAC      120

TGACGTTGTT GTCTCCGTCC CCAGAGTATG AACCCCCAAG GTGACTCATG CAGCTGTGGG      180

TGCCCGGCAT ACAGCATGGT GACTGGAATG GATGAGCACC CAATAAACAT TTGTTGCAGG      240

AATGCAGGAG GACGGGCAGG CCAGCAAGCA GGCTGCCTGG TTTTTCCCAC ATGGGCTTTT      300

CTGGGAAAGA AGAGCTTCTA TTTTTGGAAA GGGCTGCTAT GATTGAGAAA AGTTCATGGC      360

AGCAAAAAAA GGACAGACGT CGGGAGGGAA ACACTCCTAG TTCTCCCAGA CAACACATTT      420

TTTAAAAGA CTCCTTCATC TCTTTAATAA TAACGGTAAC GACAATGACA ATGATGATTA      480

CTTATGAGTG CGGCTAGTGC CAGCCACTGT GTTGTCACTG GGCGAGTAAT GATCTCATTG      540

GATCTTCACG GTGGGCGTGC GGGGTGGACA GCCTCACACC CCCATTTTAC AGATGATGAA      600

AAGGAGGTGC AGGGAGTGGT GCAGCTGCTT CAGGCGTACA CAGATAGGAA GTGACAAGGC      660

TGGGACTCTG CAGCCTGAGT GTGTCATCAC GACCCACCCG CTGCTCTGCT CTCATAGGTA      720

TGACAGCACA GCTCTGGAGC AAATGCCATG CACATTTGCA AGGTGCCCAT TTCCATGCAG      780

CAAAAATAAG TCAATAAGTT ATTGACTTAG AGAAAAGCAA AGGGCCTCTC AATAAAGAGG      840

TCATTGTACA CCTCTCCAAA CAGGCGATTT TCTTTCTCAT TTTTATTCCC CTGCTGTGTG      900

CTGAAGGTCA CTGGCTACAA GCCGGTGAAG TCGCGGAATG GAATCCTTGG CCCGAAAACC      960

CAAAAATGGG AGGGGCAGAG GAGGTGGGGA CAGAGCGGGA GGAGGTGGAG GCGAAGCAAT     1020

TCTACAACCC GGGGAGGTCT GGCCTGCTTT TCCTCCCTGA ACTGGCCCAA TGACTGGCTC     1080

CCTCACGCTG ACCACTCCTC TGGGCTGGCC TCCTGCACTC GCGCTAACAG CCCAGGCTCC     1140

AGGGACAGCC TGCGTTCCTG GGCTGGCTGG GTGCAGCTCT CTTTTCAGGA GAGAAAGCTC     1200

TCTTGGAGGA GCTGGAAAGG TGGGTGCTAA GTTGAGGTTC ATTTTGTTCT TCTCGGAGTG     1260
```

```
TGCTTATTGA GTCTGAAGCT GGGTTGGGGC AACGGGCCTC TTCTTGGGAA CAAATTGGAT    1320

CATCTTCTTG GGAAGGAAAT GTACTTTCCC TGGCTGCTCT GAGGGGTTAG TGGGGAGGTG    1380

GAGTGAGCGG GGAGGAAGGC AAGGAGGGGA GGAAGAAACC GTTCCTCCTG TGGATCTGCA    1440

AAGACCAGTC CAAGAGGATT TTAGTGTTAG GAAAAGGAAT CTGGAGTGAC GAGAAAGGGG    1500

GCCTTTCTAG ATGTTGCATG GCTTTGGTGT CGGGAGCCAC TTATGGGACA GCAGGTACTC    1560

TAAAAAGCCA CCTCCTTAGG AAAGCAGAGA GGCCCTGGCC AGCTCAGGCT CCCAGCAAGA    1620

GCTCCTTCTA GGAGACAGCT GAGGGATGAA ACACACCCAA GGCTCAAGAG GGCAGGTTC     1680

TTCCCAGATA CAGACCCAGG AAGGAGATAA AGGCTTGGTG CCTCTATTTG GTTCAGGATA    1740

AGGGCCCCTG TCCTCTTTCT CTGATAACAC TGTCCTCTTT CTCTGATAAC ACCGTCCTCC    1800

CTTCCAGATC CACGTACAAA GGAGGCCCTT AAAAAGGCAC TTGGTCATTC ACAGCTCAAA    1860

CTGAGCAAGA GGCTGTGGGA GAAGAATCAA GTTGGTCCCG AGGGGAAGAG GTGTCAAAGG    1920

CTTAAGAAAC AAGAAGTCAG AGTTTACCTG GGTTTGAGGG AGAATTTTCT TTCCCCCTTT    1980

TCCTCCTCCT CCTCCTTCTT CTCTTTTTTT TTTTTTTTTT TTTTTTTTTT TTGAGACATG    2040

GTCTCATTCT GTCACCCAGC ACCCAGGCTG GAATGTAGTG GCACGATCAC TATCACGGCT    2100

CACTACAGCC TCTACCTCCC GGGCTCAAGT GATCCTCCTA CCTCAGCCTC CTGAGTAACT    2160

GGGACTACAG GCACATGCCA CCACACCCAG CTATTTTTTT TTTTGCTAGA GATGGGGTC     2220

TCTACCAGGT TGGTCTCATA CTCTTGTACT CAAATGATTC TCCTGTCTCA TCCTCCCAAA    2280

GGGTGGGATT ACAGGCATAA GCCACCATGC CTGGCTCTTC TTTTGGTTTC AGAGAAAAAC    2340

ATCTCCTTAA AATGTTTATT TCCCAAGGAT TCTTGAAAAA GAAAGCTCAC TGACACACCC    2400

AAAACAATCT GGTTTTGCTC TGTGCTTTTA GGGAGAACTT TCTAAGCAGC AGAGCCCTTC    2460

TGAGTGGCAG GGCTGTCTTA GGAGGAAGGT GTCTTTTGAT GATGGGGAAC TTCATGTCCA    2520

GGTCTGGCAG GAGAGTTACC CCACTTTCCT GCCTACTCCC TGGGGCTTTG GGTAGTAGT     2580

ACCACATTGG GCCATGTCAT TTAGGTGAGT CCTTCAACAT CACTTTCTCT GCTTCTCCCT    2640

CTTTCTGGAT CCTCCTTCTT GGAGCCTTTC AAGGGGACCT CCTCTCACAG TGTCCATAGC    2700

ATCTCTTAGC TAATGGTCCT TAAAATCTCT ACCAGCAGCT TCTCTCTGAT AGCTAAGAGC    2760

TGCCATTTAC TGGGAACTTT CTATGTACTG GGCTCTGTGC TAAGTGCCCT AGATGAGAGA    2820

TGTGCAGTGT GGTGCCTAAA CCTTGGGCTT GGAGCAGACA CACACTTTCA AATCCTGCCT    2880

TCAGCTCCTT AGTGAACATG TCACCTTGGG CGGGACACAC GCCTCTCTGT GCCTCAGTTT    2940

CCTACACTTT AGAATGGGGA TAACACTGAA TAATGTTCTT GTGAGGATGC AGGGAATTAA    3000

CCCACGCACA GTACTTATAA TAGTGTCTGG CGCCTGTGTT CGATAAGTTT TAGCAATTCT    3060

AATCATCTCT TTTAAGCCTC GCAGCAAGCC TCTAAGGTAA GTCTGTATTA GTATCCCTAT    3120

TTACAGATGA GAAAACTGAG GTTCACAGGG GATGAGACAG TGTACAGTCT GCAGTCCAGC    3180

AATTACTCTG CTACTCAGCA ATAAAAATAG TAACAGCTAA CCCTTAGACT AAGTGGCAGA    3240

GTCAGGCTTT AGATTCATGA GGTGAGTTCT GGAATCCATC CCTTTAATAA CCACACTAAA    3300

TTGCCTTTCT GAAATGGTTA TATAAAGCAT ATCTACCCAA TCTTGGAGTT TTTTAAATGG    3360

CACCTAGTTT GGTGCTGGAA ATGCAGTTGA CCTTCAAAGC AATTCTTTGG AGGCAGCATC    3420

AATCCCTCTG GAAATACCTC GGTGGCATGG CTGGCCTTAT TCTACAGGTA AGGAACTTGA    3480

AGCTAAGCAT CAGTAACCCC GTGAAGTCAC AGTTAGTATA GGTTGGAATT GGGATTCAAA    3540

TCTGTACCTG ACTTTATAAT TCCTAGCTGG GCCCCAGAAT CTTTGATAGA GGTGTCTTCT    3600

TTCTTTTCTT TTCTTTCTTT CCTCTTTCTT TCCCTTCCTT CCTCTCTCTC TGTCTTTCTT    3660
```

```
CTCTCCTTTC TTTCTCACAG AATCAAAATC TCTTGGGGTG GGGCCTGGGC ATCTGATTTT      3720

TAAAAACCAG ACATCTGATG TGCAGTCAAC ACTGAGAACC CCTGCCAGCT TCATCTCCTC      3780

TTCTAAGTGC CAGACCCAAG TTTCAACTG TCTGCCCACC TGTCTCCCCA CCTGGGCACC       3840

CGCCAGCGTC TCACCCTCAG GAGACTCCAG CTGAACTAAT CCTCTCTCCC TGCTTTTCCA      3900

GAACAGGTCC CACCCTCCCT CCACTCAGTC TCTCCTGCTG GGAACCCTGG TCATCTGCAC      3960

TGTGCCTTCA TCTTCCATCC TGCCAGTGCT GCCCGGTGTG TCTCTTAAAC CCATGCCTCC      4020

TCTGTGTGCA CCACCTGCAC TTTGGTAAAA GCCTTCATTT CCTGCTTGGG TTACTACAAC      4080

GCCCCCTAAC TCATCTCACT GTCTCTATTT CTGCTTCTCT GTCTCTCCCT AGGCTACTCC      4140

CATTCTTCCT CCCCTTTCCT CTTCATCCCA AGTCCAACC CATATCCTTT TACCAGTAGG       4200

ACTTAAGGAA CTAAAGACTA TCTCATCACC CACTTTTCTT CTTAAAAACT TCCACTGCAC      4260

TGCCTGCTGA GATGGCCTTC CTACCCAACT TGGCTGGAAA ACTCCTACCC ATCTTGTGGA      4320

ACCCAGTTCA AAAGTCACCA CCTCTGAGAA GCCTTCCCTG AGGCTCCTAG GGAGATGGGT      4380

ACTGCCTCCT CTGTCCTTCT CCAGCACAGG CCCCATCTTC AATCACAGGA TTGTGCTGGA      4440

ATGATTGGAT GCCAAGTCTG TCCCTCACTG AACTCCTTAT GCAAAATCCA TATTATATGT      4500

TTCCTTTTGC CAGGTGTGGG CCCAGGTGCT GGGGATACCG ATGAATAAAA CTGAGTTTCT      4560

GTCTTCAAGA AGCTCCAAGT CTACTGAGTG TAGCAGAGAA CAGGGAGAAG GCACTTCAGG      4620

GAGAAGGGGT AGCACATGCA AAGCCCCAGA AGGCAGGGAC AGAAGCCTTA GGGATGTCTG      4680

TGGGGGAGGA TGGAGGAAGA GGGTAACAGG AGACCAGGTG GGGAGATGAG GGAGGTGGTC      4740

TGGAAGGGCC ATGAGACACC CCTCACGCTC CCTGAGACCC CCTCCACGCT ATAGAGATGG      4800

GACTGGAGAG GACGATGATC ATTTGTGACT CAGATCCCTG TGGGTTTCTT CAGATTGGGT      4860

CTCACCCATC TTTACAGCCA CAGCACCTAA CACAGTGCCC GGCACACAGC AGGCCCTAGA      4920

CAAACGTTTG CCACATGAAG TCATGCCACT GGCCAGGAAG CCCACTGGGG ACTGGGGGT      4980

TGGTTCTGCG ATAATGGGGT CCCTGAGATT CTATGTTTCA CGTGACTAAG CCTCACTCTG      5040

CCCCCACCTC CGCGGGGCG TCCCGCAGGT GCCCGACTCC AGCCA TGC TGG CGC           5094
                                                Cys Trp Arg
                                                  1

TAC TGT GTT CCT GCC TGC TCC TGG CAG CCG GTG CCT CGG ACG CCT GGA        5142
Tyr Cys Val Pro Ala Cys Ser Trp Gln Pro Val Pro Arg Thr Pro Gly
  5              10                  15

CGG GCG AGG ACT CGG CGG AGC CCA ACT CTG ACT CGG CGG AGT GGA TCC        5190
Arg Ala Arg Thr Arg Arg Ser Pro Thr Leu Thr Arg Arg Ser Gly Ser
 20              25                  30                  35

GAG ACA TGT ACG CCA AGG TCA CGG AGA TCT GGC AGG AGG TCA TGC AGC        5238
Glu Thr Cys Thr Pro Arg Ser Arg Arg Ser Gly Arg Arg Ser Cys Ser
                 40                  45                  50

GGC GGG ACG ACG ACG GCA CGC TCC ACG CCG CCT GCC AGG TGC AGC CGT        5286
Gly Gly Thr Thr Thr Ala Arg Ser Thr Pro Pro Ala Arg Cys Ser Arg
             55                  60                  65

CGG CCA CGC TGG ACG CCG CGC AGC CCC GGG TGA CCG GCG TCG TCC TCT        5334
Arg Pro Arg Trp Thr Pro Arg Ser Pro Gly  *  Pro Ala Ser Ser Ser
         70                  75                  80

TCC GGC AGC TTG CGC CCC GCG CCA AGC TCG ACG CCT TCT TCG CCC TGG        5382
Ser Gly Ser Leu Arg Pro Ala Pro Ser Ser Thr Pro Ser Ser Pro Trp
     85                  90                  95

AGG GCT TCC CGA CCG AGC CGA ACA GCT CCA GCC GCG CCA TCC ACG TGC        5430
Arg Ala Ser Arg Pro Ser Arg Thr Ala Pro Ala Ala Pro Ser Thr Cys
100                 105                 110                 115

ACC AGT TCG GGG ACC TGA GCC AGG GCT GCG AGT CCA CCG GGC CCC ACT        5478
Thr Ser Ser Gly Thr  *  Ala Arg Ala Ala Ser Pro Pro Gly Pro Thr
```

-continued

```
                   120                 125                 130
ACA ACC CGC TGG CCG TGC CGC ACC CGC AGC ACC CGG GCG ACT TCG GCA    5526
Thr Thr Arg Trp Pro Cys Arg Thr Arg Ser Thr Arg Ala Thr Ser Ala
                135                 140                 145

ACT TCG CGG TCC GCG ACG GCA GCC TCT GGA GGT ACC GCG CCG GCC TGG    5574
Thr Ser Arg Ser Ala Thr Ala Ala Ser Gly Gly Thr Ala Pro Ala Trp
            150                 155                 160

CCG CCT CGC TCG CGG GCC CGC ACT CCA TCG TGG GCC GGG CCG TGG TCG    5622
Pro Pro Arg Ser Arg Ala Arg Thr Pro Ser Trp Ala Gly Pro Trp Ser
        165                 170                 175

TCC ACG CTG GCG AGG ACG ACC TGG GCC GCG GCG GCA ACC AGG CCA GCG    5670
Ser Thr Leu Ala Arg Thr Thr Trp Ala Ala Ala Ala Thr Arg Pro Ala
    180                 185                 190                 195

TGG AGA ACG GGA ACG CGG GCC GGC GGC TGG CCT GCT GCG TGG TGG GCG    5718
Trp Arg Thr Gly Thr Arg Ala Gly Gly Trp Pro Ala Ala Trp Trp Ala
                200                 205                 210

TGT GCG GGC CCG GGC TCT GGG AGC GCC AGG CGC GGG AGC ACT CAG AGC    5766
Cys Ala Gly Pro Gly Ser Gly Ser Ala Arg Arg Gly Ser Thr Gln Ser
                215                 220                 225

GCA AGA AGC GGC GGC GCG AGA GCG AGT GCA AGG CCG C CTGAGCGCGG       5813
Ala Arg Ser Gly Gly Ala Arg Ala Ser Ala Arg Pro
                230                 235

CCCCCACCCG GCGGCGGCCA GGGACCCCCG AGGCCCCCCT CTGCCTTTGA GCTTCTCCTC  5873

TGCTCCAACA GACACCTTCC ACTCTGAGGT CTCACCTTCG CCTCTGCTGA AGTCTCCCCG  5933

CAGCCCTCTC CACCCAGAGG TCTCCCTATA CCGAGACCCA CCATCCTTCC ATCCTGAGGA  5993

CCGCCCCAAC CCTCGGAGCC CCCCACTCAG TAGGTCTGAA GGCCTCCATT TGTACCGAAA  6053

CACCCCGCTC ACGCTGACAG CCTCCTAGGC TCCCTGAGGT ACCTTTCCAC CCAGACCCTC  6113

CTTCCCCACC CCATAAGCCC TGAGACTCCC GCCTTTGACC TGACGATCTT CCCCCTTCCC  6173

GCCTTCAGGT TCCTCCTAGG CGCTCAGAGG CCGCTCTGGG GGGTTGCCTC GAGTCCCCCC  6233

ACCCCTCCCC ACCCACCACC GCTCCCGCGG CAAGCCAGCC CGTGCAACGG AAGCCAGGCC  6293

AACTGCCCCG CGTCTTCAGC TGTTTCGCAT CCACCGCCAC CCCACTGAGA GCTGCTCCTT  6353

TGGGGGAATG TTTGGCAACC TTTGTGTTAC AGATTAAAAA TTCAGCAATT CAGTACTGCG  6413

TCGAGGTCTT GGTTACTTTT TTGTTTGTTT GTTTTAGGCT TCTCTCCCAA GCTGAGCTTT  6473

TTTTTGTTTT GTTTTCGTTT TCCTTTTTTT TCTTTTTTTT GGGAGTGGCA AACATGCTTC  6533

CCAAATCCCT ACAGGACTTC TCCTTATCCT CTGCCCCCAC CTCCCTAACC CTGCTGGCAA  6593

CAACGTTCAG CCACTGCTTG TCTTGCCCTT CAGTGTGGCT CCAAGAGGAA GATCACCAGA  6653

ATCACTCAGG GAAGTTAAAA AAAAAAATAC AGCTTCCTGG GCTACATCCC AGAGCTGTGG  6713

AATCCAAAGG GAGAAGAGAA AGTGAATTTG CGACAAGCGT CGGGATGATT CTGGCACTGG  6773

ACCCTCTGGC CTGAGAGGGG AAGAGGCCTT CCATCTCACC TGGGCTGGTA GCTTGTCACA  6833

TCTGCCTCCG AGTACAGCCT TAGGTCCATT TCCCAGATAT CAGAGACAGT GCCAGGGAAG  6893

CCAGGTGACT GCATCTTGCC TAGGCACAGA AGAGTAGGGT TGGAATGTGA CGTTGTTAGC  6953

ATTTGGCAGG ACCAAAACCA GAGGCAAACG GAGGCAGTGG GATGGAAAGG CAGTTGATTT  7013

TGATGAAGGC TTGTTGGGAG TTCAGCTTTC TTTTGAAACT TATAATCTAT ACCCAGGCTA  7073

GAACAGTCTT GTGTATACAC CTTCATTCAT GGAATAAACG TACTTGCAAT AACTTTTTAG  7133

CCTCCCAGGG TAGCCTCACT TCCTAGCTGT GACTTTTCCA CCCTGGTTAC TGGGAGGCAG  7193

CTTCCATTTC TCCCAGACTA GCTAGGCAGT GCGTCCAACT GAACCGCAGC CAGAAACCTG  7253

TCTCCAGGGG TTATTTTTAC CTCTAACTAG GACTAACTTA TTTTAAAATC TTTCCTTGAG  7313
```

| | |
|---|---|
| CCCAAGTGAC AACTGAAGAG AAAGGCTATT GCCTGGTGAT TTTGCTCCAC CAGTTGGTTC | 7373 |
| TCACTGGTTT GAATACTAAC TTGAACTGTA CTCATCGACA CTGAAAGGGG ATGAGCAAAC | 7433 |
| AGTGTCTCTA AATCTCCTGA TCCTGATCTC AAATATCCCC CTAATTACAA GTTGCAACAA | 7493 |
| GGCAGCTATT ACACGGGGAC ACAGGATGGA GAGGATGGGT GCCAAACACC CATCGTCTAC | 7553 |
| TCTGCTGCCT CGGTTATGGT GAATTCAGGA CCATCAAGGG AGGTGTGGAC CTTTTTTTTC | 7613 |
| AGAAGGAGGC TGACACTTCT TGTCAATTGC ATTGTGTTCT TAGTTTTGCT CTTCACAACC | 7673 |
| CTTGACCCCG TAGATGGGGG CTGAAGAGGC ACCCTGGCCG ACTCACTCTA TTTCTGTTTT | 7733 |
| GGGAATGGGA TGGATAAACT ATCCCATGGC CTCCAGAGCC AAAAAACCAA AACGAAACAA | 7793 |
| AACAAAAAAC CCCAAAACAA AAAGCAAAA AGCAAACAAG AAAAAAAAAA AAAGAGGAAA | 7853 |
| TAATAGGCAG ACAATTTACA GTTCATTGTA AGGGCAAAGA TATGCATATA GCATGATGGT | 7913 |
| TAACAGGTCA GGCTCAGGTA GAAAGGCCCA TTTGAACCCC AGCTCTGCCA CACTCAGAAA | 7973 |
| CTGTGTGACC CGAACAAGTC ACTTAACCTC TCTGAGCATA GGTAAAATAA GATCATCATA | 8033 |
| CCAGATTGTT TTGAAGATTA AATCAAGTGT TATTCACGAG AGGTGCACAG CATAGCATGC | 8093 |
| ACAACAAATA AGGACCTGGT AAGTATCTAA TTAATAACAA TGGCTAAGAT CCAAAAAACA | 8153 |
| GCTACCTACT AATAAATAGA TGGGGCTGCC TTGTAAGGCA GTGAGCATCA TGCAACCAGG | 8213 |
| ATTCAAATGA AGGACAGTTG CTACCTCTGA GGTTCCCGAG AAGGATTTCT CGATCCATTG | 8273 |
| AGAGACTGAA TGACATGAAC TCTGCGATCC CATCTCTTGT GGGGAGGGAA CCTAGAATGA | 8333 |
| AGGGAAGATT GTGGGCCATA AAGGCAGACA TCTGGTTCCT GGGCACAGAA CCATATGTGT | 8393 |
| GCCACCAAAG CCACCCACCG GACCCCACTT GGCCCCTGGA GTCTATTTTT ACTCCTCTCA | 8453 |
| TCTTACAAGA TCTATTTTGT TAATCTCCTT ATATTTGCTG TTTTGACTTC CCAGCCAGCT | 8513 |
| TGCTAATCAG TTTGCCTATT TGACTCACAG GGTTTGCATT TGTCACGGGG ACTGAAACAC | 8573 |
| ACGCTTGTTT TGATTTCTTT TTGTAAATTA GAAGCGTTGA TGTAATGACT CTACCTAGAC | 8633 |
| ACAGCTGGTA AAGTGAGAAT AATGCTCAAG TTTGCACAGT TTAAACACAA TGTAGACAAT | 8693 |
| AATTAGAAAT GCTATCTTTA GATGTTTAGG ATAAGCTTTT CTCAGAATTG CACTGATTTT | 8753 |
| TTTTTTCTGA GTGGGCTTT TTAGTGCATA TATACAGAAA TACTAAAAAC GTAAGAAAAT | 8813 |
| AGAGCAAATC AGTGAGTGCT TTGGTCAACT TGAAAGACTG CAGGAAATAA ACCAACTGAT | 8873 |
| TTTAGATCTG CCTTTTTTTG ACTGAATGCA TAAAATCTTT ACATTCTCCA TATTTTTCAT | 8933 |
| GACTACCATA TGATCAAATA GTTTTAGGTG ACAGATTGCA ACTGATAAGT TGCTGCAATA | 8993 |
| TGGCAGAAGT CATGCTCAGC CTCCGCTTGC CCGGTGGTGA GGGTGGAATA TGAAGCAAAC | 9053 |
| AATAAAGATA ATTCATCATC TCTATCAGGA AAATTGCCAC ATGTTTATTT CAGGTAACAA | 9113 |
| AAAAGATATA GTTATGATAT ACAATGACCA TAGAATCCAA TAAAGCAACT TCTGCAAATG | 9173 |
| AATAGAAGGT ACTTTTTCTT TAAATGAAAC TACAAAATAG CAGCTGGTTT TAAAAACAAA | 9233 |
| GCCAATTGTT TTAGATTTAA TAGGCTACCA CTGGCCTCTG CTAAGATCCC CAAATATATT | 9293 |
| CCTGAGCTCA CATAGATTCC AGAAAGTCAA ACTTTTCAAT ATTATGCAAA CTTTCCCTAT | 9353 |
| GCATCCAAAA AATTCTCATT TAGTAAAGAG GTGATATGAA ATGTAAGGCA GCATGTCCAT | 9413 |
| ATCTATCATT TTAAATTGCC TTCATGCTGT ATCAACTGGT TTTGTTTTGG GAAGCAACCA | 9473 |
| TAATATTGAG AGACGGGTCT TTCCTATTTT TTCTGCTACT CATTTCTAAC TAGATTCACT | 9533 |
| ACGGAGCTCC CAATTGCATC TCTCTGATCT ACAAATTTTT CTCTCTTCAG GAAGACACCT | 9593 |
| GGAAAGAAGG GACTACATTA AAGGAGTGTG TTGGGGGCAA TGCTTTGGCC TTTTGACATC | 9653 |
| CTATCTAGTC TGAAGGGACC CTCACTATTG CTAAGGAGGA GGAGTGTTTT AAATGGAGGC | 9713 |

```
TTCAGAATGA AAGCAGAGGA AGAAGGTACT CTCTTTTTCA AAAAGAAGGA GGGTACAGGC    9773

CGGGCGCAGC TGTCACGCCT GCAATCCCAG CACTTTGGGA GGCCGAGGAA GGCAGATCAC    9833

GAGGTTGGGA GTTTGAGCCA GCCTGGTCAA CATAGTGAAA CCCCGTCTCT ACTAAAAATA    9893

CAAAAATTAG CCAGCATGGT GGTGCATGCC TGTAGTCCCA GTTACTCGGG AGGCTGAGGC    9953

AGGAGAATCG CTTGAACTCG GAAGTGGAG GTTGCAGTGA GCCGAGATCA TGCCACTGCA    10013

CTCCACCCTG GGTGACAGAG TGAGACTCTC AAAAAAAAAA AAAAAAAAAA AAAGAAGTAG    10073

GGTACC                                                                10079
```

(2) INFORMATION FOR SEQ ID NO:21:

(i) SEQUENCE CHARACTERISTICS:
        (A) LENGTH: 77 amino acids
        (B) TYPE: amino acid
        (D) TOPOLOGY: linear (ii) MOLECULE TYPE: protein (xi) SEQUENCE DESCRIPTION: SEQ ID NO:21:

```
Cys Trp Arg Tyr Cys Val Pro Ala Cys Ser Trp Gln Pro Val Pro Arg
 1               5                  10                  15

Thr Pro Gly Arg Ala Arg Thr Arg Arg Ser Pro Thr Leu Thr Arg Arg
            20                  25                  30

Ser Gly Ser Glu Thr Cys Thr Pro Arg Ser Arg Arg Ser Gly Arg Arg
        35                  40                  45

Ser Cys Ser Gly Gly Thr Thr Thr Ala Arg Ser Thr Pro Pro Ala Arg
    50                  55                  60

Cys Ser Arg Arg Pro Arg Trp Thr Pro Arg Ser Pro Gly
65                  70                  75
```

(2) INFORMATION FOR SEQ ID NO:22:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:22:

```
Arg Glu His Ser Glu Arg Lys Lys Gly Arg Arg Ala Ser Glu Cys Ala
 1               5                  10                  15

Ala Ala
```

(2) INFORMATION FOR SEQ ID NO:23:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:23:

```
Pro Ala Ser Ser Ser Ser Gly Ser Leu Arg Pro Ala Pro Ser Ser Thr
 1               5                  10                  15

Pro Ser Ser Pro Trp Arg Ala Ser Arg Pro Ser Arg Thr Ala Pro Ala
            20                  25                  30

Ala Pro Ser Thr Cys Thr Ser Ser Gly Thr
        35                  40
```

(2) INFORMATION FOR SEQ ID NO:24:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:24:

```
Ala Arg Ala Ala Ser Pro Pro Gly Pro Thr Thr Thr Arg Trp Pro Cys
 1               5                  10                  15
Arg Thr Arg Ser Thr Arg Ala Thr Ser Ala Thr Ser Arg Ser Ala Thr
                20                  25                  30
Ala Ala Ser Gly Gly Thr Ala Pro Ala Trp Pro Pro Arg Ser Arg Ala
                35                  40                  45
Arg Thr Pro Ser Trp Ala Gly Pro Trp Ser Ser Thr Leu Ala Arg Thr
            50                  55                  60
Thr Trp Ala Ala Ala Ala Thr Arg Pro Ala Trp Arg Thr Gly Thr Arg
65                  70                  75                  80
Ala Gly Gly Trp Pro Ala Ala Trp Trp Ala Cys Ala Gly Pro Gly Ser
                85                  90                  95
Gly Ser Ala Arg Arg Gly Ser Thr Gln Ser Ala Arg Ser Gly Gly Ala
                100                 105                 110
Arg Ala Ser Ala Arg Pro
            115
```